United States Patent
Wei et al.

(10) Patent No.: US 11,661,596 B2
(45) Date of Patent: **\*May 30, 2023**

(54) TARGETED RNA EDITING BY LEVERAGING ENDOGENOUS ADAR USING ENGINEERED RNAS

(71) Applicant: PEKING UNIVERSITY, Beijing (CN)

(72) Inventors: Wensheng Wei, Beijing (CN); Zongyi Yi, Beijing (CN); Liang Qu, Beijing (CN); Feng Tian, Beijing (CN); Chunhui Wang, Beijing (CN); Shiyou Zhu, Beijing (CN); Zhuo Zhou, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 22 days.

This patent is subject to a terminal disclaimer.

(21) Appl. No.: 17/573,525

(22) Filed: Jan. 11, 2022

(65) Prior Publication Data

US 2022/0135963 A1     May 5, 2022

Related U.S. Application Data

(63) Continuation of application No. PCT/CN2020/101246, filed on Jul. 10, 2020.

(30) Foreign Application Priority Data

Jul. 12, 2019 (WO) ................ PCT/CN2019/095802

(51) Int. Cl.
   *C12N 15/10*       (2006.01)
   *A61K 31/7088*    (2006.01)
   *C12N 15/113*     (2010.01)
   *C12N 15/86*      (2006.01)

(52) U.S. Cl.
CPC ........ *C12N 15/102* (2013.01); *A61K 31/7088* (2013.01); *C12N 15/113* (2013.01); *C12N 15/86* (2013.01); *C12Y 305/04004* (2013.01); *C12N 2310/11* (2013.01); *C12N 2310/12* (2013.01); *C12N 2310/532* (2013.01); *C12N 2710/16145* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 4,435,307 A | 3/1984 | Barbesgaard et al. | |
| 5,773,244 A | 6/1998 | Ares, Jr. et al. | |
| 9,650,627 B1* | 5/2017 | Rosenthal | C12N 15/102 |
| 10,941,402 B2 | 3/2021 | Turunen et al. | |
| 2013/0253036 A1 | 9/2013 | Collard et al. | |
| 2018/0208924 A1 | 7/2018 | Fukuda et al. | |
| 2019/0040383 A1 | 2/2019 | Klein et al. | |
| 2019/0093098 A1 | 3/2019 | Stafforst et al. | |
| 2019/0330622 A1 | 10/2019 | Turunen et al. | |
| 2019/0352641 A1 | 11/2019 | Aalto et al. | |
| 2020/0308581 A1* | 10/2020 | Clarke | C12N 15/113 |
| 2021/0310026 A1 | 10/2021 | Wei et al. | |
| 2021/0355494 A1 | 11/2021 | Wei et al. | |
| 2022/0010333 A1* | 1/2022 | Mali | C12N 15/111 |
| 2022/0064633 A1 | 3/2022 | Wei et al. | |
| 2022/0073915 A1 | 3/2022 | Wettengel et al. | |
| 2022/0098587 A1 | 3/2022 | Yuan et al. | |
| 2022/0186210 A1 | 6/2022 | Wei et al. | |
| 2022/0193142 A1 | 6/2022 | Fang et al. | |
| 2022/0307020 A1 | 9/2022 | Yuan et al. | |

FOREIGN PATENT DOCUMENTS

| | | |
|---|---|---|
| CN | 107109413 A | 8/2017 |
| CN | 109072239 A | 12/2018 |
| CN | 109477103 A | 3/2019 |
| CN | 109804069 A | 5/2019 |
| CN | 109943586 A | 6/2019 |
| JP | 2017537618 A | 12/2017 |
| JP | 2018506297 A | 3/2018 |
| TW | 202028466 A | 8/2020 |
| TW | 202043249 A | 12/2020 |
| WO | 2015134812 A1 | 9/2015 |
| WO | 2016094845 A2 | 6/2016 |
| WO | 2016097212 A1 | 6/2016 |
| WO | 2017010556 A1 | 1/2017 |
| WO | 2017050306 A1 | 3/2017 |
| WO | 2017186739 A1 | 11/2017 |
| WO | 2017220751 A1 | 12/2017 |
| WO | 2018041873 A1 | 3/2018 |
| WO | 2018041973 A1 | 3/2018 |
| WO | 2018055134 A1 | 3/2018 |
| WO | 2018134301 A1 | 7/2018 |
| WO | 2018161032 A1 | 9/2018 |
| WO | 2018208998 A1 | 11/2018 |
| WO | 2019005886 A1 | 1/2019 |

(Continued)

OTHER PUBLICATIONS

Abe, N. et al. (2018). "Preparation of Circular RNA In Vitro," Methods Mol. Biol. 1724:181-192.
Abudayyeh, O.O. et al. (Aug. 5, 2018). "C2c2 is a Single-Component Programmable RNA-Guided RNA-Targeting CRISPR Effector," Science 353:aaf5573-1-aff5573-9, 11 pages.
Abudayyeh, O.O. et al. (Jul. 26, 2019). "A Cytosine Deaminase For Programmable Single-Base RNA Editing," Science 365:382-386.
Aquino-Jarquin, G. (Mar. 31, 2020). "Novel Engineered Programmable Systems for ADAR-Mediated RNA Editing," Molecular Therapy Nucleic Acids 19:1065-1072.
Bass, B.L. et al. (Dec. 23, 1988). "An Unwinding Activity That Covalently Modifies Its Double-Stranded RNA Substrate," Cell 55:1089-1098.

(Continued)

*Primary Examiner* — Brian Whiteman
(74) *Attorney, Agent, or Firm* — Morrison & Foerster LLP

(57) ABSTRACT

Provided are methods for editing RNA by introducing a deaminase-recruiting RNA in a host cell for deamination of an adenosine in a target RNA, deaminase-recruiting RNAs used in the RNA editing methods, compositions and kits comprising the same.

25 Claims, 12 Drawing Sheets

Specification includes a Sequence Listing.

(56) References Cited

FOREIGN PATENT DOCUMENTS

| | | | |
|---|---|---|---|
| WO | 2019060746 A1 | 3/2019 |
| WO | 2019071048 A1 | 4/2019 |
| WO | 2019123429 A1 | 6/2019 |
| WO | 2019158475 A1 | 8/2019 |
| WO | 2019183641 A1 | 9/2019 |
| WO | 2020074001 A1 | 4/2020 |
| WO | 2020168051 A1 | 8/2020 |
| WO | 2020211780 A1 | 10/2020 |
| WO | 2021008447 A1 | 1/2021 |
| WO | 2021043278 A1 | 3/2021 |
| WO | 2021121266 A1 | 6/2021 |
| WO | 2021136404 A1 | 7/2021 |
| WO | 2021136408 A1 | 7/2021 |
| WO | 2021136520 A1 | 7/2021 |
| WO | 2022150974 A1 | 7/2022 |

OTHER PUBLICATIONS

Bazak, L. et al. (2014). "A-to-I RNA Editing Occurs At Over a Hundred Million Genomic Sites, Located In a Majority of Human Genes," Genome Res. 24:365-376.
Beaudry, D. et al. (1995). "An Efficient Strategy For The Synthesis of Circular RNA Molecules," Nucleic Acids Res. 23(15):3064-3066.
Bennett, C.F. (Jan. 27, 2019). "Therapeutic Antisense Oligonucleotides Are Coming of Age," Annu. Rev. Med. 70:307-321.
Boch, J. et al. (Dec. 11, 2009). "Breaking The Code Of DNA Binding Specificity Of TAL-Type III Effectors," Science 326(5959):1509-1512.
Burgess, D.J. (Oct. 2019). "Expanding Options for RNA Based Editors," Nature Reviews Genetics 20 (10):563-563, 1 page.
Charlesworth, C.T. et al. (2019, e-pub. Jan. 28, 2019). Identification of Preexisting Adaptive Immunity to Cas9 Proteins In Humans, Nat Med 25:249-254.
Chen, C.-X. et al. (2000). "A Third Member of the RNA-Specific Adenosine Deaminase Gene Family, ADAR3, Contains Both Single- and Double-Stranded RNA Binding Domains," RNA 6:755-767.
Chen, G.H. et al. (Apr. 3, 2019). "RNA-Guided Adenosine Deaminases: Advances and Challenges for Therapeutic RNA Editing," Biochemistry 58(15):1947-1957.
Chen, H. et al. (2020, e-pub. Mar. 30, 2020). "Preferential Production of RNA Rings By T4 RNA Ligase 2 Without Any Splint Through Rational Design of Precursor Strand," Nucleic Acids Research 48(9):e54, 12 pages.
Chen, L.L. (Apr. 2016). "The Biogenesis and Emerging Roles of Circular RNAs," Nat. Rev. Mol. Cell Biol. 17 (4):205-211, 7 pages.
Chew, W.L. et al. (Oct. 2016). "A Multifunctional AAV-CRISPR-Cas9 and Its Host Response," Nat Methods 13 (10):868-874.
Cong, L. et al. (Feb. 15, 2013, e-pub. Oct. 11, 2013). "Multiplex Genome Engineering Using CRISPR/Cas Systems," Science 339(6121):819-823, 9 pages.
Cox, D. B. T. et al. (Nov. 24, 2017). "RNA Editing With CRISPR-Cas13," Science 358:1019-1027.
Crunkhorn, S. (Sep. 2019). "Expanding the RNA-Editing Toolbox," Nature Reviews Drug Discovery 18 (9):667-667, 1 page.
Daniel, C. et al. (2017). "Editing Inducer Elements Increases A-to-I Editing Efficiency In The Mammalian Transcriptome," Genome Biol 18:195, 16 pages.
Dobin, A. et al. (2013, e-pub. Oct. 25, 2012). "STAR: Ultrafast Universal RNA-Seq Aligner," Bioinformatics 29:1-7.
Doubrovin, M. et al. (Jul. 31, 2001). "Imaging Transcriptional Regulation of p53-dependent Genes With Positron Emission Tomography In Vivo," Proc Natl Acad Sci USA 98(16):9300-9305, 14 pages.
Dykstra, P.B. et al. (Apr. 2022). "Engineering Synthetic RNA Devices for Cell Control," Nature Reviews Genetics 23:215-228.
Eggington, J.M. et al. (May 17, 2011). "Predicting Sites of ADAR Editing In Double-Stranded RNA," Nat. Commun. 2:319, 9 pages.

Enuka, Y. et al. (2016, e-pub. Dec. 10, 2015). "Circular RNAs Are Long-Lived and Display Only Minimal Early Alterations In Response To a Growth Factor," Nucleic Acids Res. 44(3):1370-1383.
Fire, A. et al. (Feb. 19, 1998). "Potent and Specific Genetic Interference By Double-Stranded RNA in Caenorhabditis elegans," Nature 391:806-811.
Floquet, C. (2011, e-pub. Dec. 10, 2010). "Rescue of Non-Sense Mutated p53 Tumor Suppressor Gene By Aminoglycosides," Nucleic Acids Res 39(8):3350-3362.
Fry, L.E. et al. (Jan. 25, 2020). "RNA Editing as a Therapeutic Approach for Retinal Gene Therapy Requiring Long Coding Sequences," International Journal of Molecular Sciences 21:77, 20 pages.
Fukuda, M. et al. (Feb. 2, 2017). "Construction of a Guide-RNA For Site-Directed RNA Mutagenesis Utilising Intracellular A-to-I RNA Editing," Scientific Reports 7:41478, 13 pages.
Fuster-García, C. et al. (Sep. 30, 2017). "USH2A Gene Editing Using the CRISPR System," Molecular Therapy Nucleic Acids 8:529-541.
Gallo, A.et al. (Sep. 2017, e-pub. Sep. 14, 2017). "ADAR RNA Editing In Human Disease; More To It Than Meets The I," Hum. Genet. 136(9):1265-1278.
Gaudelli, N. M. et al. (Nov. 23, 2017). "Programmable Base Editing Of A*T To G*C In Genomic DNA Without DNA Cleavage," Nature 551:464-471.
Genomes Project Consortium (Nov. 1, 2012). "An Integrated Map of Genetic Variation From 1,092 Human Genomes," Nature 491:56-65.
Gibson, D.G. et al. (May 2009, e-pub. Apr. 12, 2009). "Enzymatic Assembly of DNA Molecules Up to Several Hundred Kilobases," Nature Methods 6(5):343-347.
Grünewald, J. et al. (May 2019). "Transcriptome-Wide Off-Target RNA Editing Induced By CRISPR-Guided DNA Base Editors," Nature 569(7756):433-437, 34 pages.
Grünewald, J. et al. (Sep. 2019). "CRISPR DNA Base Editors With Reduced RNA Off-Target and Self-Editing Activities," Nat. Biotechnol. 37(9):1041-1048, 19 pages.
Haapaniemi, E. (2018, e-pub. Jun. 11, 2018). "CRISPR-Cas9 Genome Editing Induces a p53-Mediated DNA Damage Response," Nat Med 24:927-930.
Hanswillemenke, A. et al. (2015, e-pub. Nov. 23, 2015). "Site-Directed RNA Editing in Vivo Can Be Triggered by the Light-Driven Assembly of an Artificial Riboprotein," J Am Chem Soc 137:15875-15881.
Heep, M. et al. (Jan. 14, 2017). "Applying Human ADAR1p110 and ADAR1p150 for Site-Directed RNA Editing-G/C Substitution Stabilizes GuideRNAs Against Editing," Genes (Basel) 8:34, 7 pages.
Ihry, R.J. et al. (Jul. 2018, e-pub. Jun. 11, 2018). "p53 Inhibits CRISPR-Cas9 Engineering In Human Pluripotent Stem Cells," Nat Med 24:939-946.
International Preliminary Report on Patentability Opinion, dated Apr. 8, 2021, for PCT Application No. PCT/CN2019/110782, filed Oct. 12, 2019, 7 pages.
International Preliminary Report on Patentability Opinion, dated Sep. 28, 2021, for PCT Application No. PCT/CN2020/084922, filed Apr. 15, 2020, 6 pages.
International Preliminary Report on Patentability, dated Jan. 18, 2022, for PCT Application No. PCT/CN2020/101246, filed Jul. 10, 2020, 7 pages.
International Search Report and Written Opinion, dated Jan. 9, 2020, for PCT Application No. PCT/CN2019/110782, filed Oct. 12, 2019, 13 pages.
International Search Report and Written Opinion, dated Jul. 24, 2020, for PCT Application No. PCT/CN2020/084922, filed Apr. 15, 2020, 11 pages.
International Search Report and Written Opinion, dated Oct. 12, 2020, for PCT Application No. PCT/CN2020/101246, filed Jul. 10, 2020, 13 pages.
International Search Report, dated Apr. 2, 2021, for PCT Application No. PCT/CN2020/142218, 12 pages. With English Translation.
International Search Report, dated Mar. 26, 2021, for PCT Application No. PCT/CN2020/141501, 14 pages. With English Translation.

(56) References Cited

OTHER PUBLICATIONS

International Search Report, dated Mar. 30, 2021, for PCT Application No. PCT/CN2020/141506, 14 pages. With English Translation.
Zuo, E et al. (Feb. 28, 2019). "Cytosine Base Editor Generates Substantial Off-Target Single-Nucleotide Variants In Mouse Embryos," Science, 7 pages.
Jin, S. et al. (2019, e-pub. Feb. 28, 2019). "Cytosine, But Not Adenine, Base Editors Induce Genome-Wide Off-Target Mutations In Rice," Science, 7 pages.
Jinek, M. et al. (Aug. 17, 2012). "A Programmable Dual-RNA-Guided DNA Endonuclease In Adaptive Bacterial Immunity," Science 337(6096):816-821.
Katrekar, D. et al. (Apr. 2019, e-pub. Feb. 8, 2019). "In Vivo RNA Editing Of Point Mutations Via RNA-Guided Adenosine Deaminases," Nat Methods 16:239-242.
Kern, S.E. et al. (Jun. 21, 1991). "Identification of p53 as a Sequence-Specific DNA-Binding Protein," Science 252:1708-1711.
Khosravi, H,M, et al. (2021, e-pub. Sep. 27, 2021). "Site-Directed RNA Editing Recent Advances and Open Challenges," RNA Biol. 18(S1):41-50.
Kim, D. et al. (2019, e-pub. Mar. 4, 2019). "Genome-Wide Target Specificity of CRISPR RNA-Guided Adenine Base Editors," Nat Biotechnol 37:430-435.
Komor, A. C. et al. (May 19, 2016). "Programmable Editing Of a Target Base In Genomic DNA Without Double-Stranded DNA Cleavage," Nature 533:420-424.
Krawitz, P.M. et al. (Sep. 30, 2014). "Screening For Single Nucleotide Variants, Small Indels and Exon Deletions With A Next-Generation Sequencing Based Gene Panel Approach For Usher Syndrome," Molecular Genetics & Genomic Medicine 2(5):393-401.
Kristensen, L.S. et al. (Nov. 2019, e-pub. Aug. 8, 2019). "The Biogenesis, Biology and Characterization of Circular RNAs," Nat. Rev. Genet. 20:675-691.
Kuttan, A. et al. (2012, e-pub. Nov. 5, 2012). "Mechanistic Insights Into Editing-Site Specificity of ADARs," Proc. Natl. Acad. Sci. USA 109:E3295-3304.
Landrum, M.J. et al. (2016, e-pub. Nov. 17, 2015). "ClinVar: Public Archive Of Interpretations Of Clinically Relevant Variants," Nucleic Acids Res 44:D862-D868.
Levanon, E.Y. et al. (Aug. 2004). "Systematic Identification of Abundant A-to-I Editing Sites In The Human Transcriptome," Nat Biotechnol 22(8):1001-1005.
Litke, J.L. et al. (Apr. 8, 2019). "Highly Efficient Expression of Circular RNA Aptamers In Cells Using Autocatalytic Transcripts," Nat Biotechnol. 37(6):667-675.
Ma, Y. et al. (Dec. 2016). "Targeted AID-Mediated Mutagenesis (TAM) Enables Efficient Genomic Diversification In Mammalian Cells," Nat Methods 13(12):1029-1035.
Mali, P. et al. (Feb. 15, 2013, e-pub. Jan. 3, 2013). "RNA Guided Human Genome Engineering via Cas9," Science 339(6121):823-826, 8 pages.
Mays, L.E. et al. (Jan. 2011). "The Complex and Evolving Story Of T Cell Activation To AAV Vector-Encoded Transgene Products," Mol Ther 19(1):16-27.
Memczak, S. et al. (Mar. 21, 2013, e-pub. Feb. 27, 2013). "Circular RNAs Are a Large Class of Animal RNAs With Regulatory Potency," Nature 495(7441):333-338.
Merkle, T. et al. (2019, e-pub. Jan. 28, 2019). "Precise RNA Editing By Recruiting Endogenous ADARs With Antisense Oligonucleotides," Nat Biotechnol 37:133-138.
Miki, T. et al. (Apr. 1, 2019). "Induced Pluripotent Stem Cell Derivation and Ex Vivo Gene Correction Using Mucopolysaccharidosis Type 1 Disease Mouse Model," Stem Cells International 2019(6978303):1-10.
Miller, J.C. et al. (Feb. 2011, e-pub. Dec. 22, 2010). "A TALE Nuclease Architecture For Efficient Genome Editing," Nature Biotechnology 29(2):143-148.
Monteleone, L.R. et al. (Feb. 21, 2019). "A Bump-Hole Approach for Directed RNA Editing," Cell Chemical Biology 26(2):269-277.
Montiel-Gonzalez, M.F. (Nov. 5, 2013). "Correction of Mutations Within The Cystic Fibrosis Transmembrane Conductance Regulator By Site-Directed RNA Editing," Proc Natl Acad Sci USA 110:18285-18290.
Montiel-Gonzalez, M.F. et al. (2016). "An Efficient System For Selectively Altering Genetic Information Within mRNAs," Nucleic Acids Res 44:e157, 12 pages.
Montiel-Gonzalez, M.F. et al. (Mar. 1, 2019, e-pub. Nov. 29, 2018). "Current Strategies For Site-Directed RNA Editing Using ADARs," Methods 156:16-24, 25 pages.
Moscou, M.J. et al. (Dec. 11, 2009, e-pub. Oct. 29, 2009). "A Simple Cipher Governs DNA Recognition By TAL Effectors," Science 326:1501, 1 page.
Nishikura, K. (2010). "Functions and Regulation of RNA Editing By ADAR Deaminases," Annu Rev Biochem 79:321-349.
Nishikura, K. (Feb. 2016). "A-to-I Editing of Coding and Non-Coding RNAs by ADARs," Nat Rev Mol Cell Biol 17:83-96.
Ou, L. et al. (Jan. 2019). "ZFN-Mediated In Vivo Genome Editing Corrects Murine Hurler Syndrome," Mol Ther 27 (1):178-187.
Patterson, J. B. et al. (Oct. 1995). "Expression and Regulation By Interferon Of A Double-Stranded-RNA-Specific Adenosine Deaminase From Human Cells: Evidence For Two Forms Of The Deaminase," Mol Cell Biol 15 (10):5376-5388.
Pertea, M. et al. (2016, e-pub. Aug. 11, 2016). "Transcript-Level Expression Analysis of RNA-Seq Experiments With HISAT, StringTie and Ballgown," Nat Protoc 11(9):1650-1667.
Platt, R.J. et al. (Oct. 9, 2014). "CRISPR-Cas9 Knockin Mice For Genome Editing and Cancer Modeling," Cell 159:440-455.
Porteus, M. H. et al. (Aug. 2005, e-pub. Aug. 8, 2005). "Gene Targeting Using Zinc Finger Nucleases," Nat Biotechnol 23(8):967-973.
Porto, E.M. et al. (2020). "Base Editing: Advances and Therapeutic Opportunities," Nature Reviews Drug Discovery 19(12):839-859.
Puttaraju, M. et al. (1992). "Group I Permuted Intron-Exon (PIE) Sequences Self-Splice To Produce Circular Exons," Nucleic Acids Res. 20(20):5357-5364.
Qu, L. et al. (Apr. 19, 2019). "Leveraging Endogenous ADAR for Programmable Editing on RNA," Biomedical Pioneering Innovation Center, 46 pages.
Qu, L. et al. (Sep. 30, 2019, e-pub. Jul. 15, 2019). "Programmable RNA Editing By Recruiting Endogenous ADAR Using Engineered RNAs," Nature Biotechnology 37:1059-1069.
Roberts, T.C. et al. (Oct. 2020). "Advances In Oligonucleotide Drug Delivery," Nat. Rev. Drug Discov. 19:673-694.
Samaridou, E. et al. (2020, e-pub. Jun. 8, 2020). "Lipid Nanoparticles For Nucleic Acid Delivery: Current Perspectives," Adv. Drug Deliv. Rev. 154-155:37-63.
Savva, Y.A. et al. (2012). "The ADAR Protein Family," Genome Biol 13:252, 10 pages.
Schneider, M.F. et al. (2014, e-pub. Apr. 17, 2014). "Optimal GuideRNAs For Re-Directing Deaminase Activity Of hADAR1 and hADAR2 In trans," Nucleic Acids Res 42(10):e87, 9 pages.
Schuh, R.S. et al. (2018, e-pub Dec. 31, 2017). "Gene Editing of MPS I Human Fibroblasts By Co-Delivery of a CRISPR/Cas9 Plasmid and a Donor Oligonucleotide Using Nanoemulsions as Nonviral Carriers," European Journal Of Pharmaceutics And Biopharmaceutics, pp. 1-33.
Simhadri, V.L. et al. (Jun. 9, 2018). "Prevalence of Pre-Existing Antibodies to CRISPR-Associated Nuclease Cas9 in the USA Population," Mol Ther Methods Clin Dev 10:105-112.
Sinnamon, J.R. et al. (2017). "Site-Directed RNA Repair Of Endogenous Mecp2 RNA In Neurons," Proc Natl Acad Sci USA 114: E9395-E9402.
Tan, M.H. et al. (Oct. 12, 2017). "Dynamic Landscape and Regulation Of RNA Editing In Mammals," Nature 550:249-254.
Teoh, P.J. et al. (Sep. 20, 2018). "Aberrant Hyperediting Of The Myeloma Transcriptome By ADAR1 Confers Oncogenicity and Is A Marker Of Poor Prognosis," Blood 132(12):1304-1317.
Tian, N. et al. (2011, e-pub. Mar. 22, 2011). "A Structural Determinant Required For RNA Editing," Nucleic Acids Res. 39(13):5669-5681.

(56) References Cited

OTHER PUBLICATIONS

Tong, S. et al. (Nov. 2019). "Engineered Material for in vivo Delivery of Genome-Editing Machinery," Nature Reviews Material 4(11):726-737, 26 pages.
U.S. Appl. No. 17/607,796, Fang et al., filed Oct. 29, 2021.
U.S. Appl. No. 17/593,811, Wei, et al, filed Sep. 24, 2021.
U.S. Appl. No. 17/603,918, Yuan, et al, filed Oct. 14, 2021.
U.S. Appl. No. 17/626,440, Wei, et al, filed Jan. 1, 2022.
Vallecillo-Viejo, I.C. (2017, e-pub. Nov. 3, 2017). "Abundant Off-Target Edits From Site-Directed RNA Editing Can Be Reduced By Nuclear Localization Of The Editing Enzyme," RNA Biology 15:104-114.
Van Der Auwera, G.A. et al. (2013, e-pub. Oct. 2013). "From FastQ Data To High Confidence Variant Calls: The Genome Analysis Toolkit Best Practices Pipeline," Curr Protoc Bioinformatics 43:11.10, 33 pages.
Vogel, P. et al. (2014). "Improving Site-Directed RNA Editing In Vitro And In Cell Culture By Chemical Modification of The GuideRNA," Angewandte Chemie 53:6267-6271.
Vogel, P. et al. (2017, e-pub. May 31, 2017). "Switching Protein Localization by Site-Directed RNA Editing under Control of Light," ACS Synthetic Biology 6:1642-1649.
Vogel, P. et al. (2018, e-pub. Jul. 2, 2018). "Efficient and Precise Editing Of Endogenous Transcripts With SNAP-Tagged ADARs," Nat Methods 15:535-538, 20 pages.
Wagner, D. L. et al. (2018, e-pub. Oct. 29, 2018). "High Prevalence of *Streptococcus pyogenes* Cas9-Reactive T Cells Within The Adult Human Population," Nat Med 25:242-248.
Wagner, R.W. et al. (Oct. 1990). "Double-Stranded RNA Unwinding and Modifying Activity Is Detected Ubiquitously In Primary Tissues and Cell Lines," Mol Cell Biol 10(10):5586-5590.
Wahlstedt, H. et al. (Nov./Dec. 2011). "Site-Selective Versus Promiscuous A-to-I Editing," Wiley Interdisciplinary Reviews: RNA 2:761-771.
Wang, K. et al. (2010, e-pub. Jul. 3, 2010). "ANNOVAR: Functional Annotation Of Genetic Variants From High-Throughput Sequencing Data," Nucleic Acids Res 38(16):e164, 7 pages.
Wang, Y. et al. (Sep. 22, 2015). "A Phenotypic Screen for Functional Mutants of Human Adenosine Deaminase Acting on RNA 1," ACS Chem Biol. 10(11):2512-2519.
Wesselhoeft, R.A. et al. (2018). "Engineering Circular RNA For Potent and Stable Translation In Eukaryotic Cells," Nat. Commun 9:2629, 10 pages.
Wesselhoeft, R.A. et al. (2019, e-pub. May 2, 2019). "RNA Circularization Diminishes Immunogenicity and Can Extend Translation Duration In Vivo," Mol. Cell 74: 508-520.
Wettengel, J. et al. (2016, e-pub. Oct. 7, 2016). "Harnessing Human ADAR2 for RNA Repair—Recoding a PINK1 Mutation Rescues Mitophagy," Nucleic Acids Res 45:2797-2808.
Wong, S.K. et al. (2001). "Substrate Recognition By ADAR1 and ADAR2," RNA 7:846-858.
Woolf, T.M. et al. (Aug. 31, 1995). "Toward the Therapeutic Editing Of Mutated RNA Sequences," Proc Natl Acad Sci USA 92:8298-8302.
Yin, H. (Jun. 2017, e-pub. Mar. 24, 2017). "Delivery Technologies For Genome Editing," Nature Reviews Drug Discovery 16(6):387-399.
Yin, Q.-F. et al. (Oct. 26, 2012). "Long Noncoding RNAs With snoRNA Ends," Mol Cell. 48(2):219-230.
Zhang, A-X et al. (Jul. 15, 2018). "Progress In Base Editing Technology Based On CRISPR/Cas9 System And Its Application In Medical Research," Chin J Pharmacol Toxicol. 32(7):507-511. With English Abstract.
Zhang, X.O. et al. (Sep. 25, 2014). "Complementary Sequence-Mediated Exon Circularization," Cell 159:134-147.
Zheng, Y. et al. (2017, e-pub. Jan. 28, 2017). "DNA Editing In DNA/RNA Hybrids By Adenosine Deaminases That Act On RNA," Nucleic Acids Res 45(6):3369-3377.
Zhou, Y. et al. (2016, e-pub. Nov. 14, 2016). "Simultaneous Generation of Multi-Gene Knockouts in Human Cells," FEBS Letters 590:4343-4353.
Eckstein, F. (Dec. 2014). "Phosphorothioates, Essential Components of Therapeutic Oligonucleotides," Nucleic Acid Therapeutics 24(6)1374-387, 14 pages.
Pollard, K.M. et al. (Sep. 2013). "Interferon-γ and Systemic Autoimmunity," Discovery Medicine 16 (87):123-131, 14 pages.
U.S. Appl. No. 17/786,433, Fang, et al, filed Jun. 16, 2022.
U.S. Appl. No. 17/790,484, Liu, et al, filed Jun. 30, 2022.
U.S. Appl. No. 17/790,487, Yuan, et al, filed Jun. 30, 2022.
U.S. Appl. No. 17/790,488, Yuan, et al, filed Jun. 30, 2022.
Vu, L.T. et al. (Apr. 2016, e-pub. Dec. 29, 2019). "Chemical RNA Editing For Genetic Restoration: The Relationship Between The Structure and Deamination Efficiency of Carboxyvinyldeoxyuridine Oligodeoxynucleotides," Chemical Biology & Drug Design 87(4):583-593.
Xiao, Q. (Mar. 22, 2019). "Application of CRISPR/Cas9-Based Gene Editing in HIV-1/AIDS Therapy," Frontiers in Cellular and Infection Microbiology 9(69):1-15.
Xu, L. et al. (Sep. 26, 2019). "CRISPR-Edited Stem Cells In a Patient With HIV and Acute Lymphocytic Leukemia," New England Journal of Medicine 381(13):1240-1247.
Pinzon, F.F (2006). "Morality, Ethics and Bioethics as Social Limitations to the Protection of Inventions via Patents," Phronesis 13(3):1-2. English Abstract.
Genbank (May 31, 2018). NM_000203.4—"*Homo sapians* Iduronidase, Alpha-L_(IDUA), Transcript Variant 1, mRNA," 4 pages.
Zhang, X.-E. (Dec. 20, 2019). "Synthetic Biology in China: Review and Prospect," Science China Life Sciences 12:30-32, English Abstract, 31 pages.

\* cited by examiner

FIG. 4B

SEQUENCE LISTING

```
<160> NUMBER OF SEQ ID NOS: 52

<210> SEQ ID NO 1
<211> LENGTH: 122
<212> TYPE: DNA
<213> ORGANISM: Artificial Sequence
<220> FEATURE:
<223> OTHER INFORMATION: Synthesized sequence

<400> SEQUENCE: 1
aagattgtgt gtggatcgat gatgacttcc atatatacat tccttggaaa gctgaacaaa      60
atgagtgaaa actctatacc gtcattctcg tcgaactgag gtccagcaca ttactccaac     120
ag                                                                    122

<210> SEQ ID NO 2
<211> LENGTH: 116
<212> TYPE: DNA
<213> ORGANISM: Artificial Sequence
<220> FEATURE:
<223> OTHER INFORMATION: Synthesized sequence

<400> SEQUENCE: 2
gagtgagatc ttggaccaat gatgacttcc atacatgcat tccttggaaa gctgaacaaa      60
atgagtggga actctgtact atcatcttag ttgaactgag gtccaccggg ggctaa         116

<210> SEQ ID NO 3
<211> LENGTH: 508
<212> TYPE: DNA
<213> ORGANISM: Artificial Sequence
<220> FEATURE:
<223> OTHER INFORMATION: Synthesized sequence

<400> SEQUENCE: 3
cgttacataa cttacggtaa atggcccgcc tggctgaccg cccaacgacc cccgcccatt      60
gacgtcaata atgacgtatg ttcccatagt aacgccaata gggactttcc attgacgtca     120
atgggtggag tatttacggt aaactgccca cttggcagta catcaagtgt atcatatgcc     180
aagtacgccc cctattgacg tcaatgacgg taaatggccc gcctggcatt atgcccagta     240
catgacctta tgggactttc ctacttggca gtacatctac gtattagtca tcgctattac     300
catggtgatg cggttttggc agtacatcaa tgggcgtgga tagcggtttg actcacgggg     360
atttccaagt ctccacccca ttgacgtcaa tgggagtttg ttttggcacc aaaatcaacg     420
ggactttcca aaatgtcgta acaactccgc cccattgacg caaatgggcg gtaggcgtgt     480
acggtgggag gtctatataa gcagagct                                         508

<210> SEQ ID NO 4
<211> LENGTH: 111
<212> TYPE: RNA
<213> ORGANISM: Artificial Sequence
<220> FEATURE:
```

<223> OTHER INFORMATION: Synthesized sequence

<400> SEQUENCE: 4
gggagcagcc ucuggcauuc ugggagcuuc aucuggaccu gggucuucag ugaaccauug    60
uucaauaucg uccggggaca gcaucaaauc auccauugcu ugggacggca a             111

<210> SEQ ID NO 5
<211> LENGTH: 111
<212> TYPE: RNA
<213> ORGANISM: Artificial Sequence
<220> FEATURE:
<223> OTHER INFORMATION: Synthesized sequence

<400> SEQUENCE: 5
gacgcccacc gugugguugc uguccaggac ggucccggcc ugcgacacuu cggcccagag    60
cugcuccuca ucugcggggc ggggggggggc cgucgccgcg uggggucguu g            111

<210> SEQ ID NO 6
<211> LENGTH: 111
<212> TYPE: RNA
<213> ORGANISM: Artificial Sequence
<220> FEATURE:
<223> OTHER INFORMATION: Synthesized sequence

<400> SEQUENCE: 6
cauauuacag aauaccuuga uagcauccaa uuugcauccu ugguuagggu caacccagua    60
uucuccacuc uugaguucag gauggcagaa uuucaggucu cugcaguuuc u             111

<210> SEQ ID NO 7
<211> LENGTH: 111
<212> TYPE: RNA
<213> ORGANISM: Artificial Sequence
<220> FEATURE:
<223> OTHER INFORMATION: Synthesized sequence

<400> SEQUENCE: 7
gugaagauaa gccaguccuc uaguaacaga augagcaaga cggcaagagc uuacccaguc    60
acuugugugg agacuuaaau acuugcauaa agauccauug ggauaguacu c             111

<210> SEQ ID NO 8
<211> LENGTH: 111
<212> TYPE: RNA
<213> ORGANISM: Artificial Sequence
<220> FEATURE:
<223> OTHER INFORMATION: Synthesized sequence

<400> SEQUENCE: 8
gugaacguca aacugucgga ccaauauggc agaaucuucu cucaucucaa cuuuccauau    60
ccguaucaug gaaucauagc auccuguaac uacuagcucu cuuacagcug g             111

<210> SEQ ID NO 9
<211> LENGTH: 111
<212> TYPE: RNA
<213> ORGANISM: Artificial Sequence
<220> FEATURE:
<223> OTHER INFORMATION: Synthesized sequence

<400> SEQUENCE: 9
gccaaugauc ucgugaguua ucucagcagu gugagccauc agggugauga caucccaggc    60
gaucgugugg ccuccaggag cccagagcag gaaguugagg agaaggugcc u             111

-continued

```
<210> SEQ ID NO 10
<211> LENGTH: 111
<212> TYPE: RNA
<213> ORGANISM: Artificial Sequence
<220> FEATURE:
<223> OTHER INFORMATION: Synthesized sequence

<400> SEQUENCE: 10
caagacggug aaccacucca uggucuucuu gucggcuuuc ugcacugugu accccccagag    60 cuccguguug ccgacauccu gggguggcuu ccacuccaga gccacauuaa g             111

<210> SEQ ID NO 11
<211> LENGTH: 111
<212> TYPE: RNA
<213> ORGANISM: Artificial Sequence
<220> FEATURE:
<223> OTHER INFORMATION: Synthesized sequence

<400> SEQUENCE: 11
aggauucucu uuugaaguau ugcuccccca guggauuggg uggcuccauu cacuccaaug    60
cugagcacuu ccacagagug gguuaaagcg gcuccgaaca cgaaacgugu a             111

<210> SEQ ID NO 12
<211> LENGTH: 31
<212> TYPE: DNA
<213> ORGANISM: Artificial Sequence
<220> FEATURE:
<223> OTHER INFORMATION: Synthesized sequence

<400> SEQUENCE: 12
tataactagt atggtgagca agggcgagga g                                    31

<210> SEQ ID NO 13
<211> LENGTH: 41
<212> TYPE: DNA
<213> ORGANISM: Artificial Sequence
<220> FEATURE:
<223> OTHER INFORMATION: Synthesized sequence

<400> SEQUENCE: 13
tatacgtctc atctacagat tcttccggcg tgtataccTT c                         41

<210> SEQ ID NO 14
<211> LENGTH: 53
<212> TYPE: DNA
<213> ORGANISM: Artificial Sequence
<220> FEATURE:
<223> OTHER INFORMATION: Synthesized sequence

<400> SEQUENCE: 14
tatacgtctc atagagatcc ccggtcgcca ccgtgagcaa gggcgaggag ctg            53

<210> SEQ ID NO 15
<211> LENGTH: 51
<212> TYPE: DNA
<213> ORGANISM: Artificial Sequence
<220> FEATURE:
<223> OTHER INFORMATION: Synthesized sequence

<400> SEQUENCE: 15
uaaaccgagg gaucauaggg gacugaauuc accauucuuc ucccaauccc u              51

<210> SEQ ID NO 16
<211> LENGTH: 151
<212> TYPE: DNA
```

```
<213> ORGANISM: Artificial Sequence
<220> FEATURE:
<223> OTHER INFORMATION: Synthesized sequence

<400> SEQUENCE: 16
acuacaguug cuccgauauu uaggcuacgu caauaggcac uaacuuauug gcgcugguga      60
acggacuucc ucucgaguac cagaagauga cuacaaaacu ccuuuccauu gcgaguaucg     120
gagucuggcu caguuuggcc agggaggcac u                                   151

<210> SEQ ID NO 17
<211> LENGTH: 51
<212> TYPE: DNA
<213> ORGANISM: Artificial Sequence
<220> FEATURE:
<223> OTHER INFORMATION: Synthesized sequence

<400> SEQUENCE: 17
gcccttgctc actggcagag ccctccagca tcgcgagcag gcgctgcctc c               51

<210> SEQ ID NO 18
<211> LENGTH: 151
<212> TYPE: DNA
<213> ORGANISM: Artificial Sequence
<220> FEATURE:
<223> OTHER INFORMATION: Synthesized sequence

<400> SEQUENCE: 18
acuacaguug cuccgauauu uaggcuacgu caauaggcac uaacuuauug gcgcugguga      60
acggacuucc ucucgaguac cagaagauga cuacaaaacu ccuuuccauu gcgaguaucg     120
gagucuggcu caguuuggcc agggaggcac u                                   151

<210> SEQ ID NO 19
<211> LENGTH: 116
<212> TYPE: DNA
<213> ORGANISM: Artificial Sequence
<220> FEATURE:
<223> OTHER INFORMATION: Synthesized sequence

<400> SEQUENCE: 19
gagtgagatc ttggaccaat gatgacttcc atacatgcat tccttggaaa gctgaacaaa      60
atgagtggga actctgtact atcatcttag ttgaactgag gtccaccggg ggctaa         116

<210> SEQ ID NO 20
<211> LENGTH: 122
<212> TYPE: DNA
<213> ORGANISM: Artificial Sequence
<220> FEATURE:
<223> OTHER INFORMATION: Synthesized sequence

<400> SEQUENCE: 20
aagattgtgt gtggatcgat gatgacttcc atatatacat tccttggaaa gctgaacaaa      60
atgagtgaaa actctatacc gtcattctcg tcgaactgag gtccagcaca ttactccaac     120
ag                                                                   122

<210> SEQ ID NO 21
<211> LENGTH: 708
<212> TYPE: DNA
<213> ORGANISM: Artificial Sequence
<220> FEATURE:
<223> OTHER INFORMATION: Synthesized sequence
```

<400> SEQUENCE: 21

```
atggtgagca agggcgagga ggataacatg gccatcatca aggagttcat gcgcttcaag      60
gtgcacatgg agggctccgt gaacggccac gagttcgaga tcgagggcga gggcgagggc     120
cgccccctacg agggcaccca gaccgccaag ctgaaggtga ccaagggtgg cccccctgccc   180
ttcgcctggg acatcctgtc ccctcagttc atgtacggct ccaaggccta cgtgaagcac    240
cccgccgaca tccccgacta cttgaagctg tccttccccg agggcttcaa gtgggagcgc    300
gtgatgaact tcgaggacgg cggcgtggtg accgtgaccc aggactcctc cctgcaggac    360
ggcgagttca tctacaaggt gaagctgcgc ggcaccaact tcccctccga cggcccgta    420
atgcagaaga agaccatggg ctgggaggcc tcctccgagc ggatgtaccc cgaggacggc    480
gccctgaagg gcgagatcaa gcagaggctg aagctgaagg acggcggcca ctacgacgct    540
gaggtcaaga ccacctacaa ggccaagaag cccgtgcagc tgcccggcgc ctacaacgtc    600
aacatcaagt tggacatcac ctcccacaac gaggactaca ccatcgtgga acagtacgaa    660
cgcgccgagg gccgccactc caccggcggc atggacgagc tgtacaag               708
```

<210> SEQ ID NO 22
<211> LENGTH: 99
<212> TYPE: DNA
<213> ORGANISM: Artificial Sequence
<220> FEATURE:
<223> OTHER INFORMATION: Synthesized sequence

<400> SEQUENCE: 22

```
ctgcagggcg gaggaggcag cggcggagga ggcagcggcg gaggaggcag cagaaggtat    60
acacgccgga agaatctgta gagatccccg gtcgccacc                          99
```

<210> SEQ ID NO 23
<211> LENGTH: 717
<212> TYPE: DNA
<213> ORGANISM: Artificial Sequence
<220> FEATURE:
<223> OTHER INFORMATION: Synthesized sequence

<400> SEQUENCE: 23

```
gtgagcaagg gcgaggagct gttcaccggg gtggtgccca tcctggtcga gctggacggc     60
gacgtaaacg gccacaagtt cagcgtgtcc ggcgagggcg agggcgatgc cacctacggc    120
aagctgaccc tgaagttcat ctgcaccacc ggcaagctgc ccgtgccctg gcccaccctc    180
gtgaccaccc tgacctacgg cgtgcagtgc ttcagccgct accccgacca catgaagcag    240
cacgacttct tcaagtccgc catgcccgaa ggctacgtcc aggagcgcac catcttcttc    300
aaggacgacg gcaactacaa gacccgcgcc gaggtgaagt tcgagggcga caccctggtg    360
aaccgcatcg agctgaaggg catcgacttc aaggaggacg gcaacatcct ggggcacaag    420
ctggagtaca actacaacag ccacaacgtc tatatcatgg ccgacaagca gaagaacggc    480
atcaaggtga acttcaagat ccgccacaac atcgaggacg gcagcgtgca gctcgccgac    540
cactaccagc agaacacccc catcggcgac ggccccgtgc tgctgcccga caaccactac    600
ctgagcaccc agtccgccct gagcaaagac cccaacgaga gcgcgatca catggtcctg    660
ctggagttcg tgaccgccgc cgggatcact ctcggcatgg acgagctgta caagtaa      717
```

<210> SEQ ID NO 24
<211> LENGTH: 51
<212> TYPE: DNA

<213> ORGANISM: Artificial Sequence
<220> FEATURE:
<223> OTHER INFORMATION: Synthesized sequence

<400> SEQUENCE: 24
ctgcagggcg gaggaggcag cgcctgctcg cgatgctaga gggctctgcc a        51

<210> SEQ ID NO 25
<211> LENGTH: 21
<212> TYPE: RNA
<213> ORGANISM: Artificial Sequence
<220> FEATURE:
<223> OTHER INFORMATION: Synthesized sequence

<400> SEQUENCE: 25
aaccaugccg acugauggca g        21

<210> SEQ ID NO 26
<211> LENGTH: 26
<212> TYPE: RNA
<213> ORGANISM: Artificial Sequence
<220> FEATURE:
<223> OTHER INFORMATION: Synthesized sequence

<400> SEQUENCE: 26
cugccaucag ucggcgugga cuguag        26

<210> SEQ ID NO 27
<211> LENGTH: 71
<212> TYPE: RNA
<213> ORGANISM: Artificial Sequence
<220> FEATURE:
<223> OTHER INFORMATION: Synthesized sequence

<400> SEQUENCE: 27
acagcuccuc gcccuugcuc acuggcagag cccuccagca ucgcgagcag gcgcugccuc        60
cuccgccgcu g        71

<210> SEQ ID NO 28
<211> LENGTH: 121
<212> TYPE: RNA
<213> ORGANISM: Artificial Sequence
<220> FEATURE:
<223> OTHER INFORMATION: Synthesized sequence

<400> SEQUENCE: 28
cacacacaaa cacacacaac acaacacagc uccucgcccu ugcucacugg cagagcccuc        60
cagcaucgcg agcaggcgcu gccuccuccg ccgcugcaac acacaaaacc accaccaa        120 c        121

<210> SEQ ID NO 29
<211> LENGTH: 171
<212> TYPE: RNA
<213> ORGANISM: Artificial Sequence
<220> FEATURE:
<223> OTHER INFORMATION: Synthesized sequence

<400> SEQUENCE: 29
accacacaca caaccaccac acacacacac acaaacacac acaacacaac acagcuccuc        60
gcccuugcuc acuggcagag cccuccagca ucgcgagcag gcgcugccuc cuccgccgcu        120
gcaacacaca aaaccaccac accaaccccca caaccacac acccacacaa c        171

```
<210> SEQ ID NO 30
<211> LENGTH: 111
<212> TYPE: RNA
<213> ORGANISM: Artificial Sequence
<220> FEATURE:
<223> OTHER INFORMATION: Synthesized sequence

<400> SEQUENCE: 30
gaugggcacc accccgguga acagcuccuc gcccuugcuc acuggcagag cccuccagca    60
ucgcgagcag gcgcugccuc cuccgccgcu gccuccuccg ccgcugccuc c             111

<210> SEQ ID NO 31
<211> LENGTH: 161
<212> TYPE: RNA
<213> ORGANISM: Artificial Sequence
<220> FEATURE:
<223> OTHER INFORMATION: Synthesized sequence

<400> SEQUENCE: 31
cacacacaaa cacacacaac acaacgaugg gcaccacccc ggugaacagc uccucgcccu    60
ugcucacugg cagagcccuc cagcaucgcg agcaggcgcu gccuccuccg ccgcugccuc   120
cuccgccgcu gccucccaac acacaaaacc accacaccaa c                       161

<210> SEQ ID NO 32
<211> LENGTH: 211
<212> TYPE: RNA
<213> ORGANISM: Artificial Sequence
<220> FEATURE:
<223> OTHER INFORMATION: Synthesized sequence

<400> SEQUENCE: 32
accacacaca caaccaccac acacacacac acaaacacac acaacacaac gaugggcacc    60
accccgguga acagcuccuc gcccuugcuc acuggcagag cccuccagca ucgcgagcag   120
gcgcugccuc cuccgccgcu gccuccuccg ccgcugccuc ccaacacaca aaaccaccac   180
accaacccca acaaccacac acccacacaa c                                  211

<210> SEQ ID NO 33
<211> LENGTH: 123
<212> TYPE: RNA
<213> ORGANISM: Artificial Sequence
<220> FEATURE:
<223> OTHER INFORMATION: Synthesized sequence

<400> SEQUENCE: 33
uugccaugug uaugugggga gacggucggg uccagauauu cguaucuguc gaguagagug    60 ugggcuccc acauacucug augauccaga gacgauauua cgucucagga ucauucaugg   120
caa                                                                 123

<210> SEQ ID NO 34
<211> LENGTH: 71
<212> TYPE: RNA
<213> ORGANISM: Artificial Sequence
<220> FEATURE:
<223> OTHER INFORMATION: Synthesized sequence

<400> SEQUENCE: 34
acagcuccuc gcccuugcuc acuggcagag cccuccagca ucgcgagcag gcgcugccuc    60
cuccgccgcu g                                                         71

<210> SEQ ID NO 35
```

```
<211> LENGTH: 71
<212> TYPE: RNA
<213> ORGANISM: Artificial Sequence
<220> FEATURE:
<223> OTHER INFORMATION: Synthesized sequence

<400> SEQUENCE: 35
uuucagcuau accugcccgg uauaaaggga cguucacacc gcgauguucu cugcugggga    60
auugcgcgau a                                                        71

<210> SEQ ID NO 36
<211> LENGTH: 111
<212> TYPE: RNA
<213> ORGANISM: Artificial Sequence
<220> FEATURE:
<223> OTHER INFORMATION: Synthesized sequence

<400> SEQUENCE: 36
gaugggcacc accccgguga acagcuccuc gcccuugcuc acuggcagag cccuccagca    60
ucgcgagcag gcgcugccuc cuccgccgcu gccuccuccg ccgcugccuc c            111

<210> SEQ ID NO 37
<211> LENGTH: 111
<212> TYPE: RNA
<213> ORGANISM: Artificial Sequence
<220> FEATURE:
<223> OTHER INFORMATION: Synthesized sequence

<400> SEQUENCE: 37
uaccgcuaca gccacgcuga uuucagcuau accugcccgg uauaaaggga cguucacacc    60
gcgauguucu cugcugggga auugcgcgau auucaggauu aaaagaagug c             111

<210> SEQ ID NO 38
<211> LENGTH: 151
<212> TYPE: RNA
<213> ORGANISM: Artificial Sequence
<220> FEATURE:
<223> OTHER INFORMATION: Synthesized sequence

<400> SEQUENCE: 38
acuacaguug cuccgauauu uaggcuacgu caauaggcac uaacuuauug gcgcuggcuga   60 acggacuucc ucucgaguac cagaagauga cuacaaaacu ccuuuccauu gcgaguaucg   120
gagucuggcu caguuuggcc agggaggcac u                                  151

<210> SEQ ID NO 39
<211> LENGTH: 31
<212> TYPE: RNA
<213> ORGANISM: Artificial Sequence
<220> FEATURE:
<223> OTHER INFORMATION: Synthesized sequence

<400> SEQUENCE: 39
acuggcagag cccuccagca ucgcgagcag g                                   31

<210> SEQ ID NO 40
<211> LENGTH: 51
<212> TYPE: RNA
<213> ORGANISM: Artificial Sequence
<220> FEATURE:
<223> OTHER INFORMATION: Synthesized sequence

<400> SEQUENCE: 40
gcccuugcuc acuggcagag cccuccagca ucgcgagcag gcgcugccuc c              51
```

<210> SEQ ID NO 41
<211> LENGTH: 71
<212> TYPE: RNA
<213> ORGANISM: Artificial Sequence
<220> FEATURE:
<223> OTHER INFORMATION: Synthesized sequence

<400> SEQUENCE: 41
acagcuccuc gcccuugcuc acuggcagag cccuccagca ucgcgagcag gcgcugccuc    60
cuccgcccug c                                                         71

<210> SEQ ID NO 42
<211> LENGTH: 91
<212> TYPE: RNA
<213> ORGANISM: Artificial Sequence
<220> FEATURE:
<223> OTHER INFORMATION: Synthesized sequence

<400> SEQUENCE: 42
accccgguga acagcuccuc gcccuugcuc acuggcagag cccuccagca ucgcgagcag    60
gcgcugccuc cuccgcccug cagcuuguac a                                   91

<210> SEQ ID NO 43
<211> LENGTH: 111
<212> TYPE: RNA
<213> ORGANISM: Artificial Sequence
<220> FEATURE:
<223> OTHER INFORMATION: Synthesized sequence

<400> SEQUENCE: 43
gaugggcacc accccgguga acagcuccuc gcccuugcuc acuggcagag cccuccagca    60
ucgcgagcag gcgcugccuc cuccgcccug cagcuuguac agcucgucca u            111

<210> SEQ ID NO 44
<211> LENGTH: 131
<212> TYPE: RNA
<213> ORGANISM: Artificial Sequence
<220> FEATURE:
<223> OTHER INFORMATION: Synthesized sequence

<400> SEQUENCE: 44
gcucgaccag gaugggcacc accccgguga acagcuccuc gcccuugcuc acuggcagag    60
cccuccagca ucgcgagcag gcgcugccuc cuccgcccug cagcuuguac agcucgucca   120
ugccgccggu g                                                        131

<210> SEQ ID NO 45
<211> LENGTH: 151
<212> TYPE: RNA
<213> ORGANISM: Artificial Sequence
<220> FEATURE:
<223> OTHER INFORMATION: Synthesized sequence

<400> SEQUENCE: 45
ucgccgucca gcucgaccag gaugggcacc accccgguga acagcuccuc gcccuugcuc    60
acuggcagag cccuccagca ucgcgagcag gcgcugccuc cuccgcccug cagcuuguac   120
agcucgucca ugccgccggu ggaguggcgg c                                  151

<210> SEQ ID NO 46
<211> LENGTH: 111
<212> TYPE: RNA

```
<213> ORGANISM: Artificial Sequence
<220> FEATURE:
<223> OTHER INFORMATION: Synthesized sequence

<400> SEQUENCE: 46
gaugggcacc accccgguga acagcuccuc gcccuugcuc acuggcagag cccuccagca      60
ucgcgagcag gcgcugccuc cuccgccgcu gccuccuccg ccgcugccuc c              111

<210> SEQ ID NO 47
<211> LENGTH: 111
<212> TYPE: RNA
<213> ORGANISM: Artificial Sequence
<220> FEATURE:
<223> OTHER INFORMATION: Synthesized sequence

<400> SEQUENCE: 47
uaccgcuaca gccacgcuga uuucagcuau accugcccgg uauaaaggga cguucacacc      60
gcgauguucu cugcugggga auugcgcgau auucaggauu aaaagaagug c              111

<210> SEQ ID NO 48
<211> LENGTH: 111
<212> TYPE: RNA
<213> ORGANISM: Artificial Sequence
<220> FEATURE:
<223> OTHER INFORMATION: Synthesized sequence

<400> SEQUENCE: 48
gaugggcacc accccgguga acagcuccuc gcccuugcuc acuggcagag cccuccagca      60
ucgcgagcag gcgcugccuc cuccgccgcu gccuccuccg ccgcugccuc c              111

<210> SEQ ID NO 49
<211> LENGTH: 111
<212> TYPE: RNA
<213> ORGANISM: Artificial Sequence
<220> FEATURE:
<223> OTHER INFORMATION: Synthesized sequence

<400> SEQUENCE: 49
uaccgcuaca gccacgcuga uuucagcuau accugcccgg uauaaaggga cguucacacc      60
gcgauguucu cugcugggga auugcgcgau auucaggauu aaaagaagug c              111

<210> SEQ ID NO 50
<211> LENGTH: 74
<212> TYPE: RNA
<213> ORGANISM: Artificial Sequence
<220> FEATURE:
<223> OTHER INFORMATION: Synthesized sequence

<400> SEQUENCE: 50
gcagcggcgg aggaggcagc gccugcucgc gaugcuagag ggcucugcca gugagcaagg      60
gcgaggagcu guuc                                                       74

<210> SEQ ID NO 51
<211> LENGTH: 87
<212> TYPE: RNA
<213> ORGANISM: Artificial Sequence
<220> FEATURE:
<223> OTHER INFORMATION: Synthesized sequence

<400> SEQUENCE: 51
gagcuguaca agcugcaggg cggaggaggc agcgccugcu cgcgaugcua gagggcucug      60
ccagugagca agggcgagga gcuguuc                                         87
```

```
<210> SEQ ID NO 52
<211> LENGTH: 7
<212> TYPE: RNA
<213> ORGANISM: Artificial Sequence
<220> FEATURE:
<223> OTHER INFORMATION: Synthesized sequence

<400> SEQUENCE: 52 guacaag                                                                7
```

TARGETED RNA EDITING BY LEVERAGING ENDOGENOUS ADAR USING ENGINEERED RNAS

CROSS REFERENCE TO RELATED APPLICATIONS

This application is a continuation application of International Application No. PCT/CN2020/101246, filed internationally on Jul. 10, 2020, which claims priority benefit of International Patent Application No. PCT/CN2019/095802 filed Jul. 12, 2019, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165392000101SUBSEQLIST.TXT, date recorded: May 12, 2022, size: 16,736 bytes).

FIELD

The present disclosure relates generally to methods and compositions for editing RNAs using an engineered RNA capable of recruiting an adenosine deaminase to deaminate one or more adenosines in target RNAs.

BACKGROUND

Genome editing is a powerful tool for biomedical research and development of therapeutics for diseases. Editing technologies using engineered nucleases, such as zinc finger nucleases (ZFNs), transcription activator-like effector nucleases (TALENs), and Cas proteins of CRISPR system have been applied to manipulate the genome in a myriad of organisms. Recently, taking advantage of the deaminase proteins, such as Adenosine Deaminase Acting on RNA (ADAR), new tools were developed for RNA editing. In mammalian cells, there are three types of ADAR proteins. Adar1 (two isoforms, p110 and p150), Adar2 and Adar3 (catalytically inactive). The catalytic substrate of ADAR protein is double-stranded RNA, and ADAR can remove the —NH2 group from an adenosine (A) nucleobase, changing A to inosine (I). (I) is recognized as guanosine (G) and paired with cytidine (C) during subsequent cellular transcription and translation processes. To achieve targeted RNA editing, the ADAR protein or its catalytic domain was fused with a λN peptide, a SNAP-tag or a Cas protein (dCas13b), and a guide RNA was designed to recruit the chimeric ADAR protein to the target site. Alternatively, overexpressing ADAR1 or ADAR2 proteins together with an R/G motif-bearing guide RNA was also reported to enable targeted RNA editing.

However, currently available ADAR-mediated RNA editing technologies have certain limitations. For example, the most effective in vivo delivery for gene therapy is through viral vectors, but the highly desirable adeno-associated virus (AAV) vectors are limited with the cargo size (~4.5 kb), making it challenging for accommodating both the protein and the guide RNA. Furthermore, over-expression of ADAR1 has recently been reported to confer oncogenicity in multiple myelomas due to aberrant hyper-editing on RNAs, and to generate substantial global off-targeting edits. In addition, ectopic expression of proteins or their domains of non-human origin has potential risk of eliciting immmogenicity. Moreover, pre-existing adaptive immunity and p53-mediated DNA damage response may compromise the efficacy of the therapeutic protein, such as Cas9.

BRIEF SUMMARY

The present application provides methods of RNA editing using ADAR-recruiting RNAs ("dRNA" or "arRNA") which are capable of leveraging endogenous Adenosine Deaminase Acting on RNA ("ADAR") proteins for the RNA editing. Also provided herein are engineered dRNAs or constructs comprising a nucleic acid encoding the engineered dRNAs used in these methods, and compositions and kits comprising the same. Also provided herein are methods for treating or preventing a disease or condition in an individual comprising editing a target RNA associated with the disease or condition in a cell of the individual.

In one aspect, provided herein are methods for editing a target RNA in a host cell, comprising introducing a deaminase-recruiting RNA (dRNA) or a construct comprising a nucleic acid encoding the dRNA into the host cell, wherein:

(1) the dRNA comprises a targeting RNA sequence that is at least partially complementary to the target RNA, (2) the dRNA is capable of recruiting an adenosine deaminase acting on RNA (ADAR), and (3) the dRNA is a circular RNA or capable of forming a circular RNA.

In some embodiments, the dRNA is a linear RNA capable of forming a circular RNA. In some embodiments, the dRNA further comprises a 3' ligation sequence and a 5' ligation sequence. In some embodiments, the 3' ligation sequence and the 5' ligation sequence are at least partially complementary to each other. In some embodiments, the 3' ligation sequence and the 5' ligation sequence are about 20 to about 75 nucleotides in length. In some embodiments, the dRNA is circularized by an RNA ligase. In some embodiments, the RNA ligase is RNA ligase RtcB. In some embodiments, the RNA ligase RtcB is expressed endogenously in the host cell. In some embodiments, the dRNA is a circular RNA.

In some embodiments, the method comprises introducing a construct comprising a nucleic acid encoding the dRNA into the host cell. In some embodiments, the construct further comprises a 3' twister ribozyme sequence linked to the 3' end of the nucleic acid encoding the dRNA and a 5' twister ribozyme sequence linked to the 5' end of the nucleic acid encoding the dRNA. In some embodiments, the V twister sequence is twister P3 U2A and the 5' twister sequence is twister P1. In some embodiments, the 5' twister sequence is twister P3 U2A and the 3' twister sequence is twister P1.

In another aspect, provided herein are methods for editing a target RNA in a host cell, comprising introducing a deaminase-recruiting RNA (dRNA) or a construct comprising a nucleic acid encoding the dRNA into the host cell, wherein the dRNA comprises:

(1) a targeting RNA sequence that is at least partially complementary to the target RNA and (2) a small nucleolar RNA (snoRNA) sequence linked to the 3' and/or 5' ends of the targeting RNA sequence;

and wherein the dRNA is capable of recruiting an adenosine deaminase acting on RNA (ADAR).

In some embodiments, the dRNA comprises a snoRNA sequence linked to the 5' end of the targeting RNA sequence ("5' snoRNA sequence"). In some embodiments, the dRNA comprises a snoRNA sequence linked to the 3' end of the targeting RNA sequence (3' snoRNA sequence"). In some embodiments, the snoRNA sequence is at least about 70 nucleotides in length. In some embodiments, the 3' snoRNA sequence comprises the nucleic acid sequence of SEQ ID NO: 1. In some embodiments, the 5' snoRNA sequence comprises the nucleic acid sequence of SEQ ID NO: 2. In some embodiments, the snoRNA sequence is a C/D Box snoRNA sequence. In some embodiments, the snoRNA sequence is an H/ACA Box snoRNA sequence. In some embodiments, the snoRNA sequence is a composite C/D Box and H/ACA Box snoRNA sequence. In some embodiments, the snoRNA sequence is an orphan snoRNA sequence. In some embodiments, the method comprises introducing a construct comprising a nucleic acid encoding the dRNA into the host cell. In some embodiments, the construct further comprises a promoter operably linked to the nucleic acid encoding the dRNA. In some embodiments, the promoter is a polymerase II promoter ("Pol II promoter"). In some embodiments, the construct is a viral vector or a plasmid. In some embodiments, the construct is an AAV vector.

In another aspect, provided herein are methods for editing a target RNA in a host cell, comprising introducing a construct comprising a nucleic acid encoding a deaminase-recruiting RNA (dRNA) into the host cell, wherein:

(1) the dRNA comprises a targeting RNA sequence that is at least partially complementary to the target RNA, (2) the dRNA is capable of recruiting an adenosine deaminase acting on RNA (ADAR), and (3) the construct comprises a polymerase II promoter ("Pol II promoter") operably linked the nucleic acid encoding the dRNA.

In some embodiments, the pol II promoter is a CMV promoter. In some embodiments, the CMV promoter comprises the nucleic acid sequence of SEQ ID NO: 3.

The following embodiments are applicable to all three aspects described above. In some embodiments, the construct is a viral vector or a plasmid. In some embodiments, the construct is an AAV vector. In some embodiments, the ADAR is endogenously expressed by the host cell. In some embodiments, the host cell is a T cell. In some embodiments, the targeting RNA sequence is more than 50 nucleotides in length. In some embodiments, the targeting RNA sequence is about 100 to about 180 nucleotides in length. In some embodiments, the targeting RNA sequence is about 100 to about 150 nucleotides in length. In some embodiments, the targeting RNA sequence comprises a cytidine, adenosine or uridine directly opposite the target adenosine in the target RNA. In some embodiments, the targeting RNA sequence comprises a cytidine mismatch directly opposite the target adenosine in the target RNA. In some embodiments, the cytidine mismatch is located at least 20 nucleotides away from the 3' end of the targeting RNA sequence, and at least 5 nucleotides away from the 5' end of the targeting RNA sequence. In some embodiments, the targeting RNA sequence further comprises one or more guanosines each opposite a non-target adenosine in the target RNA. In some embodiments, the targeting RNA sequence comprises two or more consecutive mismatch nucleotides opposite a non-target adenosine in the target RNA.

In some embodiments, the 5' nearest neighbor of the target adenosine in the target RNA is a nucleotide selected from U, C, A and G with the preference U>C≈A>G and the 3' nearest neighbor of the target adenosine in the target RNA is a nucleotide selected from G, C, A and U with the preference G>C>A=U. In some embodiments, the target adenosine is in a three-base motif selected from the group consisting of UAG, UAC, UAA, UAU, CAG, CAC, CAA, CAU, AAG, AAC, AAA, AAU, GAG, GAC, GAA and GAU in the target RNA. In some embodiments, the three-base motif is UAG, and the targeting RNA comprises an A directly opposite the uridine in the three-base motif, a cytidine directly opposite the target adenosine, and a cytidine, guanosine or uridine directly opposite the guanosine in the three-base motif. In some embodiments, the target RNA is an RNA selected from the group consisting of a pre-messenger RNA, a messenger RNA, a ribosomal RNA, a transfer RNA, a long non-coding RNA and a small RNA. In some embodiments, the target RNA is a pre-messenger RNA.

In some embodiments, the method further comprises introducing an inhibitor of ADAR3 to the host cell. In some embodiments, the method further comprises introducing a stimulator of interferon to the host cell. In some embodiments, the method comprises introducing a plurality of dRNAs or constructs each targeting a different target RNA. In some embodiments, the method further comprises introducing an ADAR (e.g., exogenous ADAR) to the host cell. In some embodiments, the efficiency of editing the target RNA is at least 40%. In some embodiments, the construct or the dRNA does not induce immune response. In some embodiments, the ADAR is an ADAR1 comprising an E1008 mutation.

In some embodiments, deamination of the target adenosine in the target RNA results in a missense mutation, an early stop codon, aberrant splicing, or alternative splicing in the target RNA, or reversal of a missense mutation, an early stop codon, aberrant splicing, or alternative splicing in the target RNA. In some embodiments, deamination of the target adenosine in the target RNA results in point mutation, truncation, elongation and/or misfolding of the protein encoded by the target RNA, or a functional, full-length, correctly-folded and/or wild-type protein by reversal of a missense mutation, an early stop codon, aberrant splicing, or alternative splicing in the target RNA. In some embodiments, the host cell is a eukaryotic cell. In some embodiments, the host cell is a mammalian cell. In some embodiments, the host cell is a human or mouse cell. Also provided herein are edited RNAs or host cells having the edited RNAs produced by any one of the methods provided in the above three aspects.

In another aspect, provided herein are methods for treating or preventing a disease or condition in an individual, comprising editing a target RNA associated with the disease or condition in a cell of the individual according to any one of the methods provided above. In some embodiments, the disease or condition is a hereditary genetic disease or a disease or condition associated with one or more acquired genetic mutations. In some embodiments, the target RNA has a G to A mutation. In some embodiments, the disease or condition is a monogenetic disease or condition. In some embodiments, the disease or condition is a polygenetic disease or condition.

In some embodiments, the target RNA is TP53, and the disease or condition is cancer. In some embodiments, the target RNA is IDUA, and the disease or condition is Mucopolysaccharidosis type I (MPS I). In some embodiments, the target RNA is COL3A1, and the disease or condition is Ehlers-Danios syndrome. In some embodiments, the target RNA is BMPR2, and the disease or condition is Joubert syndrome. In some embodiments, the target RNA is FANCC, and the disease or condition is Fanconi anemia. In some embodiments, the target RNA is MYBPC3, and the disease or condition is primary familial hypertrophic cardiomyopathy. In some embodiments, the target RNA is IL2RG, and the disease or condition is X-linked severe combined immunodeficiency.

In another aspect, provided herein is a deaminase-recruiting RNAs (dRNA) for editing a target RNA comprising a targeting RNA sequence that is at least partially complementary to the target RNA, wherein the dRNA is capable of recruiting an Adenosine Deaminase Acting on RNA (ADAR), and wherein the dRNA is circular or is capable of forming a circular RNA. In some embodiments, the dRNA is a linear RNA capable of forming a circular RNA. In some embodiments, the dRNA further comprises a 3' ligation sequence and a 5' ligation sequence. In some embodiments, the 3' ligation sequence and the 5' ligation sequence are at least partially complementary to each other. In some embodiments, the 3' ligation sequence and the 5' ligation sequence are about 20 to about 75 nucleotides in length. In some embodiments, the dRNA is a circular RNA. In some embodiments, the target RNA is an RNA selected from the group consisting of a pre-messenger RNA, a messenger RNA, a ribosomal RNA, a transfer RNA, a long non-coding RNA and a small RNA. Also provided herein are constructs comprising a nucleic acid encoding the dRNA as described in this aspect. In some embodiments, the construct further comprises a 3' twister ribozyme sequence linked to the 3' end of the nucleic acid encoding the dRNA and a 5' twister ribozyme sequence linked to the 5' end of the nucleic acid encoding the dRNA. In some embodiments, the 3' twister sequence is twister P3 U2A and the 5' twister sequence is twister P1. In some embodiments, wherein the 5' twister sequence is twister P3 U2A and the 3' twister sequence is twister P1. Also provided herein are host cells comprising the construct or dRNA as described in this aspect. Also provided herein are kits for editing a target RNA in a host cell comprising the construct or dRNA as described in this aspect.

In another aspect, also provided herein is a deaminase-recruiting RNA (dRNA) for editing a target RNA comprising:
 (1) a targeting RNA sequence that is at least partially complementary to the target RNA and
 (2) 3 small nucleolar RNA (snoRNA) sequence at the 3' and/or 5' ends of the targeting RNA sequence;
wherein the dRNA is capable of recruiting an adenosine deaminase acting on RNA (ADAR).

In some embodiments, the dRNA comprises a snoRNA sequence linked to the 5' end of the targeting RNA sequence ("5' snoRNA sequence"). In some embodiments, the dRNA comprises a snoRNA sequence linked to the 3' end of the targeting RNA sequence (3' snoRNA sequence"). In some embodiments, the snoRNA sequence is at least about 70 nucleotides in length. In some embodiments, the 3' snoRNA sequence comprises the nucleic acid sequence of SEQ ID NO: 1. In some embodiments, the 5' snoRNA sequence comprises the nucleic acid sequence of SEQ ID NO: 2. In some embodiments, the snoRNA sequence is a C/D Box snoRNA sequence. In some embodiments, the snoRNA sequence is an H/ACA Box snoRNA sequence. In some embodiments, the snoRNA sequence is a composite C/D Box and H/ACA Box snoRNA sequence. In some embodiments, the snoRNA sequence is an orphan snoRNA sequence. Also provided herein are constructs comprising a nucleic acid encoding the dRNA as described in this aspect. In some embodiments, the construct further comprises a promoter operably linked to the nucleic acid encoding the dRNA. In some embodiments, the promoter is a polymerase II promoter ("Pol II promoter"). In some embodiments, the target RNA is an RNA selected from the group consisting of a pre-messenger RNA, a messenger RNA, a ribosomal RNA, a transfer RNA, a long non-coding RNA and a small RNA. Also provided herein are host cells comprising the construct or dRNA as described in this aspect. Also provided herein are kits for editing a target RNA in a host cell comprising the construct or dRNA as described in this aspect.

In another aspect, provided herein is a construct comprising a nucleic acid encoding a deaminase-recruiting RNA (dRNA) into the host cell, wherein:
 (1) the dRNA comprises a targeting RNA sequence that is at least partially complementary to the target RNA,
 (2) the dRNA is capable of recruiting an adenosine deaminase acting on RNA (ADAR), and
 (3) the construct comprises a polymerase II promoter ("Pol II promoter") operably linked to the nucleic acid encoding the dRNA.

In some embodiments, the pol II promoter is a CMV promoter. In some embodiments, the CMV promoter comprises the nucleic acid sequence of SEQ ID NO: 3. In some embodiments, the construct is a viral vector or a plasmid. In some embodiments, the construct is an AAV vector. In some embodiments, the target RNA is an RNA selected from the group consisting of a pre-messenger RNA, a messenger RNA, a ribosomal RNA, a transfer RNA, a long non-coding RNA and a small RNA. Also provided herein are host cells comprising the construct as described in this aspect. Also provided herein are kits for editing a target RNA in a host cell comprising the construct as described in this aspect.

It is to be understood that one, some, or all of the properties of the various embodiments described herein may be combined to form other embodiments of the present application. These and other embodiments of the present application are further described by the detailed description that follows.

BRIEF DESCRIPTION OF THE DRAWINGS

FIG. 2A shows a schematic of arRNA-expressing plasmid. The 151-nt arRNA targeting fluorescence Reporter-1 was expressed under human U6 promoter. FIG. 2B shows the FACS results of sno-arRNA or arRNA transfection results. The sno-arRNA$_{151}$, arRNA$_{151}$, sno-Ctrl RNA$_{151}$ or Ctrl RNA$_{151}$ was transfected into HEK293T cells along with Reporter-expressing plasmids. FIG. 2C shows quantification of the FACS results in FIG. 2B.

FIG. 3A shows the quantificational FACS results of hU6-derived sno-arRNA or arRNA at different time point. FIG. 3B shows the quantificational FACS results of CMV or hU6 derived arRNA at different time point. FIG. 3C shows the quantificational FACS results of CMV or hU6 derived sno-arRNA at different time point.

FIGS. 4A-4E depict editing efficacy using circular arRNA in the LEAPER system FIG. 4A shows a schematic of circular arRNA expression. Circular arRNA transcript was flanked by 5' and 3' ligation sequence, which were respectively flanked by 5'-Twister P3 U2A and 3'-Twister P1 ribozymes undergoing self-cleavage. The resulting RNA ends were recognized by RtcB for ligation. FIG. 4B shows a schematic of the Reporter-1 and Reporter-3, mCherry and EGFP genes were linked by sequences containing 3× (for Reporter-1) or 1× (for Reporter-3) GGGGS-coding region and an in-frame UAG stop codon. The reporter expressed cells only produced mCherry protein, while targeted editing on the UAG stop codon of the reporter transcript could convert the UAG to UIG and thus to permit the downstream EGFP expression. FIG. 4C shows results of an experiment, in which HEK293T cells stably expressing the Reporter-1 seeded in 12-well plates ($3\times10^5$ cells/well) were transfected with the 1 µg of circular $arRNA_{71}$, circular $arRNA_{25\text{-}71\text{-}25}$, circular $arRNA_{50\text{-}71\text{-}50}$, circular $arRNA_{111}$, circular $arRNA_{25\text{-}111\text{-}25}$, circular $arRNA_{50\text{-}111\text{-}50}$, circular Ctrl $RNA_{123}$ (non-target sequence), $arRNA_{71}$, Ctrl $RNA_{71}$, $arRNA_{111}$, Ctrl $RNA_{111}$ expressing plasmid respectively. FACS analyses were performed 2 days and 7 days after transfection. The ratios of EGFP+ cells were normalized by transfection efficiency. FIG. 4D shows results of an experiment, in which HEK293T cells stably expressing the Reporter-3 seeded in 12-well plates ($3\times10^5$ cells/well) were transfected with the 1 µg of Ctrl $RNA_{151}$ (circular), 31-, 51-, 71-, 91-, 111-, 131-, 151-nt circular arRNA expressing plasmid respectively. FACS analyses were performed 2 days post transfection. The ratios of EGFP+ cells were normalized by transfection efficiency. FIG. 4E shows results of an experiment, in which HeLa and A549 cells seeded in 12-well plates ($2\times10^5$ cells/well) were co-transfected with the 0.5 µg of reporter-1 expressing plasmid and the 0.5 µg of circular $arRNA_{111}$ expressing plasmid respectively. FACS analyses were performed 2 days post transfection. The ratios of EGFP+ cells were normalized by transfection efficiency.

DETAILED DESCRIPTION

Figure 1:
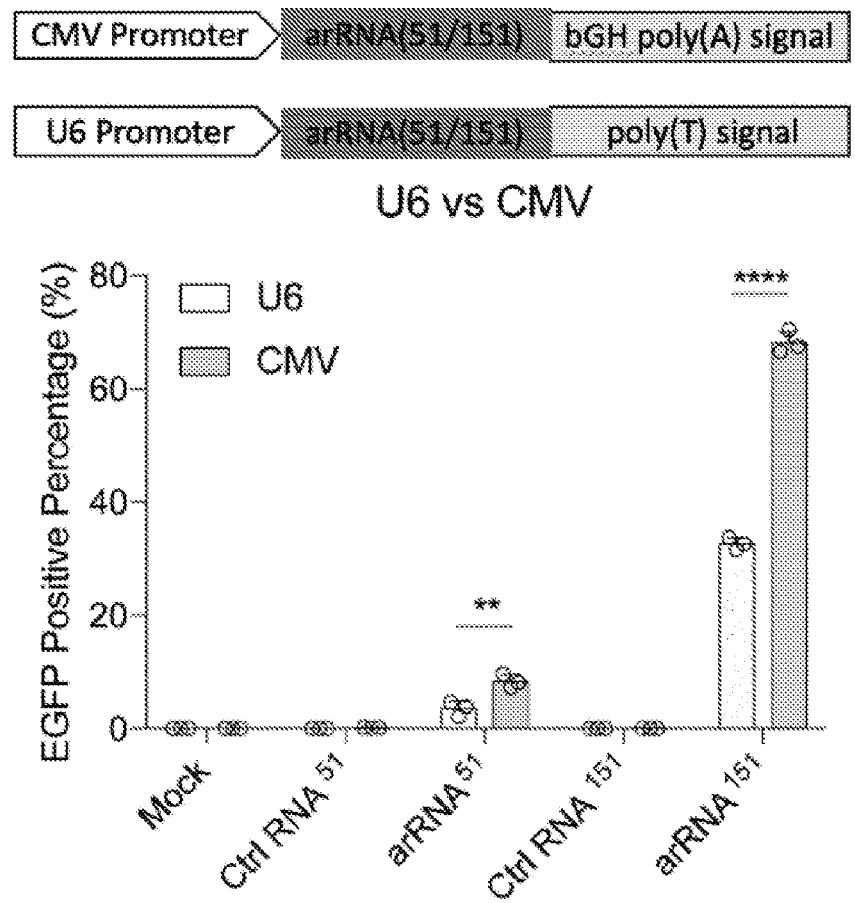
FIG. 1 depicts FACS analysis after transfection of a plasmid expressing arRNA driven by a pol II promoter (CMV) and a plasmid expressing arRNA driven by a Pol III promoter (U6) for 48 hours. The EGFP positive percentages were normalized by transfection efficiency, which was determined by mCherry positive ratio. Data are mean values±s.d. (n=3).

The present description provides RNA editing methods (referred herein as the "improved LEAPER" methods) and specially designed RNAs, referred herein as deaminase-recruiting RNAs ("dRNAs") or ADAR-recruiting RNAs ("arRNAs") or constructs comprising nucleic acids encoding these dRNAs, to edit target RNAs in a host cell.

"LEAPER" (Leveraging Endogenous ADAR for Programmable Editing on RNA) have been previously developed by inventors of the present application, which leverages endogenous ADAR to edit target RNA by utilizing dRNAs, also referred to as "arRNAs." LEAPER method was described in PCT/CN2018/110105 and PCT/CN2020/084922, which are incorporated herein by reference in their entirety. Specifically, a targeting RNA that is partially complementary to the target transcript was used to recruit native ADAR1 or ADAR2 to change adenosine to inosine at a specific site in a target RNA. As such, RNA editing can be achieved in certain systems without ectopic or overexpression of the ADAR proteins in the host cell.

The present application provided improved LEAPER methods that allow for increased efficiency for RNA editing, for example by increasing the level of the dRNA in target cells. In one aspect, the improved LEAPER method involves use of circular dRNA or dRNA capable of forming a circular RNA. In another aspect, the improved LEAPER method involves use of dRNA comprising one or more small nucleolar RNA (snoRNA) linked to the 3' or 5' of the targeting RNA sequence. In another aspect, the improved LEAPER method involves dRNAs placed under the control of a polymerase II promoter ("Pol II promoter"). We demonstrated that, compared to LEAPER methods, the improved LEAPER methods significantly increased the editing efficiency of the dRNA. Without being bound by theory, it is believed that an increase in stability or amount of the dRNA used in the improved LEAPER methods contributed to such improvement in RNA editing efficiency.

Thus, the present application in one aspect provides a method of editing a target RNA by one or more of the improved LEAPER methods.

In another aspect, there are provided dRNAs and constructs used for the improved LEAPER methods.

Also provided herein are methods and compositions for treating or preventing a disease or condition in an individual using the RNA editing methods.

I. Definitions

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to particular method steps, reagents, or conditions are specifically embraced by the present disclosure and are disclosed herein just as if each and every combination was individually and explicitly disclosed.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The terms "deaminase-recruiting RNA," "dRNA," "ADAR-recruiting RNA" and "arRNA" are used herein interchangeably to refer to an engineered RNA capable of recruiting an ADAR to deaminate a target adenosine in an RNA.

The terms "polynucleotide," "nucleotide sequence" and "nucleic acid" are used interchangeably. They refer to a polymeric form of nucleotides of any length, either deoxyribonucleotides or ribonucleotides, or analogs thereof.

The terms "adenine," "guanine," "cytosine," "thymine," "uracil" and "hypoxanthine" as used herein refer to the nucleobases as such. The terms "adenosine," "guanosine," "cytidine," "thymidine," "uridine" and "inosine," refer to the nucleobases linked to the ribose or deoxyribose sugar moiety. The term "nucleoside" refers to the nucleobase linked to the ribose or deoxyribose. The term "nucleotide" refers to the respective nucleobase-ribosyl-phosphate or nucleobase-deoxyribosyl-phosphate. Sometimes the terms adenosine and adenine (with the abbreviation, "A"), guanosine and guanine (with the abbreviation, "G"), cytosine and cytidine (with the abbreviation, "C"), uracil and uridine (with the abbreviation, "U"), thymine and thymidine (with the abbreviation, "T"), inosine and hypo-xanthine (with the abbreviation, "I"), are used interchangeably to refer to the corresponding nucleobase, nucleoside or nucleotide. Sometimes the terms nucleobase, nucleoside and nucleotide are used interchangeably, unless the context clearly requires differently.

The term "introducing" or "introduction" used herein means delivering one or more polynucleotides, such as dRNAs or one or more constructs including vectors as described herein, one or more transcripts thereof, to a host cell. The invention serves as a basic platform for enabling targeted editing of RNA, for example, pre-messenger RNA, a messenger RNA, a ribosomal RNA, a transfer RNA, a long non-coding RNA and a small RNA (such as miRNA). The methods of the present application can employ many delivery systems, including but not limited to, viral, liposome, electroporation, microinjection and conjugation, to achieve the introduction of the dRNA or construct as described herein into a host cell. Conventional viral and non-viral based gene transfer methods can be used to introduce nucleic acids into mammalian cells or target tissues. Such methods can be used to administer nucleic acids encoding dRNA of the present application to cells in culture, or in a host organism. Non-viral vector delivery systems include DNA plasmids, RNA (e.g, a transcript of a construct described herein), naked nucleic acid, and nucleic acid complexed with a delivery vehicle, such as a liposome. Viral vector delivery systems include DNA and RNA viruses, which have either episomal or integrated genomes for delivery to the host cell.

In the context of the present application, "target RNA" refers to an RNA sequence to which a deaminase-recruiting RNA sequence is designed to have perfect complementarity or substantial complementarity, and hybridization between the target sequence and the dRNA forms a double stranded RNA (dsRNA) region containing a target adenosine, which recruits an adenosine deaminase acting on RNA (ADAR) that deaminates the target adenosine. In some embodiments, the ADAR is naturally present in a host cell, such as a eukaryotic cell (such as a mammalian cell, e.g., a human cell). In some embodiments, the ADAR is introduced into the host cell.

As used herein, "complementarity" refers to the ability of a nucleic acid to form hydrogen bond(s) with another nucleic acid by traditional Watson-Crick base-pairing. A percent complementarity indicates the percentage of residues in a nucleic acid molecule which can form hydrogen bonds (i.e, Watson-Crick base pairing) with a second nucleic acid (e.g., about 5, 6, 7, 8, 9, 10 out of 10, being about 50%, 60%, 70%, 80%, 90%, and 100% complementary respectively). "Perfectly complementary" means that all the contiguous residues of a nucleic acid sequence form hydrogen bonds with the same number of contiguous residues in a second nucleic acid sequence. "Substantially complementary" as used herein refers to a degree of complementarity that is at least about any one of 70%, 75%, 80%, 85%, 90%, 95%, 97%, 98%, 99%, or 100% over a region of about 40, 50, 60, 70, 80, 100, 150, 200, 250 or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology—Hybridization With Nucleic Acid Probes Part I, Second Chapter "Overview of principles of hybridization and the strategy of nucleic acid probe assay," Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. A sequence capable of hybridizing with a given sequence is referred to as the "complement" of the given sequence.

As used herein, the terms "including," "containing," and "comprising" are used in their open, non-limiting sense. It is also understood that aspects and embodiments of the present application described herein may include "consisting" and/or "consisting essentially of" aspects and embodiments.

It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

As used herein, a "carrier" includes pharmaceutically acceptable carriers, excipients, or stabilizers that are non-toxic to the cell or mammal being exposed thereto at the dosages and concentrations employed. Often the physiologically acceptable carrier is an aqueous pH buffered solution. Non-limiting examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

As used herein, the term "effective amount" or "therapeutically effective amount" of a substance is at least the minimum concentration required to effect a measurable improvement or prevention of a particular disorder. An effective amount herein may vary according to factors such as the disease state, age, sex, and weight of the patient, and the ability of the substance to elicit a desired response in the individual. An effective amount is also one in which any toxic or detrimental effects of the treatment are outweighed by the therapeutically beneficial effects. In reference to cancer, an effective amount comprises an amount sufficient to cause a tumor to shrink and/or to decrease the growth rate of the tumor (such as to suppress tumor growth) or to prevent or delay other unwanted cell proliferation in cancer. In some embodiments, an effective amount is an amount sufficient to delay development of cancer. In some embodiments, an effective amount is an amount sufficient to prevent or delay recurrence. In some embodiments, an effective amount is an amount sufficient to reduce recurrence rate in the individual. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; (vii) reduce recurrence rate of tumor, and/or (viii) relieve to some extent one or more of the symptoms associated with the cancer. An effective amount can be administered in one or more administrations. For purposes of this disclosure, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

A "host cell" as described herein refers to any cell type that can be used as a host cell provided it can be modified as described herein. For example, the host cell may be a host cell with endogenously expressed adenosine deaminase acting on RNA (ADAR), or may be a host cell into which an adenosine deaminase acting on RNA (ADAR) is introduced by a known method in the art. For example, the host cell may be a prokaryotic cell, a eukaryotic cell or a plant cell. In some embodiments, the host cell is derived from a pre-established cell line, such as mammalian cell lines including human cell lines or non-human cell lines. In some embodiments, the host cell is derived from an individual, such as a human individual.

A "recombinant AAV vector (rAAV vector)" refers to a polynucleotide vector comprising one or more heterologous sequences (i.e., nucleic acid sequence not of AAV origin) that are flanked by at least one, and in embodiments two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g, in a chromosome or in another vector such as a plasmid used for cloning or transfection), then the rAAV vector may be referred to as a "pro-vector" which can be "rescued" by replication and encapsidation in the presence of AAV packaging functions and suitable helper functions. An rAAV vector can be in any of a number of forms, including, but not limited to, plasmids, linear artificial chromosomes complexed with lipids, encapsulated within liposomes, and encapsidated in a viral particle, particularly an AAV particle. A rAAV vector can be packaged into an AAV virus capsid to generate a "recombinant adeno-associated viral particle (rAAV particle)".

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

A "subject", "patient" or "individual" includes a mammal, such as a human or other animal, and typically is human. In some embodiments, the subject, e.g., patient, to whom the therapeutic agents and compositions are administered, is a mammal, typically a primate, such as a human. In son embodiments, the primate is a monkey or an ape. The subject can be male or female and can be any suitable age, including infant, juvenile, adolescent, adult, and geriatric subjects. In some embodiments, the subject is a non-primate mammal, such as a rodent, a dog, a cat, a farm animal, such as a cow or a horse, etc.

As used herein, the term "treatment" refers to clinical intervention designed to have beneficial and desired effects to the natural course of the individual or cell being treated during the course of clinical pathology. For the purpose of this disclosure, desirable effects of treatment include, without limitation, decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of for destroying) cancerous cells, increasing cancer cell-killing, decreasing symptoms resulting from the disease, preventing spread of diseases, preventing recurrence of disease, increasing the quality of life of those suffering from the disease, decreasing the dose of other medications required to treat the disease, delaying the progression of the disease, and/or prolonging survival of individuals.

II. Methods of RNA Editing

Provided herein are methods for editing a target RNA in a host cell, comprising introducing a deaminase-recruiting RNA (dRNA) or a construct comprising a nucleic acid encoding the dRNA into the host cell (e.g., eukaryotic cell), wherein: (1) the dRNA comprises a targeting RNA sequence that is at least partially complementary to the target RNA and (2) the dRNA is capable of recruiting an adenosine deaminase acting on RNA (ADAR).

Circular dRNAs

In one aspect, provided herein are methods for editing a target RNA in a host cell, comprising introducing a deaminase-recruiting RNA (dRNA) or a construct comprising a nucleic acid encoding the dRNA into the host cell (e.g., eukaryotic cell), wherein: (1) the dRNA comprises a targeting RNA sequence that is at least partially complementary to the target RNA, (2) the dRNA is capable of recruiting an adenosine deaminase acting on RNA (ADAR), and (3) the dRNA is a circular RNA or capable of forming a circular RNA.

In some embodiments, provided herein are methods for editing a target RNA in a host cell, comprising introducing a deaminase-recruiting RNA (dRNA) or a construct comprising a nucleic acid encoding the dRNA into the host cell, wherein: (1) the dRNA comprises a targeting RNA sequence that is at least partially complementary to the target RNA, (2) the dRNA is capable of recruiting an endogenously expressed ADAR of the host cell to deaminate a target adenosine residue in the target RNA, and (3) the dRNA is a circular RNA or capable of forming a circular RNA. In some embodiments, the method does not comprise introducing any protein or construct comprising a nucleic acid encoding a protein (e.g., Cas, ADAR or a fusion protein of ADAR and Cas) to the host cell.

In some embodiments, provided herein are methods for editing a target RNA in a host cell, comprising introducing a deaminase-recruiting RNA (dRNA) or a construct comprising a nucleic acid encoding the dRNA into the host cell, wherein: (1) the dRNA comprises a targeting RNA sequence that is at least partially complementary to the target RNA, (2) the dRNA is capable of recruiting an endogenously expressed ADAR of the host cell to deaminate a target adenosine residue in the target RNA, and (3) the dRNA is a circular RNA. In some embodiments, the method does not comprise introducing any protein or construct comprising a nucleic acid encoding a protein (e.g., Cas, ADAR or a fusion protein of ADAR and Cas) to the host cell.

In some embodiments, provided herein are methods for editing a target RNA in a host cell, comprising introducing a deaminase-recruiting RNA (dRNA) or a construct comprising a nucleic acid encoding the dRNA into the host cell, wherein: (1) the dRNA comprises a targeting RNA sequence that is at least partially complementary to the target RNA, (2) the dRNA is capable of recruiting an endogenously expressed ADAR of the host cell to deaminate a target adenosine residue in the target RNA, and (3) the dRNA is a linear RNA capable of forming a circular RNA. In some embodiments, the method does not comprise introducing any protein or construct comprising a nucleic acid encoding a protein (e.g., Cas, ADAR or a fusion protein of ADAR and Cas) to the host cell.

In some embodiments, provided herein are methods for editing a target RNA in a host cell, comprising introducing a deaminase-recruiting RNA (dRNA) or a construct comprising a nucleic acid encoding the dRNA into the host cell and an ADAR or a construct comprising a nucleic acid encoding the ADAR into the host cell, wherein: (1) the dRNA comprises a targeting RNA sequence that is at least partially complementary to the target RNA, (2) the dRNA is capable of recruiting the ADAR to deaminate a target adenosine ("A") residue in the target RNA, and (3) the dRNA is a circular RNA or capable of forming a circular RNA. In some embodiments, the ADAR is an endogenously encoded ADAR of the host cell, wherein introduction of the ADAR comprises over-expressing the ADAR in the host cell. In some embodiments, the ADAR is exogenous to the host cell. In some embodiments, the construct comprising a nucleic acid encoding the ADAR is a vector, such as a plasmid, or a viral vector (e.g., an AAV or a lentiviral vector).

In one aspect, the present application provides a method for editing a plurality of target RNAs (e.g., at least about 2, 3, 4, 5, 10, 20, 50, 100, 1000 or more) in host cells by introducing a plurality of the dRNAs, or one or more constructs encoding the dRNAs, into the host cells.

10. The method of embodiment 9, wherein the construct further comprises a 3' twister ribozyme sequence linked to the 3' end of the nucleic acid encoding the dRNA and a 5' twister ribozyme sequence linked to the 5' end of the nucleic acid encoding the dRNA.

In some embodiments, the dRNA is introduced by a construct comprising a nucleic acid encoding the dRNA. In some embodiments, the construct further comprises a 3' twister ribozyme sequence linked to the 3' end of the nucleic acid encoding the dRNA. In some embodiments, the construct further comprises a 5' twister ribozyme sequence linked to the 5' end of the nucleic acid encoding the dRNA. In some embodiments, the construct further comprises a 3' twister ribozyme sequence linked to the 3' end of the nucleic acid encoding the dRNA and a 5' twister ribozyme sequence linked to the 5' end of the nucleic acid encoding the dRNA. In some embodiments, the 3' twister sequence is twister P3 U2A and the 5' twister sequence is twister P1. In some embodiments, wherein the 5' twister sequence is twister P3 U2A and the 3' twister sequence is twister P1. In some embodiments, the dRNA undergoes autocatalytic cleavage. In some embodiments, the catalyzed dRNA product comprises a 5'-hydroxyl group and a 2',3'-cyclic phosphate al the 3' terminus. In some embodiments, the catalyzed dRNA product is ligated by ubiquitous endogenous RNA ligase (e.g., RNA ligase RtcB). In some embodiments, the construct is a plasmid or a viral vector.

In some embodiments, the dRNA transcript is also flanked by a 5' and/or 3' ligation sequences, which are then flanked by the 5'-Twister ribozyme and/or 3'-Twister ribozymes, respectively. In some embodiments, the dRNA comprises a 3' ligation sequence. In some embodiments, the dRNA comprises a 5' ligation sequence, in some embodiments, the dRNA further comprises a 3' ligation sequence and a 5' ligation sequence. In some embodiments, the 3' ligation sequence and the 5' ligation sequence are at least partially complementary to each other. In some embodiments, the 3' ligation sequence and the 5' ligation sequence are at least about 50%, at least about 55%, at least about 60%, at least about 65%, at least about 70%, at least about 75%, at least about 80%, at least about 85%, at least about 90%, at least about 95%, at least about 96%, at least about 97%, at least about 98% or at least about 99% complementary to each other. In some embodiments, the 3' ligation sequence and the 5' ligation sequence are fully complementary to each other.

In some embodiments, the 3' ligation sequence and the 5' ligation sequence are independently at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides or at least about 100 nucleotides in length. In some embodiments, the 3' ligation sequence and the 5' ligation sequence are independently about 20-30 nucleotides, about 30-40 nucleotides, about 40-50 nucleotides, about 50-60 nucleotides, about 60-70 nucleotides, about 70-80 nucleotides, about 80-90 nucleotides, about 90-100 nucleotides, about 100-125 nucleotides, about 125-150 nucleotides, about 20-50 nucleotides, about 50-100 nucleotides or about 100-150 nucleotides in length.

In some embodiments, the dRNA is circularized by an RNA ligase. Non-limiting examples of RNA ligase include: RtcB, T4 RNA Ligase 1, T4 RNA Ligase 2, Rnl3 and Trl1. In some embodiments, the RNA ligase is expressed endogenously in the host cell. In some embodiments, the RNA ligase is RNA ligase RtcB. In some embodiments, the method further comprises introducing an RNA ligase (e.g., RtcB) into the host cell.

In some embodiments, the dRNA is circularized before being introduced to the host cell. In some embodiments, the dRNA is chemically synthesized. In some embodiments, the dRNA is circularized through in vitro enzymatic ligation (e.g., using RNA or DNA ligase) or chemical ligation (e.g., using cyanogen bromide or a similar condensing agent).

dRNA Having One or Two snoRNA Ends

In another aspect, provided herein are methods for editing a target RNA in a host cell (e.g., eukaryotic cell), comprising introducing a deaminase-recruiting RNA (dRNA) or a construct comprising a nucleic acid encoding the dRNA into the host cell, wherein the dRNA comprises: (1) a targeting RNA sequence that is at least partially complementary to the target RNA and (2) a small nucleolar RNA (snoRNA) sequence linked to the 3' and/or 5' ends of the targeting RNA sequence; and wherein the dRNA is capable of recruiting an adenosine deaminase acting on RNA (ADAR).

In some embodiments, provided herein are methods for editing a target RNA in a host cell (e.g., eukaryotic cell), comprising introducing a deaminase-recruiting RNA (dRNA) or a construct comprising a nucleic acid encoding the dRNA into the host cell, wherein the dRNA comprises: (1) a targeting RNA sequence that is at least partially complementary to the target RNA and (2) a small nucleolar RNA (snoRNA) sequence linked to the 3' and/or 5' ends of the targeting RNA sequence; and wherein the dRNA is capable of recruiting an endogenously expressed adenosine deaminase acting on RNA (ADAR) of the host cell to deaminate a target adenosine residue in the target RNA. In some embodiments, the method does not comprise introducing any protein or construct comprising a nucleic acid encoding a protein (e.g., Cas, ADAR or a fusion protein of ADAR and Cas) to the host cell.

In some embodiments, provided herein are methods for editing a target RNA in a host cell (e.g., eukaryotic cell), comprising introducing (a) a deaminase-recruiting RNA (dRNA) or a construct comprising a nucleic acid encoding the dRNA and (b) an ADAR or a construct comprising a nucleic acid encoding the ADAR into the host cell, wherein the dRNA comprises: (1) a targeting RNA sequence that is at least partially complementary to the target RNA and (2) a small nucleolar RNA (snoRNA) sequence linked to the 3' and/or 5' ends of the targeting RNA sequence; and wherein the dRNA is capable of recruiting the ADAR to deaminate a target adenosine residue in the target RNA. In some embodiments, the ADAR is an endogenously encoded ADAR of the host cell, wherein introduction of the ADAR comprises over-expressing the ADAR in the host cell. In some embodiments, the ADAR is exogenous to the host cell. In some embodiments, the construct comprising a nucleic acid encoding the ADAR is a vector, such as a plasmid, or a viral vector (e.g., an AAV or a lentiviral vector).

In one aspect, the present application provides a method for editing a plurality of target RNAs (e.g., at least about 2, 3, 4, 5, 10, 20, 50, 100, 1000 or more) in host cells by introducing a plurality of the dRNAs, or one or more constructs encoding the dRNAs, into the host cells.

Small nucleolar RNAs (snoRNAs) are small non-coding RNA molecules that are known to guide chemical modifications of other RNAs such as ribosomal RNAs, transfer RNAs. and small nuclear RNAs. There are two major groups of snoRNAs according to their specific secondary structure features: box C/D and box H/ACA. Both structural features of snoRNAs enable them binding to corresponding RNA binding proteins (RBPs) along with accessory proteins, forming functional small nucleolar ribonucleoprotein (snoRNP) complexes. Box C/D snoRNAs are believed to be associated with methylation, while H/ACA box snoRNAs are believed to be associated with pseudouridylation. Other families of snoRNAs include, for example, composite H/ACA and CID box snoRNA and orphan snoRNAs. The snoRNA sequence described herein can comprise a naturally-occurring snoRNA, a portion thereof, or a variant thereof.

In some embodiments, the dRNA comprises a snoRNA sequence linked to the 5' end of the targeting RNA sequence ("5' snoRNA sequence"). In some embodiments, the dRNA comprises a snoRNA sequence linked to the 3' end of the targeting RNA sequence ("3' snoRNA sequence"). In some embodiments, the dRNA comprises a snoRNA sequence linked to the 5' end of the targeting RNA sequence ("5' snoRNA sequence") and a snoRNA sequence linked to the 3' end of the targeting RNA sequence ("3' snoRNA sequence"). In some embodiments, the snoRNA sequence is at least about 50 nucleotides, at least about 60 nucleotides, at least about 70 nucleotides, at least about 80 nucleotides, at least about 90 nucleotides, at least about 100 nucleotides, at least about 110 nucleotides, at least about 120 nucleotides, at least about 130 nucleotides, at least about 140 nucleotides, at least about 150 nucleotides, at least about 160 nucleotides, at least about 170 nucleotides, at least about 180 nucleotides, at least about 190 nucleotides or at least about 200 nucleotides in length. In some embodiments, the snoRNA sequence is about 50-75 nucleotides, about 75-100 nucleotides, about 100-125 nucleotides, about 125-150 nucleotides, about 150-175 nucleotides, about 175-200 nucleotides, about 50-100 nucleotides, about 100-150 nucleotides, about 150-200 nucleotides, about 125-175 nucleotides, or about 100-200 nucleotides in length.

In some embodiments, the 3' snoRNA sequence comprises the nucleic acid sequence of SEQ ID NO: 1 (5'-AAGATTGTGTGTGGATCGATGATGACTTC-CATATATACATTCCTTGGAAAGCTGAAC AAAATGAGTGAAAACTCTATACCGTCAT-TCTCGTCGAACTGAGGTCCAGCACATTAC TCCAACAG-3'). In some embodiments, the 5' snoRNA sequence comprises the nucleic acid sequence of SEQ ID NO: 2 (5'-GAGTGAGATCTTGGACCAATGATGACTTC-CATACATGCATTCCTTGGAAAGCTGAAC AAAAT-GAGTGGGAACTCTGTACTATCATCTTAGTTGAACT-GAGGTCCACCGGGGCT AA-3'). In some embodiments, the snoRNA sequence is a C/D Box snoRNA sequence. In some embodiments, the snoRNA sequence is an I/ACA Box snoRNA sequence. In some embodiments, the snoRNA sequence is a composite C/D Box and H/ACA Box snoRNA sequence. In some embodiments, the snoRNA sequence is an orphan snoRNA sequence.

Constructs with Pol II Promoter

In another aspect, provided herein are methods for editing a target RNA in a host cell, comprising introducing a construct comprising a nucleic acid encoding a deaminase-recruiting RNA (dRNA) into the host cell, wherein: (1) the dRNA comprises a targeting RNA sequence that is at least partially complementary to the target RNA, (2) the dRNA is capable of recruiting an adenosine deaminase acting on RNA (ADAR), and (3) the construct comprises a polymerase II promoter ("Pol II promoter") operably linked to the nucleic acid encoding the dRNA.

In some embodiments, there are provided methods for editing a target RNA in a host cell, comprising introducing a construct comprising a nucleic acid encoding a deaminase-recruiting RNA (dRNA) into the host cell, wherein: (1) the dRNA comprises a targeting RNA sequence that is at least partially complementary to the target RNA, (2) the dRNA is capable of recruiting an endogenously expressed adenosine deaminase acting on RNA (ADAR) of the host cell to deaminate a target adenosine residue in the target RNA, and (3) the construct comprises a polymerase II promoter ("Pol II promoter") operably linked to the nucleic acid encoding the dRNA. In some embodiments, the method does not comprise introducing any protein or construct comprising a nucleic acid encoding a protein (e.g., Cas, ADAR or a fusion protein of ADAR and Cas) to the host cell.

In some embodiments, provided herein are methods for editing a target RNA in a host cell, comprising introducing (a) a construct comprising a nucleic acid encoding a deaminase-recruiting RNA (dRNA) and (h) an ADAR or a construct comprising a nucleic acid encoding the ADAR into the host cell, wherein: (1) the dRNA comprises a targeting RNA sequence that is at least partially complementary to the target RNA, (2) the dRNA is capable of recruiting the adenosine deaminase acting on RNA (ADAR) to deaminate a target adenosine residue in the target RNA, and (3) the construct comprises a polymerase II promoter ("Pol II promoter") operably linked to the nucleic acid encoding the dRNA. In some embodiments, the ADAR is an endogenously encoded ADAR of the host cell, wherein introduction of the ADAR comprises over-expressing the ADAR in the host cell. In some embodiments, the ADAR is exogenous to the host cell. In some embodiments, the construct comprising a nucleic acid encoding the ADAR is a vector, such as a plasmid, or a viral vector (e.g., an AAV or a lentiviral vector).

In one aspect, the present application provides a method for editing a plurality of target RNAs (e.g., at least about 2, 3, 4, 5, 10, 20, 50, 100, 1000 or more) in host cells by introducing a plurality of the dRNAs, or one or more constructs encoding the dRNAs, into the host cells. In some embodiments, one Pol II promoter (e.g., CMV) is driving expression of two or more dRNAs.

Non-limiting examples of Pol II promoters include: CMV, SV40, EF-1α, CAG and RSV. In some embodiments, the Pol II promoter is a CMV promoter. In some embodiments, the CMV promoter comprises the nucleic acid sequence of SEQ ID NO: 3 (5'-CGTTACATAACTTACGGTAAATGGCCCGCCTGGCTGACCGCC-CAACGACCCCCGCCC ATTGACGT-CAATAATGACGTATGTTCCCATAGTAACGCCAATA-GGGACTTTCCATTG ACGTCAATGGGTGGAGTATT-TACGGTAAACTGCCCACTTGGCAGTACAT-CAAGTGTA TCATATGCCAAGTACGCCCCCTAT-TGACGTCAATGACGGTAAATGGCCCGCCTGGCA TTATGCCCAGTACATGACCTTATGGGACTTTCC-TACTTGGCAGTACATCTACGTATTA GTCATCGCTAT-TACCATGGTGATGCGGTTTTGGCAGTACAT-CAATGGGCGTGGATAG CGGTTTGACTCACGGGGATTTCCAAGTCTCCACCC-CATTGACGTCAATGGGAGTTTG TTTTGGCAC-CAAAATCAACGGGACTTTC-CAAAATGTCGTAACAACTCCGCCCCATTG ACGCAAATGGGCGGTAGGCGTGTACGGTGG-GAGGTCTATATAAGCAGAGCT-3').

In some embodiments according to any one of the methods described herein, the host cell is a prokaryotic cell. In some embodiments, the host cell is a eukaryotic cell. In some embodiments, the host cell is a mammalian cell. In some embodiments, the host cell is a human cell. In some embodiments, the host cell is a murine cell. In some embodiments, the host cell is a plant cell or a fungal cell.

In some embodiments according to any one of the methods or use described herein, the host cell is a cell line, such as HEK293T, HT29, A549, HepG2, RD, SF268, SW13 and HeLa cell. In some embodiments, the host cell is a primary cell, such as fibroblast, epithelial, or immune cell. In some embodiments, the host cell is a T cell. In some embodiments, the host cell is a post-mitosis cell. In some embodiments, the host cell is a cell of the central nervous system (CNS), such as a brain cell, e.g., a cerebellum cell.

In some embodiments according to any one of the methods described herein, the ADAR is endogenous to the host cell. In some embodiments, the adenosine deaminase acting on RNA (ADAR) is naturally or endogenously present in the host cell, for example, naturally or endogenously present in the eukaryotic cell. In some embodiments, the ADAR is endogenously expressed by the host cell. In certain embodiments, the ADAR is exogenously introduced into the host cell. In some embodiments, the ADAR is ADAR1 and/or ADAR2. In certain embodiments, the ADAR is one or more ADARs selected from the group consisting of hADAR1, hADAR2, mouse ADAR1 and ADAR2. In some embodiments, the ADAR is ADAR1, such as p110 isoform of ADAR1 ("ADAR1$^{p110}$") and/or p150 isoform of ADAR1 ("ADAR1$^{p150}$"). In some embodiments, the ADAR is ADAR2. In some embodiments, the ADAR is an ADAR2 expressed by the host cell, e.g., ADAR2 expressed by cerebellum cells.

In some embodiments, the ADAR is an ADAR exogenous to the host cell. In some embodiments, the ADAR is a hyperactive mutant of a naturally occurring ADAR. In some embodiments, the ADAR is ADAR1 comprising an E1008Q mutation. In some embodiments, the ADAR is not a fusion protein comprising a binding domain. In some embodiments, the ADAR does not comprise an engineered double-strand nucleic acid-binding domain. In some embodiments, the ADAR does not comprise a MCP domain that binds to MS2 hairpin that is fused to the complementary RNA sequence in the dRNA. In some embodiments, the ADAR does not comprise a DSB.

In some embodiments according to any one of the methods described herein, the host cell has high expression level of ADAR1 (such as ADAR1$^{p110}$ and/or ADAR1$^{p150}$), e.g., at least about any one of 10%, 20%, 50%, 100%, 2×, 3×, 5×, or more relative to the protein expression level of β-tubulin. In some embodiments, the host cell has high expression level of ADAR2, e.g., at least about any one of 10%, 20%, 50%, 100%, 2×, 3×, 5×, or more relative to the protein expression level of β-tubulin. In some embodiments, the host cell has low expression level of ADAR3, e.g., no more than about any one of 5×, 3×, 2×, 100%, 50%, 20% or less relative to the protein expression level of β-tubulin.

In certain embodiments according to any one of the methods described herein, the dRNA comprises at least about any one of 40, 45, 50, 55, 60, 65, 70, 75, 80, 90, 100, 110, 120, 130, 140, 150, 160, 170, 180, 190, 200, 210, 220, 230, 240, or 250 nucleotides. In certain embodiments according to any one of the methods described herein, the dRNA comprises no more than about any one of 40, 45, 50, 55, 60, 65, 70, 75, 80, 90, 100, 110, 120, 130, 140, 150, 160, 170, 180, 190, 200, 210, 220, 230, 240, or 250 nucleotides. In certain embodiments, the dRNA is about any one of 40-260, 45-250, 50-240, 60-230, 65-220, 70-220, 70-210, 70-200, 70-190, 70-180, 70-170, 70-160, 70-150, 70-140, 70-130, 70-120, 70-110, 70-100, 70-90, 70-80, 75-200, 80-190, 85-180, 90-170, 95-160, 100-200, 100-150, 100-175, 110-200, 110-175, 110-150, or 105-140 nucleotides in length.

In some embodiments according to any one of the methods or use described herein, the dRNA does not comprise an ADAR-recruiting domain. "ADAR-recruiting domain" can be a nucleotide sequence or structure that binds at high affinity to ADAR, or a nucleotide sequence that binds to a binding partner fused to ADAR in an engineered ADAR construct. Exemplary ADAR-recruiting domains include, but are not limited to, GluR-2, GluR-B (R/G), GluR-B (Q/R), GluR-6 (R/G), 5HT2C, and FlnA (Q/R) domain; see, for example, Wahlstedt, Helene, and Marie, "Site-selective versus promiscuous A-to-I editing." Wiley Interdisciplinary Reviews: RNA 2.6 (2011): 761-771, which is incorporated herein by reference in its entirety. In some embodiments, the dRNA does not comprise a double-stranded portion. In some embodiments, the dRNA does not comprise a hairpin, such as MS2 stem loop. In some embodiments, the dRNA is single stranded. In some embodiments, the dRNA does not comprise a DSB-binding domain. In some embodiments, the dRNA consists of (or consists essentially of) the complementary RNA sequence.

In some embodiments according to any one of the methods described herein, the dRNA does not comprise chemical modifications. In some embodiments, the dRNA does not comprise a chemically modified nucleotide, such as 2'-O-methyl nucleotide or a nucleotide having a phosphorothioate linkage. In some embodiments, the dRNA comprises 2'-O-methyl and phosphorothioate linkage modifications only at the first three and last three residues. In some embodiments, the dRNA is not an antisense oligonucleotide (ASO).

The dRNAs described herein comprise a targeting RNA sequence that is at least partially complementary to the target RNA. In certain embodiments according to any one of the methods described herein, the targeting RNA sequence in the dRNA comprises at least about any one of 40, 45, 50, 55, 60, 65, 70, 75, 80, 90, 100, 110, 120, 130, 140, 150, 160, 170, 180, 190, 200, 210, 220, 230, 240, or 250 nucleotides. In certain embodiments according to any one of the methods described herein, the targeting RNA sequence in the dRNA comprises no more than about any one of 40, 45, 50, 55, 60, 65, 70, 75, 80, 90, 100, 110, 120, 130, 140, 150, 160, 170, 180, 190, 200, 210, 220, 230, 240, or 250 nucleotides. In certain embodiments, the targeting RNA sequence in the dRNA is about any one of 40-260, 45-250, 50-240.60-230, 65-220, 70-220, 70-210, 70-200, 70-190, 70-180, 70-170, 70-160, 70-150, 70-140, 70-130, 70-120, 70-110, 70-100, 70-90, 70-80, 75-200, 80-190, 85-180, 90-170, 95-160, 100-200, 100-150, 100-175, 110-200, 110-175, 110-150, 140-160, 105-140, or 105-155 nucleotides in length. In some embodiments, the targeting RNA sequence in the dRNA is about 71 nucleotides long. In some embodiments, the dRNA is about 111 nucleotides long. In some embodiments, the dRNA is about 151 nucleotides long.

In some embodiments, the targeting RNA sequence comprises a cytidine, adenosine or uridine directly opposite the target adenosine residue in the target RNA. In some embodiments, the targeting RNA sequence comprises a cytidine mismatch directly opposite the target adenosine residue in the target RNA. In some embodiments, the cytidine mismatch is located at least 5 nucleotides, e.g., at least 10, 15, 20, 25, 30, or more nucleotides, away from the 5' end of the targeting RNA sequence. In some embodiments, the cytidine mismatch is located at least 20 nucleotides, e.g., at least 25, 30, 35, or more nucleotides, away from the 3' end of the complementary RNA sequence. In some embodiments, the cytidine mismatch is not located within 20 (e.g., 15, 10, 5 or fewer) nucleotides away from the 3' end of the targeting RNA sequence. In some embodiments, the cytidine mismatch is located at least 20 nucleotides (e.g., at least 25, 30, 35, or more nucleotides) away rom the 3' end and at least 5 nucleotides (e.g., at least 10, 15, 20, 25, 30, or more nucleotides) away from the 5' end of the targeting RNA sequence. In some embodiments, the cytidine mismatch is located in the center of the targeting RNA sequence. In some embodiments, the cytidine mismatch is located within 20 nucleotides (e.g., 15, 10, 9, 8, 7, 6, 5, 4, 3, 2, or 1 nucleotide) of the center of the targeting sequence in the dRNA.

In some embodiments according to any one of the methods described herein, the targeting RNA sequence further comprises one or more guanosine(s), such as 1, 2, 3, 4, 5, 6, or more Gs, that is each directly opposite a non-target adenosine in the target RNA. In some embodiments, the targeting RNA sequence comprises two or more consecutive mismatch nucleotides (e.g., 2, 3, 4, 5, or more mismatch nucleotides) opposite a non-target adenosine in the target RNA.

In some embodiments, the target RNA comprises no more than about 20 non-target As, such as no more than about any one of 15, 10, 9, 8, 7, 6, 5, 4, 3, 2, or 1 non-target A. The is and consecutive mismatch nucleotides opposite non-target As may reduce off-target editing effects by ADAR.

In certain embodiments according to any one of the methods described herein, the 5' nearest neighbor of the target adenosine residue is a nucleotide selected from U. C. A and G with the preference U>C≈A>G and the 3' nearest neighbor of the target adenosine residue is a nucleotide selected from G, C, A and U with the preference G>C>A=U. In certain embodiments, the target adenosine residue is in a three-base motif selected from the group consisting of UAG, UAC, UAA, UAU, CAG, CAC, CAA, CAU, AAG, AAC, AAA, AAU, GAG, GAC, GAA and GAU in the target RNA. In certain embodiments, the three-base motif is UAG, and the dRNA comprises an A directly opposite the U in the three-base motif, a C directly opposite the target A, and a C, G or U directly opposite the G in the three-base motif. In some embodiments, the three-base motif is UAG in the target RNA, and the dRNA comprises ACC, ACG or ACU that is opposite the UAG of the target RNA. In certain embodiments, the three-base motif is UAG in the target RNA, and the dRNA comprises ACC that is opposite the UAG of the target RNA.

In some embodiments according to any one of the methods described herein, the target RNA is any one selected from the group consisting of a pre-messenger RNA, a messenger RNA, a ribosomal RNA, a transfer RNA, a long non-coding RNA and a small RNA (e.g., miRNA). In some embodiments, the target RNA is a pre-messenger RNA. In some embodiments, the target RNA is a messenger RNA.

In certain embodiments according to any one of the methods described herein, the method further comprises introducing an inhibitor of ADAR3 to the host cell. In some embodiments, the inhibitor of ADAR3 is an RNAi against ADAR3, such as a shRNA against ADAR3 or a siRNA against ADAR3. In some embodiments, the method further comprises introducing a stimulator of interferon to the host cell. In some embodiments, the ADAR is inducible by interferon, for example, the ADAR is ADARp150. In some embodiments, the stimulator of interferon is IFNα. In some embodiments, the inhibitor of ADAR3 and/or the stimulator of interferon are encoded by the same construct (e.g., vector) that encodes the dRNA.

In certain embodiments according to any one of the methods described herein, the efficiency of editing of the target RNA is at least about 10%, such as at least about any one of 15%, 20%, 25%, 30%, 35%, 40%, 45%, 50%, 55%, 60%, 65%, 70%, 75%, 80%, 85%, 90%, or higher. In some embodiments, the efficiency of editing of the target RNA is at least about 40%. In some embodiments, the efficiency of editing is determined by Sanger sequencing. In some embodiments, the efficiency of editing is determined by next-generation sequencing. In some embodiments, the efficiency of editing is determined by assessing expression of a reporter gene, such as a fluorescence reporter, e.g., EGFP.

In certain embodiments according to any one of the methods described herein, the method has low off-target editing rate. In some embodiments, the method has lower than about 1% (e.g., no more than about any one of 0.5%, 0.1%, 0.05%, 0.01%, 0.001% or lower) editing efficiency on non-target As in the target RNA. In some embodiments, the method does not edit non-target As in the target RNA. In some embodiments, the method has lower than about 0.1% (e.g., no more than about any one of 0.05%, 0.01%, 0.005%, 0.001%, 0.0001% or lower) editing efficiency on As in non-target RNA.

In certain embodiments according to any one of the methods described herein, the method does not induce immune response, such as innate immune response. In some embodiments, the method does not induce interferon and/or interleukin expression in the host cell. In some embodiments, the method does not induce IFN-β and/or IL-6 expression in the host cell.

Also provided are edited RNA or host cells having an edited RNA produced by any one of the methods described herein. In some embodiments, the edited RNA comprises an inosine. In some embodiments, the host cell comprises an RNA having a missense mutation, an early stop codon, an alternative splice site, or an aberrant splice site. In some embodiments, the host cell comprises a mutant, truncated, or misfolded protein.

Methods of non-viral delivery of nucleic acids include lipofection, nucleofection, microinjection, biolistics, virosomes, liposomes, immunoliposomes, polycation or lipid:nucleic acid conjugates, electroporation, nanoparticles, exosomes, microvesicles, or gene-gun, naked DNA and artificial virions.

The use of RNA or DNA viral based systems for the delivery of nucleic acids has high efficiency in targeting a virus to specific cells and trafficking the viral payload to the cellular nuclei.

In certain embodiments according to any one of the methods described herein, the method comprises introducing a viral vector (such as an AAV or a lentiviral vector) encoding the dRNA to the host cell. In some embodiments, the vector is a recombinant adeno-associated virus (rAAV) vector. In some embodiments, the construct is flanked by one or more AAV inverted terminal repeat (ITR) sequences. In some embodiments, the construct is flanked by two AAV ITRs. In some embodiments, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV 12, AAV2R471A, AAV DJ, a goat AAV, bovine AAV, or mouse AAV serotype ITRs. In some embodiments, the AAV ITRs are AAV2 ITRs. In some embodiments, the vector further comprises a stuffer nucleic acid. In some embodiments, the stuffer nucleic acid is located upstream or downstream of the nucleic acid encoding the dRNA. In some embodiments, the vector is a self-complementary rAAV vector. In some embodiments, the vector comprises first nucleic acid sequence encoding the dRNA and a second nucleic acid sequence encoding a complement of the dRNA, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence. In some embodiments, the vector is encapsidated in a rAAV particle. In some embodiments, the AAV viral particle comprises an AAV1, AAV2, AAV3, AAV4, AAV5, AAV6, AAV7, AAV8, AAVrhg, AAVrh8R, AAV9, AAV10, AAVrh0, AAV11, AAV12, AAV2R471A, AAV2/2-7m8, AAV DJ, AAV2 N587A, AAV2 E548A, AAV2 N708A, AAV2 V708K, AAV2-HBKO, AAVDJ8, AAVPHP.B, AAVPHP.eB, AAVBR1, AAVHSC15, AAVHSC17, goat AAV, AAV1/AAV2 chimeric, bovine AAV, mouse AAV, or rAAV2/HBoV1 serotype capsid.

In some embodiments, the method comprises introducing a plasmid encoding the dRNA to the host cell. In some embodiments, the method comprises electroporation of the dRNA (e.g., synthetic dRNA) into the host cell. In some embodiments, the method comprises transfection of the dRNA into the host cell.

After deamination, modification of the target RNA and/or the protein encoded by the target RNA, can be determined using different methods depending on the positions of the targeted adenosines in the target RNA. For example, in order to determine whether "A" has been edited to "I" in the target RNA, RNA sequencing methods known in the art can be used to detect the modification of the RNA sequence. When the target adenosine is located in the coding region of an mRNA, the RNA editing may cause changes to the amino acid sequence encoded by the mRNA. For example, point mutations may be introduced to the mRNA of an innate or acquired point mutation in the mRNA may be reversed to yield wild-type gene product(s) because of the conversion of "A" to "I". Amino acid sequencing by methods known in the art can be used to find any changes of amino acid residues in the encoded protein. Modifications of a stop codon may be determined by assessing the presence of a functional, elongated, truncated, full-length and/or wild-type protein. For example, when the target adenosine is located in a UGA, UAG, or UAA stop codon, modification of the target adenosine residue (UGA or UAG) or As (UAA) may create a read-through mutation and/or an elongated protein, or a truncated protein encoded by the target RNA may be reversed to create a functional, foil-length and/or wild-type protein. Editing of a target RNA may also generate an aberrant splice site, and/or alternative splice site in the target RNA, thus leading to an elongated, truncated, or misfolded protein, or an aberrant splicing or alternative splicing site encoded in the target RNA may be reversed to create a functional, correctly-folding, full-length and/or wild-type protein. In some embodiments, the present application contemplates editing of both innate and acquired genetic changes, for example, missense mutation, early stop codon, aberrant splicing or alternative splicing site encoded by a target RNA. Using known methods to assess the function of the protein encoded by the target RNA can find out whether the RNA editing achieves the desired effects. Because deamination of the adenosine (A) to an inosine (I) may correct a mutated A at the target position in a mutant RNA encoding a protein, identification of the deamination into inosine may provide assessment on whether a functional protein is present, or whether a disease or drug resistance-associated RNA caused by the presence of a mutated adenosine is reversed or partly reversed. Similarly, because deamination of the adenosine (A) to an inosine (I) may introduce a point mutation in the resulting protein, identification of the deamination into inosine may provide a functional indication for identifying a cause of disease or a relevant factor of a disease.

When the presence of a target adenosine causes aberrant splicing, the read-out may be the assessment of occurrence and frequency of aberrant splicing. On the other hand, when the deamination of a target adenosine is desirable to introduce a splice site, then similar approaches can be used to check whether the required type of splicing occurs. An exemplary suitable method to identify the presence of an inosine after deamination of the target adenosine is RT-PCR and sequencing, using methods that are well-known to the person skilled in the art.

The effects of deamination of target adenosine(s) include, for example, point mutation, early stop codon, aberrant splice site, alternative splice site and misfolding of the resulting protein. These effects may induce structural and functional changes of RNAs and/or proteins associated with diseases, whether they are genetically inherited or caused by acquired genetic mutations, or may induce structural and functional changes of RNAs and/or proteins associated with occurrence of drug resistance. Hence, the dRNAs, the constructs encoding the dRNAs, and the RNA editing methods of present application can be used in prevention or treatment of hereditary genetic diseases or conditions, or diseases or conditions associated with acquired genetic mutations by changing the structure and/or function of the disease-associated RNAs and/or proteins.

In some embodiments, the target RNA is a regulatory RNA. In some embodiments, the target RNA to be edited is a ribosomal RNA, a transfer RNA, a long non-coding RNA or a small RNA (e.g., miRNA, pri-miRNA, pre-miRNA, piRNA, siRNA, snoRNA, snRNA, exRNA or scaRNA). The effects of deamination of the target adenosines include, for example, structural and functional changes of the ribosomal RNA, transfer RNA, long non-coding RNA or small RNA (e.g., miRNA), including changes of three-dimensional structure and/or loss of function or gain of function of the target RNA. In some embodiments, deamination of the target As in the target RNA changes the expression level of one or more downstream molecules (e.g., protein, RNA and/or metabolites) of the target RNA. Changes of the expression level of the downstream molecules can be increase or decrease in the expression level.

Some embodiments of the present application involve multiplex editing of target RNAs in host cells, which are useful for screening different variants of a target gene or different genes in the host cells. In some embodiments, wherein the method comprises introducing a plurality of dRNAs to the host cells, at least two of the dRNAs of the plurality of dRNAs have different sequences and/or have different target RNAs. In some embodiments, each dRNA has a different sequence and/or different target RNA. In some embodiments, the method generates a plurality (e.g., at least 2, 3, 5, 10, 50, 100, 1000 or more) of modifications in a single target RNA in the host cells. In some embodiments, the method generates a modification in a plurality (e.g., at least 2, 3, 5, 10, 50, 100, 1000 or more) of target RNAs in the host cells. In some embodiments, the method comprises editing a plurality of target RNAs in a plurality of populations of host cells. In some embodiments, each population of host cells receive a different dRNA or a dRNAs having a different target RNA from the other populations of host cells.

III. Deaminase-Recruiting RNA, Constructs and Libraries

Also provided herein are deaminase-recruiting RNAs or constructs useful for any one of the methods described herein. Any one of the dRNAs or constructs described in this section may be used in the methods of RNA editing and treatment described herein. It is intended that any of the features and parameters described herein for dRNAs or constructs can be combined with each other, as if each and every combination is individually described. The dRNAs described herein do not comprise a tracrRNA, crRNA or gRNA used in a CRISPR/Cas system. In some embodiments, there is provided a deaminase-recruiting RNA (dRNA) for deamination of a target adenosine in a target RNA by recruiting an ADAR, comprising a complementary RNA sequence that hybridizes to the target RNA.

In one aspect, the present provides a construct comprising any one of the deaminase-recruiting RNAs described herein. In certain embodiments, the construct is a viral vector (such as a lentivirus vector) or a plasmid. In some embodiments, the construct encodes a single dRNA. In some embodiments, the construct encodes a plurality (e.g., about any one of 1, 2, 3, 4, 5, 10, 20 or more) dRNAs.

In one aspect, the present application provides a library comprising a plurality of the deaminase-recruiting RNAs or a plurality of the constructs described herein.

In one aspect, the present application provides a composition or a host cell comprising the deaminase-recruiting RNA or the construct described herein. In certain embodiments, the host cell is a prokaryotic cell or a eukaryotic cell. In some embodiments, the host cell is a mammalian cell. In some embodiments, the host cell is a human cell.

Circular dRNAs and Constructs

In one aspect, provided herein is a deaminase-recruiting RNAs (dRNA) for editing a target RNA comprising a targeting RNA sequence that is at least partially complementary to the target RNA, wherein the dRNA is capable of recruiting an Adenosine Deaminase Acting on RNA (ADAR), and wherein the dRNA is circular or is capable of forming a circular RNA.

In some embodiments, the dRNA is a linear RNA that is capable of forming a circular RNA. In some embodiments, the dRNA is circulated by the Tornado method. In some embodiments, the dRNA transcript is also flanked by a 5' and/or 3' ligation sequences which are then flanked by the 5'-Twister ribozyme and/or 3'-Twister ribozymes, respectively. In some embodiments, the 3' ligation sequence and the 5' ligation sequence are at least partially complementary to each other. In some embodiments, the 3' ligation sequence and the 5' ligation sequence are at least about 50%, at least about 55%, at least about 60%, at least about 65%, at least about 70%, at least about 75%, at least about 80%, at least about 85%, at least about 90%, at least about 95%, at least about 96%, at least about 97%, at least about 98% or at least about 99% complementary to each other. In some embodiments, the 3' ligation sequence and the 5' ligation sequence are fully complementary to each other.

In some embodiments, the 3' ligation sequence and the 5' ligation sequence are independently at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides or at least about 100 nucleotides in length. In some embodiments, the 3' ligation sequence and the 5' ligation sequence are independently about 20-30 nucleotides, about 30-40 nucleotides, about 40-50 nucleotides, about 50-60 nucleotides, about 60-70 nucleotides, about 70-80 nucleotides, about 80-90 nucleotides, about 90-100 nucleotides, about 100-125 nucleotides, about 125-150 nucleotides, about 20-50 nucleotides, about 50-100 nucleotides or about 100-150 nucleotides in length.

In some embodiments, the dRNA is circularized by an RNA ligase. In some embodiments, the RNA ligase is expressed endogenously in the host cell. In some embodiments, the RNA ligase is RNA ligase RtcB. In some embodiments, the RNA ligase RtcB is expressed endogenously in the host cell. In some embodiments, the dRNA is circularized through in vitro enzymatic ligation (e.g., using RNA or DNA ligase) or chemical ligation (e.g., using cyanogen bromide or a similar condensing agent).

Also provided herein is a construct comprising a nucleic acid encoding the dRNA. In some embodiments, the dRNA is introduced by a construct comprising a nucleic acid encoding the dRNA. In some embodiments, the construct further comprises a 3' twister ribozyme sequence linked to the 3' end of the nucleic acid encoding the dRNA. In some embodiments, the construct further comprises a 5' twister ribozyme sequence linked to the 5' end of the nucleic acid encoding the dRNA. In some embodiments, the construct further comprises a 3' twister ribozyme sequence linked to the 3' end of the nucleic acid encoding the dRNA and a 5' twister ribozyme sequence linked to the 5' end of the nucleic acid encoding the dRNA. In some embodiments, the 3' twister sequence is twister P3 U2A and the 5' twister sequence is twister P1. In some embodiments, wherein the 5' twister sequence is twister P3 U2A and the 3' twister sequence is twister P1. In some embodiments, the dRNA undergoes autocatalytic cleavage. In some embodiments, the catalyzed dRNA product comprises a 5'-hydroxyl group and a 2',3'-cyclic phosphate at the 3' terminus. In some embodiments, the catalyzed dRNA product is ligated by ubiquitous endogenous RNA ligase (e.g., RNA ligase RtcB). In some embodiments, the construct is a plasmid or a viral vector.

dRNA Having One or Two snoRNA Ends and Constructs

In another aspect, provided herein is a deaminase-recruiting RNA (dRNA) for editing a target RNA comprising: (1) a targeting RNA sequence that is at least partially complementary to the target RNA and (2) a small nucleolar RNA (snoRNA) sequence at the 3' and/or 5' ends of the targeting RNA sequence; wherein the dRNA is capable of recruiting an adenosine deaminase acting on RNA (ADAR).

In some embodiments, the dRNA comprises a snoRNA sequence linked to the 5' end of the targeting RNA sequence ("5' snoRNA sequence"). In some embodiments, the dRNA comprises a snoRNA sequence linked to the 3' end of the targeting RNA sequence ("3' snoRNA sequence"). In some embodiments, the snoRNA sequence is at least about 50 nucleotides, at least about 60 nucleotides, at least about 70 nucleotides, at least about 80 nucleotides, at least about 90 nucleotides, at least about 100 nucleotides, at least about 110 nucleotides, at least about 120 nucleotides, at least about 130 nucleotides, at least about 140 nucleotides, at least about 150 nucleotides, at least about 160 nucleotides, at least about 170 nucleotides, at least about 180 nucleotides, at least about 190 nucleotides or at least about 200 nucleotides in length."). In some embodiments, the snoRNA sequence is about 50-75 nucleotides, about 75-100 nucleotides, about 100-125 nucleotides, about 125-150 nucleotides, about 150-175 nucleotides, about 175-200 nucleotides, about 50-100 nucleotides, about 100-150 nucleotides, about 150-200 nucleotides, about 125-175 nucleotides, or about 100-200 nucleotides in length.

In some embodiments, the 3' snoRNA sequence comprises the nucleic acid sequence of SEQ ID NO: 1. In some embodiments, the 5' snoRNA sequence comprises the nucleic acid sequence of SEQ ID NO: 2. In some embodiments, the snoRNA sequence is a C/D Box snoRNA sequence. In some embodiments, the snoRNA sequence is an H/ACA Box snoRNA sequence. In some embodiments, the snoRNA sequence is a composite C/D Box and H/ACA Box snoRNA sequence. In some embodiments, the snoRNA sequence is an orphan snoRNA sequence.

Constructs with Pol II Promoter

In another aspect, provided herein is a construct comprising a nucleic acid encoding a deaminase-recruiting RNA (dRNA) into the host cell, wherein: (1) the dRNA comprises a targeting RNA sequence that is at least partially complementary to the target RNA, (2) the dRNA is capable of recruiting an adenosine deaminase acting on RNA (ADAR), and (3) the construct comprises a polymerase II promoter ("Pol II promoter") operably linked to the nucleic acid encoding the dRNA.

In some embodiments, the Pol II promoter that is operably linked to the coding nucleotide sequence, such that the promoter controls the transcription or expression of the coding nucleotide sequence. The Pol II promoter may be positioned 5' (upstream) of a coding nucleotide sequence under its control. The distance between the Pol II promoter and the coding sequence may be approximately the same as the distance between that promoter and the gene it controls in the gene from which the promoter is derived. As is known in the art, variation in this distance may be accommodated without loss of promoter function. In some embodiments, the construct comprises a 5' UTR and/or a 3'UTR that regulates the transcription or expression of the coding nucleotide sequence. In some embodiments, the Pol II promoter is a CMV promoter. In some embodiments, the CMV promoter comprises the nucleic acid sequence of SEQ ID NO: 3. In some embodiments, one Pol II promoter (e.g., CMV) is driving expression of two or more dRNAs.

In some embodiments according to any one of the dRNAs, constructs, libraries or compositions described herein, the targeting RNA sequence comprises a cytidine, adenosine or uridine directly opposite the target adenosine to be edited in the target RNA. In some embodiments, the targeting RNA sequence further comprises one or more guanosine(s) that is each directly opposite a non-target adenosine in the target RNA. In certain embodiments, the 5' nearest neighbor of the target adenosine residue is a nucleotide selected from U, C, A and G with the preference U>C≈A>G and the 3' nearest neighbor of the target adenosine residue is a nucleotide selected from G, C, A and U with the preference G>C>A≈U. In some embodiments, the 5' nearest neighbor of the target adenosine residue is U. In some embodiments, the 5' nearest neighbor of the target adenosine residue is C or A. In some embodiments, the 3' nearest neighbor of the target adenosine residue is G. In some embodiments, the 3' nearest neighbor of the target adenosine residue is C.

In some embodiments according to any one of the dRNAs, constructs, libraries or compositions described herein, the target adenosine residue is in a three-base motif selected from the group consisting of UAG, UAC, UAA, UAU, CAG, CAC, CAA, CAU, AAG, AAC, AAA, AAU, GAG, GAC, GAA and GAU in the target RNA. In some embodiments, the three-base motif is UAG, and the dRNA comprises an A directly opposite the U in the three-base motif, a C directly opposite the target A, and a C, U or U directly opposite the G in the three-base motif. In certain embodiments, the three-base motif is UAG in the target RNA, and the dRNA comprises ACC, ACG or ACU that is opposite the UAG of the target RNA.

In some embodiments, the dRNA comprises a cytidine mismatch directly opposite the target adenosine residue in the target RNA. In some embodiments, the cytidine mismatch is close to the center of the complementary RNA sequence, such as within 20, 15, 10, 5, 4, 3, 2, or 1 nucleotide away from the center of the complementary RNA sequence. In some embodiments, the cytidine mismatch is at least 5 nucleotides away from the 5' end of the complementary RNA sequence. In some embodiments, the cytidine mismatch is at least 20 nucleotides away from the 3' end of the complementary RNA sequence.

In some embodiments according to any one of the dRNAs, constructs, libraries or compositions described herein, the dRNA comprises more than about any one of 40, 45, 50, 55, 60, 65, 70, 75, 80, 90, 100, 110, 120, 130, 140, 150, 160, 170, 180, 190, 200, 210, 220, 230, 240, or 250 nucleotides. In certain embodiments, the dRNA is about any one of 40-260, 45-250, 50-240, 60-230, 65-220, 70-210, 70-200, 70-190, 70-180, 70-170, 70-160, 70-150, 70-140, 70-130, 70-120, 70-110, 70-100, 70-90, 70-80, 75-200, 80-190, 85-180, 90-170, 95-160, 100-150 or 105-140 nucleotides in length.

The dRNA of the present application comprises a targeting RNA sequence that hybridizes to the target RNA. The targeting RNA sequence is perfectly complementary or substantially complementarity to the target RNA to allow hybridization of the targeting RNA sequence to the target RNA. In some embodiments, the targeting RNA sequence has 100% sequence complementarity as the target RNA. In some embodiments, the targeting RNA sequence is at least about any one of 70%, 80%, 85%, 90%, 95%, 96%, 97%, 98%, or 99% or more complementary to over a continuous stretch of at least about any one of 20, 40, 60, 80, 100, 150, 200, or more nucleotides in the target RNA. In some embodiments, the dsRNA formed by hybridization between the targeting RNA sequence and the target RNA has one or more (e.g., 1, 2, 3, 4, 5, 6, 7, 8, 9, 10 or more) non-Watson-Crick base pairs (i.e., mismatches).

ADAR, for example, human ADAR enzymes edit double stranded RNA (dsRNA) structures with varying specificity, depending on a number of factors. One important factor is the degree of complementarity of the two strands making up the dsRNA sequence. Perfect complementarity of between the dRNA and the target RNA usually causes the catalytic domain of ADAR to deaminate adenosines in a non-discriminative manner. The specificity and efficiency of ADAR can be modified by introducing mismatches in the dsRNA region. For example, A-C mismatch is preferably recommended to increase the specificity and efficiency of deamination of the adenosine to be edited. Conversely, at the other A (adenosine) positions than the target adenosine residue (i.e., "non-target A"), the G-A mismatch can reduce off-target editing. Perfect complementarity is not necessarily required for a dsRNA formation between the dRNA and its target RNA, provided there is substantial complementarity for hybridization and formation of the dsRNA between the dRNA and the target RNA. In some embodiments, the dRNA sequence or single-stranded RNA region thereof has at least about any one of 70%, 80%, 85%, 90%, 95%, 96%, 97%, 98%, or 99% of sequence complementarity to the target RNA, when optimally aligned. Optimal alignment may be determined with the use of any suitable algorithm for aligning sequences, non-limiting examples of which include the Smith-Waterman algorithm, the Needlenan-Wimsch algorithm, algorithms based on the Burrows-Wheeler Transform (e.g., the Burrows Wheeler Aligner).

The nucleotides neighboring the target adenosine also affect the specificity and efficiency of deamination. For example, the 5' nearest neighbor of the target adenosine to be edited in the target RNA sequence has the preference U>C≈A>G and the 3' nearest neighbor of the target adenosine to be edited in the target RNA sequence has the preference G>C>A≈U in terms of specificity and efficiency of deamination of adenosine. In some embodiments, when the target adenosine may be in a three-base motif selected from the group consisting of UAG, UAC, UAA. UAU, CAG, CAC, CAA, CAU, AAG, AAC, AAA, AAU, GAG, GAC, GAA and GAU in the target RNA, the specificity and efficiency of deamination of adenosine are higher than adenosines in other three-base motifs. In some embodiments, where the target adenosine to be edited is in the three-base motif UAG, UAC, UAA, UAU, CAG, CAC, AAG, AAC or AAA, the efficiency of deamination of adenosine is much higher than adenosines in other motifs. With respect to the same three-base motif, different designs of dRNA may also lead to different deamination efficiency. Taking the three-base motif UAG as an example, in some embodiments, when the dRNA comprises cytidine (C) directly opposite the target adenosine to be edited, adenosine (A) directly opposite the uridine, and cytidine (C), guanosine (G) or uridine (U) directly opposite the guanosine, the efficiency of deamination of the target adenosine is higher than that using other dRNA sequences. In some embodiments, when the dRNA comprises ACC, ACG or ACU opposite UAG of the target RNA, the editing efficiency of the A in the UAG of the target RNA may reach about 25%-90% (e.g., about 25%-80%, 25%-70%, 25%-60%, 25%-50%, 25%-40%, or 25%-30%).

Besides the target adenosines, there may be one or more adenosines in the target RNA, which are not desirable to be edited. With respect to these adenosines, it is preferable to reduce their editing efficiency as much as possible. It is found by this disclosure that where guanosine is directly opposite an adenosine in the target RNA, the deamination efficiency is significantly decreased. Therefore, in order to decrease off-target deamination, dRNAs can be designed to comprise one or more guanosines directly opposite one or more adenosine(s) other than the target adenosine to be edited in the target RNA.

The desired level of specificity and efficiency of editing the target RNA sequence may depend on different applications. Following the instructions in the present patent application, those of skill in the art will be capable of designing a dRNA having complementary or substantially complementary sequence to the target RNA sequence according to their needs, and, with some trial and error, obtain their desired results. As used herein, the term "mismatch" refers to opposing nucleotides in a double stranded RNA (dsRNA) which do not form perfect base pairs according to the Watson-Crick base pairing rules. Mismatch base pairs include, for example, G-A, C-A, U-C, A-A, G-G, C-C, U-U base pairs. Taking A-C match as an example, where a target adenosine residue is to be edited in the target RNA, a dRNA is designed to comprise a C opposite the A to be edited, generating an A-C mismatch in the dsRNA formed by hybridization between the target RNA and dRNA.

In some embodiments, the dsRNA formed by hybridization between the dRNA and the target RNA does not comprise a mismatch. In some embodiments, the dsRNA formed by hybridization between the dRNA and the target RNA comprises one or more, such as any one of 1, 2, 3, 4, 5, 6, 7 or more mismatches (e.g., the same type of different types of mismatches). In some embodiments, the dsRNA formed by hybridization between the dRNA and the target RNA comprises one or more kinds of mismatches, for example, 1, 2, 3, 4, 5, 6, 7 kinds of mismatches selected from the group consisting of G-A, C-A, U-C, A-A, G-G, C-C and U-U.

The mismatch nucleotides in the dsRNA formed by hybridization between the dRNA and the target RNA can form bulges, which can promote the efficiency of editing of the target RNA. There may be one (which is only formed at the target adenosine) or more bulges formed by the mismatches. The additional bulge-inducing mismatches may be upstream and/or downstream of the target adenosine. The bulges may be single-mismatch bulges (caused by one mismatching base pair) or multi-mismatch bulges (caused by more than one consecutive mismatching base pairs, e.g., two or three consecutive mismatching base pairs).

The targeting RNA sequence in the dRNA is single-stranded. The dRNA may be entirely single-stranded or have one or more (e.g., 1, 2, 3, or more) double-stranded regions and/or one or more stem loop regions. In some embodiments, the targeting RNA sequence is at least about any one of 40, 45, 50, 55, 60, 65, 70, 75, 80, 90, 100, 110, 120, 130, 140, 150, 160, 170, 180, 190, 200 or more nucleotides. In certain embodiments, the targeting RNA sequence is about any one of 40-260, 45-250, 50-240, 60-230, 65-220, 70-220, 70-210, 70-200, 70-190, 70-180, 70-170, 70-160, 70-150, 70-140, 70-130, 70-120, 70-110, 70-100, 70-90, 70-80, 75-200, 80-190, 85-180, 90-170,95-160, 100-200, 100-150, 100-175, 110-200, 110-160, 110-175, 110-150, 140-160, 105-140, or 105-155 nucleotides in length. In some embodiments, the targeting RNA sequence in the dRNA is about 71 nucleotides long. In some embodiments, the dRNA is about 111 nucleotides long. In some embodiments, the dRNA is about 151 nucleotides long.

In some embodiments, the dRNA, apart from the targeting RNA sequence, further comprises regions for stabilizing the dRNA, for example, one or more double-stranded regions and/or stem loop regions. In some embodiments, the double-stranded region or stem loop region of the dRNA comprises no more than about any one of 200, 150, 100, 50, 40, 30, 20, 10 or fewer base-pairs. In some embodiments, the dRNA does not comprise a stem loop or double-stranded region. In some embodiments, the dRNA comprises an ADAR-recruiting domain. In some embodiments, the dRNA does not comprise an ADAR-recruiting domain.

The dRNA may comprise one or more modifications. In some embodiments, the dRNA has one or more modified nucleotides, including nucleobase modification and/or backbone modification. Exemplary modifications to the RNA include, but are not limited to, phosphorothioate backbone modification, 2'-substitutions in the ribose (such as 2'-O-methyl and 2'-fluoro substitutions), LNA, and L-RNA. In some embodiments, the dRNA does not have modifications to the nucleobase or backbone.

The present application also contemplates a construct comprising the dRNA described herein, including, but not limited to, any of the constructs described in the sections above. The term "construct" as used herein refers to DNA or RNA molecules that comprise a coding nucleotide sequence that can be transcribed into RNAs or expressed into proteins. In some embodiments, the construct contains one or more regulatory elements operably linked to the nucleotide sequence encoding the RNA or protein. When the construct is introduced into a host cell, under suitable conditions, the coding nucleotide sequence in the construct can be transcribed or expressed.

In some embodiments, the construct comprises a promoter that is operably linked to the coding nucleotide sequence, such that the promoter controls the transcription or expression of the coding nucleotide sequence. A promoter may be positioned 5' (upstream) of a coding nucleotide sequence under its control. The distance between the promoter and the coding sequence may be approximately the same as the distance between that promoter and the gene it controls in the gene from which the promoter is derived. As is known in the art, variation in this distance may be accommodated without loss of promoter function. In some embodiments, the construct comprises a 5' UTR and/or a 3'UTR that regulates the transcription or expression of the coding nucleotide sequence. In some embodiments, the promoter is a U6 promoter. IN some embodiments, the promoter is a Poly II promoter as discussed in the sections described above.

In some embodiments, the construct is a vector encoding any one of the dRNAs disclosed in the present application. The term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g, circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the transcription or expression of coding nucleotide sequences to which they are operatively linked. Such vectors are referred to herein as "expression vectors".

Recombinant expression vectors can comprise a nucleic acid of the present application in a form suitable for transcription or expression of the nucleic acid in a host cell. In some embodiments, the recombinant expression vector includes one or more regulatory elements, which may be selected on the basis of the host cells to be used for transcription or expression, which is operatively linked to the nucleic acid sequence to be transcribed or expressed. Within a recombinant expression vector, "operably linked" is intended to mean that the nucleotide sequence of interest is linked to the regulatory element(s) in a manner that allows for expression of the nucleotide sequence (e.g. in an in vitro transcription translation system or in a host cell when the vector is introduced into the host cell).

In some embodiments, the vector is a rAAV vector. In some embodiments, the rAAV vector is a vector derived from an AAV serotype, including without limitation, AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype or the like. In some embodiments, the nucleic acid in the AAV comprises an ITR of AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype or the like. In some embodiments, the nucleic acid n the AAV further encodes a dRNA as described herein. Use of any AAV serotype is considered within the scope of the present disclosure. In some embodiments, the vector is encapsidated in a rAAV particle. In some embodiments, the AAV viral particle comprises an AAV 1, AAV2, AAV3, AAV4, AAV5, AAV6, AAV7, AAV8, AAVrh8, AAVrh8R, AAV9, AAV10, AAVrh0, AAV11, AAV12, AAV2R471A, AAV2/2-7m8, AAV DJ, AAV2 N587A, AAV2 E548A, AAV2 N708A, AAV2 V708K, AAV2-HBKO, AAVDJ8, AAVPHP.B, AAVPHP.eB, AAVBR1, AAVHSC15, AAVHSC17, goat AAV, AAV1/AAV2 chimeric, bovine AAV, mouse AAV, or rAAV2/HBoV1 serotype capsid.

In some embodiments, there is provided a construct (e.g., vector, such as viral vector) comprising a nucleotide sequence encoding the dRNA. In some embodiments, there is provided a construct (e.g., vector, such as viral vector) comprising a nucleotide sequence encoding the ADAR. In some embodiments, there is provided a construct comprising a first nucleotide sequence encoding the dRNA and a second nucleotide sequence encoding the ADAR. In some embodiments, the first nucleotide sequence and the second nucleotide sequence are operably linked to the same promoter. In some embodiments, the first nucleotide sequence and the second nucleotide sequence are operably linked to different promoters. In some embodiments, the promoter is inducible. In some embodiments, the construct does not encode for the ADAR. In some embodiments, the vector (further comprises nucleic acid sequence(s) encoding an inhibitor of ADAR3 (e.g., ADAR3 shRNA or siRNA) and/or a stimulator of interferon (e.g., IFN-α).

IV. Methods of Treatment

The RNA editing methods and compositions described herein may be used to treat or prevent a disease or condition in an individual, including, but not limited to hereditary genetic diseases and drug resistance.

In some embodiments, there is provided a method of editing a target RNA in a cell of an individual (e.g., human individual) ex vivo, comprising editing the target RNA using any one of the methods of RNA editing described herein.

In some embodiments, there is provided a method of editing a target RNA in a cell of an individual (e.g., human individual) ex vivo, comprising introducing a dRNA or a construct comprising a nucleic acid encoding the dRNA into the cell of the individual, wherein the dRNA comprises a targeting RNA sequence that hybridizes to the target RNA, wherein the dRNA is capable of recruiting an ADAR to deaminate a target adenosine residue in the target RNA, and wherein the dRNA is a circular RNA (i capable of forming a circular RNA.

In some embodiments, there is provided a method of editing a target RNA in a cell of an individual (e.g., human individual) ex vivo, comprising introducing a dRNA or a construct comprising a nucleic acid encoding the dRNA into the cell of the individual, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of editing a target RNA in a cell of an individual (e.g., human individual) ex vivo, comprising introducing a construct comprising a nucleic acid encoding a dRNA into the cell of the individual, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA. In some embodiments, the ADAR is endogenously expressed. In some embodiments, the method further comprises introducing the ADAR or a construct comprising a nucleic acid encoding the ADAR into the cell.

In some embodiments, the target RNA is associated with a disease or condition of the individual. In some embodiments, the disease or condition is a hereditary genetic disease, or a disease or condition associated with one or more acquired genetic mutations (e.g., drug resistance). In some embodiments, the method further comprises obtaining the cell from the individual.

In some embodiments, there is provided a method of treating or preventing a disease or condition in an individual (e.g., human individual), comprising editing a target RNA associated with the disease or condition in a cell of the individual using any one of the methods of RN A editing described herein.

In some embodiments, there is provided a method of treating or preventing a disease or condition in an individual (e.g., human individual), comprising introducing a dRNA or a construct comprising a nucleic acid encoding the dRNA into an isolated cell of the individual ex vivo, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating or preventing a disease or condition in an individual (e.g., human individual), comprising introducing a dRNA or a construct comprising a nucleic acid encoding the dRNA into an isolated cell of the individual ex vivo, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating or preventing a disease or condition in an individual (e.g., human individual), comprising introducing a construct comprising a nucleic acid encoding a dRNA into an isolated cell of the individual ex vivo, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the isolated cell. In some embodiments, the method comprises introducing the ADAR or a construct comprising a nucleic acid encoding the ADAR to the isolated cell. In some embodiments, the method further comprises culturing the cell having the edited RNA. In some embodiments, the method further comprises administering the cell having the edited RNA to the individual. In some embodiments, the disease or condition is a hereditary genetic disease, or a disease or condition associated with one or more acquired genetic mutations (e.g., drug resistance).

In some embodiments, there is provided a method of treating or preventing a disease or condition in an individual (e.g., human individual), comprising administering an effective amount of a dRNA or a construct comprising a nucleic acid encoding the dRNA to the individual, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating or preventing a disease or condition n an individual (e.g., human individual), comprising administering an effective amount or a dRNA or a construct comprising a nucleic acid encoding the dRNA to the individual, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating or preventing a disease or condition in an individual (e.g., human individual), comprising administering an effective amount of a construct comprising a nucleic acid encoding a dRNA to the individual, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the cells of the individual. In some embodiments, the method comprises administering the ADAR or a construct comprising a nucleic acid encoding the ADAR to the individual. In some embodiments, the disease or condition is a hereditary genetic disease, or a disease or condition associated with one or more acquired genetic mutations (e.g., drug resistance).

Diseases and conditions suitable for treatment using the methods of the present application include diseases associated with a mutation, such as a G to A mutation, e.g., a G to A mutation that results in missense mutation, early stop codon, aberrant splicing, or alternative splicing in an RNA transcript. Examples of disease-associated mutations that may be restored by the methods of the present application include, but are not limited to, TP53$^{W53X}$ (e.g., 158G>A) associated with cancer, IDUA$^{W402X}$ (e.g., TGG>TAG mutation in exon 9) associated with Mucopolysaccharidosis type I (MPS I), COL3A1$^{W1278X}$ (e.g., 3833G>A mutation) associated with Ehlers-Danlos syndrome, BHMPR2$^{W298X}$ (e.g., 8930>A) associated with primary pulmonary hypertension, AHI1$^{W725X}$ (e.g., 2174G>A) associated with Joubert syndrome, FANCC$^{W506X}$ (e.g., 1517G>A) associated with Fanconi anemia, MYBPC3$^{W1098X}$ (e.g., 32936>A) associated with primary familial hypertrophic cardiomyopathy, and IL2RG$^{W237X}$ (e.g., 710G>A) associated with X-linked severe combined immunodeficiency. In some embodiments, the disease or condition is a cancer. In some embodiments, the disease or condition is a monogenetic disease. In some embodiments, the disease or condition is a polygenetic disease.

In some embodiments, there is provided a method of treating a cancer associated with a target RNA having a mutation (e.g., G>A mutation) in an individual, comprising introducing a dRNA or a construct comprising a nucleic acid encoding the dRNA into an isolated cell of the individual ex vivo, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating a cancer associated with a target RNA having a mutation (e.g., G>A mutation) in an individual, comprising introducing a dRNA or a construct comprising a nucleic acid encoding the dRNA into an isolated cell of the individual ex vivo, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating a cancer associated with a target RNA having a mutation (e.g., G>A mutation) in an individual, comprising introducing a construct comprising a nucleic acid encoding a dRNA into an isolated cell of the individual ex vivo, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the isolated cell. In some embodiments, the method comprises introducing the ADAR or a construct comprising a nucleic acid encoding the ADAR to the isolated cell. In some embodiments, the target RNA is TP53$^{W53X}$ (e.g., 158G>A). In some embodiments, the dRNA comprises the nucleic acid sequence of SEQ ID NO: 4 (5'-GGGAGCAGCCUCUGGCAUUCUGGGAGCUU-CAUCUGGACUGGGUCUUCAGUGAAC CAUUGUU-CAAUAUCGUCCGGGGACAGCAUCAAAUCAUC-CAUUGCUUGGGACGGCA A-3').

In some embodiments, there is provided a method of treating or preventing a cancer with a target RNA having a mutation (e.g., G>A mutation) in an individual, comprising administering an effective amount of a dRNA or a construct comprising a nucleic acid encoding the dRNA to the individual, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating or preventing a cancer with a target RNA having a mutation (e.g., G>A mutation) in an individual, comprising administering an effective amount of a dRNA or a construct comprising a nucleic acid encoding the dRNA to the individual, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating or preventing a cancer with a target RNA having a mutation (e.g., G>A mutation) in an individual, comprising administering an effective amount of a construct comprising a nucleic acid encoding a dRNA to the individual, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the cells of the individual. In some embodiments, the method comprises administering the ADAR or a construct comprising a nucleic acid encoding the ADAR to the individual. In some embodiments, the target RNA is TP53$^{W53X}$ e.g., 158G>A). In some embodiments, the dRNA comprises the nucleic acid sequence of SEQ ID NO: 4.

In some embodiments, there is provided a method of treating MPS I (e.g, Hurler syndrome or Scheie syndrome) associated with a target RNA having a mutation (e.g., G>A mutation) in an individual, comprising introducing a dRNA or a construct comprising a nucleic acid encoding the dRNA into an isolated cell of the individual ex vivo, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating MPS I (e.g., Hurler syndrome or Scheie syndrome) associated with a target RNA having a mutation (e.g., G>A mutation) in an individual, comprising introducing a dRNA or a construct comprising a nucleic acid encoding the dRNA into an isolated cell of the individual ev vivo, wherein the dRNA comprises a (l) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating MPS I (e.g., Hurler syndrome or Scheie syndrome) associated with a target RNA having a mutation (e.g., G>A mutation) in an individual, comprising introducing a construct comprising a nucleic acid encoding a dRNA into an isolated cell of the individual ex vivo, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the isolated cell. In some embodiments, the method comprises introducing the ADAR or a construct comprising a nucleic acid encoding the ADAR to the isolated cell. In some embodiments, the target RNA is IDUA$^{W402X}$ (e.g., TGG>TAG mutation in exon 9). In some embodiments, the dRNA comprises the nucleic acid sequence of SEQ ID NO: 5 (5'-GACGCCCACCGUGUG-GUUGCUGUCCAGGACGGUCCCGGCCUGCGACAC-UUCGGCC CAGAGCUGCUCCU-CAUCUGCGGGGCGGGGGGGGGCCGUCGCCGCGU-GGGGUCGUU G-3').

In some embodiments, there is provided a method of treating or preventing MPS I (e.g., Hurler syndrome or Scheie syndrome) with a target RNA having a mutation (e.g., G>A mutation) in an individual, comprising administering an effective amount of a dRNA or a construct comprising a nucleic acid encoding the dRNA to the individual, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating or preventing MPS I (e.g., Hurler syndrome or Scheie syndrome) with a target RNA having a mutation (e.g., G>A mutation) in an individual, comprising administering an effective amount of a dRNA or a construct comprising a nucleic acid encoding the dRNA to the individual, wherein the dRNA comprises a (I) targeting RNA sequence that hybridizes to the target RNA and (2) a small nucleolar RNA (snoRNA) sequence linked to the 3 and/or 5' ends of the targeting RNA sequence, and wherein the dRNA is capable of recruiting an ADAR to deaminate a target adenosine residue in the target RNA.

In some embodiments, there is provided a method of treating or preventing MPS I (e.g., Hurler syndrome or Scheie syndrome) with a target RNA having a mutation (e.g., G>A mutation) in an individual, comprising administering an effective amount of a construct comprising a nucleic acid encoding a dRNA to the individual, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the cells of the individual. In some embodiments, the method comprises administering the ADAR or a construct comprising a nucleic acid encoding the ADAR to the individual. In some embodiments, the target RNA is IDUA$^{W402X}$ (e.g., TGG>TAG mutation in exon 9). In some embodiments, the dRNA comprises the nucleic acid sequence of SEQ ID NO: 5.

In some embodiments, there is provided a method of treating a disease or condition Ehlers-Danlos syndrome associated with a target RNA having a mutation (e.g., G>A mutation) in an individual, comprising introducing a dRNA or a construct comprising a nucleic acid encoding the dRNA into an isolated cell of the individual ex vivo, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating a disease or condition Ehlers-Danlos syndrome associated with a target RNA having a mutation (e.g, G>A mutation) in an individual, comprising introducing a dRNA or a construct comprising a nucleic acid encoding the dRNA into an isolated cell of the individual ex vivo, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating a disease or condition Ehlers-Danlos syndrome associated with a target RNA having a mutation (e.g., G>A mutation) in an individual, comprising introducing a construct comprising a nucleic acid encoding a dRNA into an isolated cell of the individual ex vivo, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the isolated cell. In some embodiments, the method comprises introducing the ADAR or a construct comprising a nucleic acid encoding the ADAR to the isolated cell. In some embodiments, the target RNA is COL3A1$^{W1278X}$ (e.g., 3833G>A mutation). In some embodiments, the dRNA comprises the nucleic acid sequence of SEQ ID NO: 6 (5'-CAUAUUACAGAAUACC-UUGAUAGCAUCCAAUUUGCAUCCUUGGUUAGG-GUCAAC CCAGUAUUCUCCACUCUUGAGUUCAG-GAUGGCAGAAUUUCAGGUCUCUGCAGUU UCU-3').

In some embodiments, there is provided a method of treating or preventing Ehlers-Danlos syndrome with a target RNA having a mutation (e.g., G>A mutation) in an individual, comprising administering an effective amount of a dRNA or a construct comprising a nucleic acid encoding the dRNA to the individual, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating or preventing Ehlers-Danlos syndrome with a target RNA having a mutation (e.g., G>A mutation) in an individual, comprising administering an effective amount of a dRNA or a construct comprising a nucleic acid encoding the dRNA to the individual, wherein the dRNA comprises a (1) targeting RNA sequence that hybridize, to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating or preventing Ehlers-Danlos syndrome with a target RNA having a mutation (e.g., G>A mutation) in an individual, comprising administering an effective amount of a construct comprising a nucleic acid encoding a dRNA to the individual, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the cells of the individual. In some embodiments, the method comprises administering the ADAR or a construct comprising a nucleic acid encoding the ADAR to the individual. In some embodiments, the target RNA is COL3A1$^{W127X}$ (e.g., 3833G>A mutation). In some embodiments, the dRNA comprises the nucleic acid sequence of SEQ ID NO: 6.

In some embodiments, there is provided a method of treating primary pulmonary hypertension associated with a target RNA having a mutation (e.g., G>A mutation) in an individual, comprising introducing a dRNA or a construct comprising a nucleic acid encoding the dRNA into an isolated cell of the individual ex vivo, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating primary pulmonary hypertension associated with a target RNA having a mutation (e.g., G>A mutation) in an individual, comprising introducing a dRNA or a construct comprising a nucleic acid encoding the dRNA into an isolated cell of the individual ex vivo, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating primary pulmonary hypertension associated with a target RNA having a mutation (e.g., G>A mutation) in an individual, comprising introducing a construct comprising a nucleic acid encoding a dRNA into an isolated cell of the individual ex vivo, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the isolated cell. In some embodiments, the method comprises introducing the ADAR or a construct comprising a nucleic acid encoding the ADAR to the isolated cell. In some embodiments, the target RNA is BMPR2$^{W298X}$ (e g, 893G>A). In some embodiments, the dRNA comprises the nucleic acid sequence of SEQ ID NO: 7 (5'-GUGAAGAUAAGCCAGUCCUCU-AGUAACAGAAUGAGCAAGACGGCAAGAGCUUAC CCAGUCACUUGUGUGGAGACUUAAAUACUUG-CAUAAAGAUCCAUUGGGAUAGUA CUC-3').

In some embodiments, there is provided a method of treating or preventing primary pulmonary hypertension with a target RNA having a mutation (e.g., G>A mutation) in an individual, comprising administering an effective amount of a dRNA or a construct comprising a nucleic acid encoding the dRNA to the individual, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating or preventing primary pulmonary hypertension with a target RNA having a mutation (e.g., G>A mutation) in an individual, comprising administering an effective amount of a dRNA or a construct comprising a nucleic acid encoding the dRNA to the individual, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating or preventing primary pulmonary hypertension with a target RNA having a mutation (e.g., G>A mutation) in an individual, comprising administering an effective amount of a dRNA to the individual, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the cells of the individual. In some embodiments, the method comprises administering the ADAR or a construct comprising a nucleic acid encoding the ADAR to the individual. In some embodiments, the target RNA is BMPR2$^{W298X}$ (e.g., 893G>A). In some embodiments, the dRNA comprises the nucleic acid sequence of SEQ ID NO: 7.

In some embodiments, there is provided a method of treating Joubert syndrome associated with a target RNA having a mutation (e.g., G>A mutation) in an individual, comprising introducing a dRNA or a construct comprising a nucleic acid encoding the dRNA into an isolated cell of the individual ex vivo, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating Joubert syndrome associated with a target RNA having a mutation (e.g., G>A mutation) in an individual, comprising introducing a dRNA or a construct comprising a nucleic acid encoding the dRNA into an isolated cell of the individual ex vivo, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating Joubert syndrome associated with a target RNA having a mutation (e.g., G>A mutation) in an individual, comprising introducing a construct comprising a nucleic acid encoding a dRNA into an isolated cell of the individual ex vivo, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the isolated cell. In some embodiments, the method comprises introducing the ADAR or a construct comprising a nucleic acid encoding the ADAR to the isolated cell. In some embodiments, the target RNA is AHI1$^{W725X}$ (e.g., 2174G>A). In some embodiments, the dRNA comprises the nucleic acid sequence of SEQ ID NO: 8 (5'-GUGAACGUCAAACUGUCGGAC-CAAUAUGGCAGAAUCUUCUCUCAUCUCAACUUUC CAUAUCCGUAUCAUGGAAUCAUAGCAUCCU-GUAACUACUAGCUCUCUUACAGCUG G-3').

In some embodiments, there is provided a method of treating or preventing Joubert syndrome with a target RNA having a mutation (e.g., G>A mutation) in an individual, comprising administering an effective amount of a dRNA or a construct comprising a nucleic acid encoding the dRNA to the individual, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating or preventing Joubert syndrome with a target RNA having a mutation (e.g., G>A mutation) in an individual, comprising administering an effective amount of a dRNA or a construct comprising a nucleic acid encoding the dRNA to the individual, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating or preventing Joubert syndrome with a target RNA having a mutation (e.g., G>A mutation) in an individual, comprising administering an effective amount of a construct comprising a nucleic acid encoding a dRNA to the individual, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase TI promoter ("Pol II promoter") operably linked to the nucleic acid encoding the dRNA.

In some embodiments, the ADAR is an endogenously expressed ADAR in the cells of the individual. In some embodiments, the method comprises administering the ADAR or a construct comprising a nucleic acid encoding the ADAR to the individual. In some embodiments, the target RNA is AHI1$^{W725X}$ (e.g., 2174G>A). In some embodiments, the dRNA comprises the nucleic acid sequence of SEQ ID NO: 8.

In some embodiments, there is provided a method of treating Fanconi anemia associated with a target RNA having a mutation (e.g., G>A mutation) in an individual, comprising introducing a dRNA or a construct comprising a nucleic acid encoding the dRNA into an isolated cell of the individual ex vivo, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating Fanconi anemia associated with a target RNA having a mutation (e.g., G>A mutation) in an individual, comprising introducing a dRNA or a construct comprising a nucleic acid encoding the dRNA into an isolated cell of the individual ex vivo, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating Fanconi anemia associated with a target RNA having a mutation (e.g., G>A mutation) in an individual, comprising introducing a construct comprising a nucleic acid encoding a dRNA into an isolated cell of the individual ex vivo, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the isolated cell. In some embodiments, the method comprises introducing the ADAR or a construct comprising a nucleic acid encoding the ADAR to the isolated cell. In some embodiments, the target RNA is FANCC$^{W506X}$ (e.g., 1517G>A). In some embodiments, the dRNA comprises the nucleic acid sequence of SEQ ID NO: 9 (5-GCCAAUGAUCUCGCUGAGUUAU-CUCAGCAGUGUGAGCCAUCAGGGUGAUGACAUC CCAGGCGAUCGUGUGUGCCUCCAG-GAGCCCAGAGCAGGAAGUUGAGGAGAAGGUG CCU-3').

In some embodiments, there is provided a method of treating or preventing Fanconi anemia with a target RNA having a mutation (e.g., G>A mutation) in an individual, comprising administering an effective amount of a dRNA or a construct comprising a nucleic acid encoding the dRNA to the individual, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating or preventing Fanconi anemia with a target RNA having a mutation (e.g., G>A mutation) in an individual, comprising administering an effective amount of a dRNA or a construct comprising a nucleic acid encoding the dRNA to the individual, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating or preventing Fanconi anemia with a target RNA having a mutation (e.g., G>A mutation) in an individual, comprising administering an effective amount of a construct comprising a nucleic acid encoding a dRNA to the individual, wherein the dRNA comprises a targeting RNA sequence that hybridizes to the target RNA, wherein the dRNA is capable of recruiting an ADAR to deaminate a target adenosine residue n the target RNA, and wherein the construct comprises a polymerase II promoter ("Pol II promoter") operably linked to the nucleic acid encoding the dRNA.

In some embodiments, the ADAR is an endogenously expressed ADAR in the cells of the individual. In some embodiments, the method comprises administering the ADAR or a construct comprising a nucleic acid encoding the ADAR to the individual. In some embodiments, the target RNA is FANCC$^{W506X}$ (e.g., 1517G>A). In some embodiments, the dRNA comprises the nucleic acid sequence of SEQ ID NO: 9.

In some embodiments, there is provided a method of treating primary familial hypertrophic cardiomyopathy associated with a target RNA having a mutation (e.g., G>A mutation) in an individual, comprising introducing a dRNA or a construct comprising a nucleic acid encoding the dRNA into an isolated cell of the individual ex vivo, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating primary familial hypertrophic cardiomyopathy associated with a target RNA having a mutation (e.g., G>A mutation) in an individual, comprising introducing a dRNA or a construct comprising a nucleic acid encoding the dRNA into an isolated cell of the individual ex vivo, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating primary familial hypertrophic cardiomyopathy associated with a target RNA having a mutation (e.g., G>A mutation) in an individual, comprising introducing a construct comprising a nucleic acid encoding a dRNA into an isolated cell of the individual ex vivo, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the isolated cell. In some embodiments, the method comprises introducing the ADAR or a construct comprising a nucleic acid encoding the ADAR to the isolated cell. In some embodiments, the target RNA is MYBPC3$^{W1098X}$ (e.g., 3293G>A). In some embodiments, the dRNA comprises the nucleic acid sequence of SEQ ID NO: 10 (5'-CAAGACGGUGAACCACUCCAUGGUC-UUCUUGUCGGCUUUCUGCACUGUGUACCCC CAGAGCUCCGUGUUGCCGACAUCCUGGGGUGGC-UUCCACUCCAGAGCACAUUAA G-3').

In some embodiments, there is provided a method of treating or preventing primary familial hypertrophic cardiomyopathy with a target RNA having a mutation (e.g., G>A mutation) in an individual, comprising administering an effective amount of a dRNA or a construct comprising a nucleic acid encoding the dRNA to the individual, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating or preventing primary familial hypertrophic cardiomyopathy with a target RNA having a mutation (e.g., G>A mutation) in an individual, comprising administering an effective amount of a dRNA or a construct comprising a nucleic acid encoding the dRNA to the individual, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating or preventing primary familial hypertrophic cardiomyopathy with a target RNA having a mutation (e.g., G>A mutation) in an individual, comprising administering an effective amount of a construct comprising a nucleic acid encoding a dRNA to the individual, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the cells of the individual. In some embodiments, the method comprises administering the ADAR or a construct comprising a nucleic acid encoding the ADAR to the individual. In some embodiments, the target RNA is MYBPC3$^{W1098X}$ (e.g., 3293G>A). In some embodiments, the dRNA comprises the nucleic acid sequence of SEQ ID NO: 10.

In some embodiments, there is provided a method of treating X-linked severe combined immunodeficiency associated with a target RNA having a mutation (e.g., G>A mutation) in an individual, comprising introducing a dRNA or a construct comprising a nucleic acid encoding the dRNA into an isolated cell of the individual ex vivo, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating X-linked severe combined immunodeficiency associated with a target RNA having a mutation (e.g., G>A mutation) in an individual, comprising introducing a dRNA or a construct comprising a nucleic acid encoding the dRNA into an isolated cell of the individual in vivo, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating X-linked severe combined immunodeficiency associated with a target RNA having a mutation (e.g., G>A mutation) in an individual, comprising introducing a construct comprising a nucleic acid encoding a dRNA into an isolated cell of the individual ex vivo, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the isolated cell. In some embodiments, the method comprises introducing the ADAR or a construct comprising a nucleic acid encoding the ADAR to the isolated cell. In some embodiments, the target RNA is IL2RG$^{W237X}$ (e.g., 710G-A). In some embodiments, the dRNA comprises the nucleic acid sequence of SEQ ID NO: 11 (5'-AGGAUUCUCUUUUGAAGUAUUG-CUCCCCCAGUGGAUUGGGUGGCUCCAUUCACUC CAAUGCUGAGCACUUCCACAGAGUGG-GUUAAAGCGGCLCCGAACACGAAACGUGU A-3').

In some embodiments, there is provided a method of treating or preventing X-linked severe combined immunodeficiency with a target RNA having a mutation (e.g, G>A mutation) in an individual, comprising administering an effective amount of a dRNA or a construct comprising a nucleic acid encoding the dRNA to the individual, wherein the dRNA comprises a targeting RNA sequence that hybridizes to a target RNA associated with the disease or condition, wherein the dRNA is capable of recruiting an ADAR to deaminate a target adenosine residue in the target RNA and wherein the dRNA is and wherein the dRNA is a circular RNA or capable of forming a circular RNA.

In some embodiments, there is provided a method of treating or preventing X-linked severe combined immunodeficiency with a target RNA having a mutation (e.g., G>A mutation) in an individual, comprising administering an effective amount of a dRNA or a construct comprising a nucleic acid encoding the dRNA to the individual, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a method of treating or preventing X-linked severe combined immunodeficiency with a target RNA having a mutation (e.g., G>A mutation) in an individual, comprising administering an effective amount of a construct comprising a nucleic acid encoding a dRNA to the individual, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the ADAR is an endogenously expressed ADAR in the cells of the individual. In some embodiments, the method comprises administering the ADAR or a construct comprising a nucleic acid encoding the ADAR to the individual. In some embodiments, the target RNA is IL2RG$^{W237X}$ (e.g., 710G>A). In some embodiments, the dRNA comprises the nucleic acid sequence of SEQ ID NO: 11.

Generally, dosages, schedules, and routes of administration of the compositions (e.g., dRNA or construct comprising a nucleic acid encoding dRNA) may be determined according to the size and condition of the individual, and according to standard pharmaceutical practice. Exemplary routes of administration include intravenous, intra-arterial, intraperitoneal, intrapulmonary, intravesicular, intramuscular, intra-tracheal, subcutaneous, intraocular, intrathecal, or transdermal.

The RNA editing methods of the present application not only can be used in animal cells, for example mammalian cells, but also may be used in modification of RNAs of plant or fungi, for example, in plants or fungi that have endogenously expressed ADARs. The methods described herein can be used to generate genetically engineered plant and fungi with improved properties.

Further provided are any one of the dRNAs, constructs, cells having edited RNA, and compositions described herein for use in any one of the methods of treatment described herein, and any one of the dRNAs, constructs, edited cells, and compositions described herein in the manufacture of a medicament for treating a disease or condition.

V. Compositions, Kits and Articles of Manufacture

Also provided herein are compositions (such as pharmaceutical compositions) comprising any one of the dRNAs, constructs, libraries, or host cells having edited RNA as described herein.

In some embodiments, there is provided a pharmaceutical composition comprising any one of the dRNAs or constructs encoding the dRNA described herein, and a pharmaceutically acceptable carriers, excipients or stabilizers (Remington's Pharmaceutical Sciences 16th edition, Osol. A. Ed. (1980)). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEE™, PLURONICS™ or polyethylene glycol (PEG). In some embodiments, lyophilized formulations are provided. Pharmaceutical compositions to be used for in vivo administration must be sterile. This is readily accomplished by, e.g., filtration through sterile filtration membranes.

Further provided are kits useful for any one of the methods of RNA editing or methods of treatment described herein, comprising any one of the dRNAs, constructs, compositions, libraries, or edited host cells as described herein.

In some embodiments, there is provided a kit for editing a target RNA in a host cell, comprising a dRNA or a construct comprising a nucleic acid encoding the dRNA, wherein the dRNA comprises a targeting RNA sequence that hybridizes to a target R N A associated with the disease or condition, wherein the dRNA is capable of recruiting an ADAR to deaminate a target adenosine residue in the target RNA and wherein the dRNA is and wherein the dRNA is a circular RNA of capable of forming a circular RNA.

In some embodiments, there is provided a kit for editing a target RNA in a host cell, comprising a dRNA or a construct comprising a nucleic acid encoding the dRNA, wherein the dRNA comprises a (1) targeting RNA sequence that hybridizes to the target RNA and (2) a small nucleolar RNA (snoRNA) sequence linked to the 3' and/or 5' ends of the targeting RNA sequence, and wherein the dRNA is capable of recruiting an ADAR to deaminate a target adenosine residue in the target RNA.

In some embodiments, there is provided a kit for editing a target RNA in a host cell, comprising or a construct comprising a nucleic acid encoding a dRNA, wherein the dRNA comprises a targeting RNA sequence that hybridizes to the target RNA, wherein the dRNA is capable of recruiting an ADAR to deaminate a target adenosine residue in the target RNA, and wherein the construct comprises a polymerase II promoter ("Pol II promoter") operably linked to the nucleic acid encoding the dRNA.

In some embodiments, the kit further comprises an ADAR or a construct comprising a nucleic acid encoding an ADAR. In some embodiments, the kit further comprises an inhibitor of ADAR3 or a construct thereof. In some embodiments, the kit further comprises a stimulator of interferon or a construct thereof. In some embodiments, the kit further comprises an instruction for carrying out any one of the RNA editing methods or methods of treatment described herein.

The kits of the present application are in suitable packaging. Suitable packaging includes, but is not limited to, vials, bottles, jars, flexible packaging (e.g., sealed Mylar or plastic bags), and the like. Kits may optionally provide additional components such as transfection or transduction reagents, cell culturing medium, buffers, and interpretative information.

The present application thus also provides articles of manufacture. The article of manufacture can comprise a container and a label or package insert on or associated with the container. Suitable containers include vials (such as sealed vials), bottles, jars, flexible packaging, and the like. In some embodiments, the container holds a pharmaceutical composition, and may have a sterile access port (for example, the container may be an intravenous solution bag or a vial having a stopper pierceable by a hypodermic injection needle). The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical compositions and instructions for use, packaged in quantities sufficient for storage and use in pharmacies, for example, hospital pharmacies and compounding pharmacies.

The exemplary embodiments and examples below are intended to be purely exemplary of the present application and should therefore not be considered to limit the invention in any way. The following exemplary embodiments and examples and detailed description are offered by way of illustration and not by way of limitation.

Exemplary Embodiments

The present application provides the following embodiments:
1. A method for editing a target RNA in a host cell, comprising introducing a deaminase-recruiting RNA (dRNA) or a construct comprising a nucleic acid encoding the dRNA into the host cell, wherein:
(1) the dRNA comprises a targeting RNA sequence that is at least partially complementary to the target RNA,
(2) the dRNA is capable of recruiting an adenosine deaminase acting on RNA (ADAR), and
(3) the dRNA is a circular RNA or capable of forming a circular RNA.
2. The method of embodiment 1, wherein the dRNA further comprises a 3' ligation sequence and a 5' ligation sequence.
3. The method of embodiment 2, wherein the 3' ligation sequence and the 5' ligation sequence are at least partially complementary to each other.
4. The method of embodiment 2 or embodiment 3, wherein the 3' ligation sequence and the 5' ligation sequence are about 20 to about 75 nucleotides in length.
5. The method of any one of embodiments 1-4, wherein the dRNA is circularized by RNA ligase RtcB.
6. The method of embodiment 4, wherein the RNA ligase RtcB is expressed endogenously in the host cell.
7. The method of any one of embodiments 1-6, wherein the dRNA is a circular RNA.
8. The method of any one of embodiments 1-6, wherein the dRNA is a linear RNA capable of forming a circular RNA.
9. The method of any one of embodiments 1-6, wherein the method comprises introducing a construct comprising a nucleic acid encoding the dRNA into the host cell.
10. The method of claim 9, wherein the construct further comprises a 3' twister ribozyme sequence linked to the 3' end of the nucleic acid encoding the dRNA and a 5' twister ribozyme sequence linked to the 5' end of the nucleic acid encoding the dRNA.
11. The method of embodiment 10, wherein the 3' twister sequence is twister P3 U2A and the 5' twister sequence is twister P1.
12. The method of embodiment 10, wherein the 5' twister sequence is twister P3 U2A and the 3' twister sequence is twister P1.
13. A method for editing a target RNA in a host cell, comprising introducing a deaminase-recruiting RNA (dRNA) or a construct comprising a nucleic acid encoding the dRNA into the host cell, wherein the dRNA comprises:
(1) a targeting RNA sequence that is at least partially complementary to the target RNA and
(2) a small nucleolar RNA (snoRNA) sequence linked to the 3' and/or 5' ends of the targeting RNA sequence;
and wherein the dRNA is capable of recruiting an adenosine deaminase acting on RNA (ADAR).
14. The method of embodiment 13, wherein the dRNA comprises a snoRNA sequence linked to the 5' end of the targeting RNA sequence ("5' snoRNA sequence").
15. The method of embodiment 13 or 14, wherein the dRNA comprises a snoRNA sequence linked to the 3' end of the targeting RNA sequence (3' snoRNA sequence").
16. The method of any one of embodiments 13-15, wherein the snoRNA sequence is at least about 70 nucleotides in length.
17. The method of any one of embodiments 13-16, wherein the 3' snoRNA sequence comprises the nucleic acid sequence of SEQ ID NO: 1.
18. The method of any one of embodiments 13-17, wherein the 5' snoRNA sequence comprises the nucleic acid sequence of SEQ ID NO: 2.
19. The method of any one of embodiments 13-18, wherein the snoRNA sequence is a C/D Box snoRNA sequence.
20. The method of any one of embodiments 13-18, wherein the snoRNA sequence is an H/ACA Box snoRNA sequence.
21. The method of any one of embodiments 13-18, wherein the snoRNA sequence is a composite C/ID Box and H/ACA Box snoRNA sequence.
22. The method of any one of embodiments 13-18, wherein the snoRNA sequence is an orphan snoRNA sequence.
23. The method of any one of embodiments 13-22, wherein the method comprises introducing a construct comprising a nucleic acid encoding the dRNA into the host cell.
24. The method of embodiment any one of embodiments 9-12 and 23, wherein the construct further comprises a promoter operably linked to the nucleic acid encoding the dRNA.
25. The method of embodiment 24, wherein the promoter is a polymerase II promoter ("Pol II promoter").
26. A method for editing a target RNA in a host cell, comprising introducing a construct comprising a nucleic acid encoding a deaminase-recruiting RNA (dRNA) into the host cell, wherein:
(1) the dRNA comprises a targeting RNA sequence that is at least partially complementary to the target RNA,
(2) the dRNA is capable of recruiting an adenosine deaminase acting on RNA (ADAR), and
(3) the construct comprises a polymerase II promoter ("Pol II promoter") operably linked to the nucleic acid encoding the dRNA.
27. The method of embodiment 25 or 26, wherein the Pol II promoter is a CMV promoter.
28. The method of embodiments 27, wherein the CMV promoter comprises the nucleic acid sequence of SEQ ID NO: 3.
29. The method of any one of embodiments 9-12 and 23-28, wherein the construct is a viral vector or a plasmid.
30. The method of embodiment 29, wherein the construct is an AAV vector.
31. The method of any one of embodiments 1-30, wherein the ADAR is endogenously expressed by the host cell.
32. The method of embodiment 31, wherein the host cell is a T cell.
33. The method of any one of embodiments 1-32, wherein the targeting RNA sequence is more than 5) nucleotides in length.
34. The method of embodiment 33, wherein the targeting RNA sequence is about 100 to about 150 nucleotides in length.
35. The method of any one of embodiments 1-34, wherein the targeting RNA sequence comprises a cytidine, adenosine or uridine directly opposite the target adenosine in the target RNA.
36. The method of embodiment 35, wherein the targeting RNA sequence comprises a cytidine mismatch directly opposite the target adenosine in the target RNA.
37. The method of embodiment 36, wherein the cytidine mismatch is located at least 20 nucleotides away from the 3' end of the targeting RNA sequence, and at least 5 nucleotides away from the 5' end of the targeting RNA sequence.

38. The method of any one of embodiments 1-37, wherein the targeting RNA sequence further comprises one or more guanosines each opposite a non-target adenosine in the target RNA.

39. The method of any one of embodiments 1-38, wherein the targeting RNA sequence comprises two or more consecutive mismatch nucleotides opposite a non-target adenosine in the target RNA.

40. The method of any one of embodiments 1-39, wherein the 5' nearest neighbor of the target adenosine in the target RNA is a nucleotide selected from U, C. A and G with the preference U>C≈A>G and the 3' nearest neighbor of the target adenosine in the target RNA is a nucleotide selected from G. C. A and U with the preference G>C>A≈U.

41. The method of any one of embodiments 1-40, wherein the target adenosine is in a three-base motif selected from the group consisting of UAG, UAC, UAA, UAU, CAG, CAC, CAA, CAU, AAG, AAC, AAA, AAU, GAG, GAC, GAA and GAU in the target RNA.

42. The method of embodiment 41, wherein the three-base motif is UAG, and wherein the targeting RNA comprises an A directly opposite the uridine in the three-base motif, a cytidine directly opposite the target adenosine, and a cytidine, guanosine or uridine directly opposite the guanosine in the three-base motif.

43. The method of any one of embodiments 1-42, wherein the target RNA is an RNA selected from the group consisting of a pre-messenger RNA, a messenger RNA, a ribosomal RNA, a transfer RNA, a long non-coding RNA and a small RNA.

44. The method of embodiment 43, wherein the target RNA is a pre-messenger RNA.

45. The method of any one of embodiments 1-44, further comprising introducing an inhibitor of ADAR3 and/or to the host cell.

46. The method of any one of embodiments 1-45, further comprising introducing a stimulator of interferon to the host cell.

47. The method of any one of embodiments 1-46, comprising introducing a plurality of dRNAs or constructs each targeting a different target RNA.

48. The method of any one of embodiments 1-47, wherein the efficiency of editing the target RNA is at least 40%.

49. The method of any one of embodiments 1-48, wherein the construct or the dRNA does not induce immune response.

50. The method of any one of embodiments 149, further comprising introducing an ADAR (e.g., exogenous ADAR) to the host cell.

51. The method of embodiment 50, wherein the ADAR is an ADAR1 comprising an E1008 mutation.

52. The method of any one of embodiments 1-51, wherein deamination of the target adenosine in the target RNA results in a missense mutation, an early stop codon, aberrant splicing, or alternative splicing in the target RNA, or reversal of a missense mutation, an early stop codon, aberrant splicing, or alternative splicing in the target RNA.

53. The method of embodiment 52, wherein deamination of the target adenosine in the target RNA results in point mutation, truncation, elongation and/or misfolding of the protein encoded by the target RNA, or a functional, full-length, correctly-folded and/or wild-type protein by reversal of a missense mutation, en early stop codon, aberrant splicing, or alternative splicing in the target RNA.

54. The method of any one of embodiments 1-53, wherein the host cell is a eukaryotic cell.

55. The method of embodiment 54, wherein the host cell is a mammalian cell.

56. The method of embodiment 55, wherein the host cell is a human or mouse cell.

57. An edited RNA or a host cell having an edited RNA produced by the method of any one of embodiments 1-56.

58. A method for treating or preventing a disease or condition in an individual, comprising editing a target RNA associated with the disease or condition in a cell of the individual according to the method of any one of the embodiments 1-57.

59. The method of embodiment 58, wherein the disease or condition is a hereditary genetic disease or a disease or condition associated with one or more acquired genetic mutations.

60. The method of embodiment 58 or 59, wherein the target RNA has a G to A mutation.

61. The method of any one of embodiments 58-60, wherein disease or condition is a monogenetic disease or condition.

62. The method of any one of embodiments 58-61, wherein the disease or condition is a polygenetic disease or condition.

63. The method of any one of embodiments 58-62, wherein:
   (i) the target RNA is TP53, and the disease or condition is cancer;
   (ii) the target RNA is IDUA, and the disease or condition is Mucopolysaccharidosis type I (MPS I);
   (iii) the target RNA is COL3A1, and the disease or condition is Ehlers-Danlos syndrome;
   (iv) the target RNA is BMPR2, and the disease or condition is Joubert syndrome;
   (v) the target RNA is FANCC, and the disease or condition is Fanconi anemia;
   (vi) the target RNA is MYBPC3, and the disease or condition is primary familial hypertrophic cardiomyopathy; or
   (vii) the target RNA is IL2RG, and the disease or condition is X-linked severe combined immunodeficiency.

64. A deaminase-recruiting RNA (dRNA) for editing a target RNA comprising a targeting RNA sequence that is at least partially complementary to the target RNA, wherein the dRNA is capable of recruiting an Adenosine Deaminase Acting on RNA (ADAR), and wherein the dRNA is circular or is capable of forming a circular RNA.

65. The dRNA of embodiment 64, wherein the dRNA further comprises a 3' ligation sequence and a 5' ligation sequence.

66. The dRNA of embodiment 65, wherein the 3' ligation sequence and the 5' ligation sequence are at least partially complementary to each other.

67. The dRNA of embodiment 65 or 66, wherein the 3' ligation sequence and the 5' ligation sequence are about 20 to about 75 nucleotides in length.

68. The dRNA of any one of embodiments 64-67, wherein the dRNA is a circular RNA.

69. The dRNA of any one of embodiments 64-67, wherein the dRNA is a linear RNA capable of forming a circular RNA.

70. A construct comprising a nucleic acid encoding the dRNA of any one of embodiments 64-69.

71. The construct of embodiment 70, wherein the construct further comprises a 3' twister ribozyme sequence linked to the 3' end of the nucleic acid encoding the dRNA and a 5' twister ribozyme sequence linked to the 5' end or the nucleic acid encoding the dRNA.

72. The construct of embodiment 71, wherein the 3' twister sequence is twister P3 U2A and the 5' twister sequence is twister P1.

73. The construct of embodiment 72, wherein the 5' twister sequence is twister P3 U2A and the 3' twister sequence is twister P1.

74. A deaminase-recruiting RNA (dRNA) for editing a target RNA comprising:
(1) a targeting RNA sequence that is at least partially complementary to the target RNA and
(2) a small nucleolar RNA (snoRNA) sequence at the 3' and/or 5' ends of the targeting RNA sequence;
wherein the dRNA is capable of recruiting an adenosine deaminase acting on RNA (ADAR).

75. The dRNA of embodiment 74, wherein the dRNA comprises a snoRNA sequence linked to the 5' end of the targeting RNA sequence ("5' snoRNA sequence").

76. The dRNA of embodiment 75, wherein the dRNA comprises a snoRNA sequence linked to the 3' end of the targeting RNA sequence (3' snoRNA sequence").

77. The dRNA of any one of embodiments 74-76, wherein the snoRNA sequence is at least about 70 nucleotides in length.

78. The dRNA of any one of embodiments 76-77, wherein the 3' snoRNA sequence comprises the nucleic acid sequence of SEQ ID NO: 1.

79. The dRNA of any one of embodiments 75-78, wherein the 5' snoRNA sequence comprises the nucleic acid sequence of SEQ ID NO: 2.

80. The dRNA of any one of embodiments 74-79, wherein the snoRNA sequence is a C/D Box snoRNA sequence.

81. The dRNA of any one of embodiments 74-79, wherein the snoRNA sequence is an H/ACA Box snoRNA sequence.

82. The dRNA of any one of embodiments 74-79, wherein the snoRNA sequence is a composite C/D Box and H/ACA Box snoRNA sequence.

83. The dRNA of any one of embodiments 74-79, wherein the snoRNA sequence is an orphan snoRNA sequence.

84. A construct comprising a nucleic acid encoding a dRNA of any one of embodiments 74-83.

85. The construct of any one of embodiments 70-73 and 84, wherein the construct further comprises a promoter operably linked to the nucleic acid encoding the dRNA.

86. The construct of embodiment 95, wherein the promoter is a polymerase II promoter ("Pol II promoter").

87. A construct comprising a nucleic acid encoding a deaminase-recruiting RNA (dRNA) into the host cell, wherein:
(1) the dRNA comprises a targeting RNA sequence that is at least partially complementary to the target RNA,
(2) the dRNA is capable of recruiting an adenosine deaminase acting on RNA (ADAR), and
(3) the construct comprises a polymerase II promoter ("Pol II promoter") operably linked to the nucleic acid encoding the dRNA.

88. The construct of embodiment 86 or 87, wherein the Pol II promoter is a CMV promoter.

89. The construct of embodiment 88, wherein the CMV promoter comprises the nucleic acid sequence of SEQ ID NO: 3.

90. The construct of any one of embodiments 70-73 and 84-89, wherein the construct is a viral vector or a plasmid.

91. The construct of embodiment 90, wherein the construct is an AAV vector.

92. The construct or dRNA of any one of embodiments 64-91, wherein the target RNA is an RNA selected from the group consisting of a pre-messenger RNA, a messenger RNA, a ribosomal RNA, a transfer RNA, a long non-coding RNA and a small RNA.

93. A host cell comprising the construct or dRNA of any one of embodiments 64-91.

94. A kit for editing a target RNA in a host cell comprising the construct or dRNA of any one of embodiments 64-91.

EXAMPLE

Materials and Methods
Plasmids Construction

The dual fluorescence reporter was cloned by PCR amplifying mCherry and EGFP (the EGFP first codon ATG was deleted) coding DNA, the 3×GS linker and targeting DNA sequence were added via primers during PCR. Then the PCR products were cleaved and linked by Type IIs restriction enzyme BsmBI (Thermo) and T4 DNA ligase (NEB), which then were inserted into pLenti backbone (pLenti-CMV-MCS-SV-Bsd, Stanley Cohen Lab, Stanford University).

The dLbuCas13 DNA was PCR amplified from the Lbu plasmids (Addgene #83485). The ADAR1DD and ADAR2DD were amplified from Adar1(p150) cDNA and Adar2 cDNA, both of which were gifts from Han's lab at Xiamen University. The ADAR1DD or ADAR2DD were fused to dLbuCas13 DNA by overlap-PCR, and the fused PCR products were inserted into pLenti backbone.

For expression of dRNA in mammalian cells, the dRNA sequences were directly synthesized (for short dRNAs) and annealed or PCR amplified by synthesizing overlapping cDNA, and the products were cloned into the corresponding vectors under U6 expression by Golden-gate cloning.

The full length Adar1(p110) and Adar1(p150) were PCR amplified from Adar1(p150) cDNA, and the full length Adar2 were PCR amplified from Adar2 cDNA, which were then cloned into pLenti backbone, respectively.

For the two versions of dual fluorescence reporters (Reporter-1 and -3), mCherry and EGFP (the start codon ATG of EGFP was deleted) coding sequences were PCR amplified, digested using BsmBI (Thermo Fisher Scientific, ER0452), followed by T4 DNA ligase (NEB. M0202L)-mediated ligation with GGGGS linkers. The ligation product was subsequently inserted into the pLenti-CMV-MCS-PURO backbone.

For the dLbuCas13-ADAR$_{DD}$ (E1008Q) expressing construct, the ADAR1 on gene was amplified from the ADAR1$^{p150}$ construct (a gift from Jiahuai Han's lab, Xiamen University). The dLbuCas13 gene was amplified by PCR from the Lbu_C2c2_R472A_H477A_R1048A_H1053A plasmid (Addgene #83485). The ADAR1$_{DD}$ (hyperactive E1008Q variant) was generated by overlap-PCR and then fused to dLbuCas13. The ligation products were inserted into the pLenti-CMV-MCS-BSD backbone.

For arRNA-expressing construct, the sequences of arRNAs were synthesized and golden-gate cloned into the pLenti-sgRNA-lib 2.0 (Addgene #89638) backbone, and the transcription of arRNA was driven by hU6 promoter. For the ADAR expressing constructs, the full length ADAR1$^{p110}$ and ADAR1$^{p150}$ were PCR amplified from the ADAR1$^{p150}$ construct, and the full length ADAR2 were PCR amplified from the ADAR2 construct (a gift from Jiahuai Han's lab. Xiamen University). The amplified products were then cloned into the pLenti-CMV-MCS-BSD backbone.

For the constructs expressing genes with pathogenic mutations, full length coding sequences of TP53 (ordered from Vigenebio) and other 6 disease-relevant genes (COL3A1. BMPR2, AHI1, FANCC, MYBPC3 and IL2RG, gifts from Jianwei Wang's lab. Institute of pathogen biology, Chinese Academy of Medical Sciences) were amplified from the constructs encoding the corresponding genes with introduction of G>A mutations through mutagenesis PCR. The amplified products were cloned into the pLenti-CMV-MCS-mCherry backbone through Gibson cloning method.

Mammalian Cell Lines and Cell Culture

Mammalian cell lines were cultured Dulbecco's Modified Eagle Medium (10-013-CV, Corning, Tewksbury, Mass., USA), adding 10% fetal bovine serum (Lanzhou Bailing Biotechnology Co., Ltd., Lanzhou, China), supplemented with 1% penicillin streptomycin under 5% $CO_2$ at 37° C. The Adar1-KO cell line was purchased from EdiGene China, and the genotyping results were also provided by EdiGene China.

The HeLa and B16 cell lines were from Z. Jiang's laboratory (Peking University). And the HEK293T cell line was from C. Zhang's laboratory (Peking University). RD cell line was from J Wang's laboratory (Institute of Pathogen Biology, Peking Union Medical College & Chinese Academy of Medical Sciences). SF268 cell lines were from Cell Center. Institute of Basic Medical Sciences, Chinese Academy of Medical Sciences. A549 and SW13 cell lines were from EdiGene Inc. HepG2, HT29, NIH3T3, and MEF cell lines were maintained in our laboratory at Peking University. These mammalian cell lines were cultured in Dulbecco's Modified Eagle Medium (Corning, 10-013-CV) with 10% fetal bovine serum (CellMax, SA201.02), additionally supplemented with 1% penicillin streptomycin under 5% $CO_2$ at 37° C. Unless otherwise described, cells were transfected with the X-tremeGENE HP DNA transfection reagent (Roche, 06366546001) according to the manufacturer's instruction.

The human primary pulmonary fibroblasts (#3300) and human primary bronchial epithelial cells (#3210) were purchased from ScienCell Research Laboratories, Inc. and were cultured in Fibroblast Medium (ScienCell, #2301) and Bronchial Epithelial Cell Medium (ScienCell, #3211), respectively. Both media were supplemented with 15% fetal bovine serum (BI) and 1% penicillin-streptomycin. The primary GM06214 and GM01323 cells were ordered from Coriell Institute for Medical Research and cultured in Dulbecco's Modified Eagle Medium (Corning, 10-013-CV) with 15% fetal bovine serum (BI) and 1% penicillin-streptomycin. All cells were cultured under 5% $CO_2$ at 37° C.

Reporter System Transfection, FACS Analysis and Sanger Sequencing

For dual fluorescence reporter editing experiments, 293T-WT cells or 293T-Adar1-KO cells were seeded in 6 wells plates ($6\times10^5$ cells/well), 24 hours later, 1.5 μg reporter plasmids and 1.5 μg dRNA plasmids were co-transfected using the X-tremeGENE HP DNA transfection reagent (06366546001; Roche, Mannheim, German), according to the supplier's protocols, 48 to 72 hours later, collected cells and performed FACS analysis. For further confirming the reporter mRNA editing, we sorted the EGFP-positive cells from 293T-WT cells transfected with reporter and dRNA plasmids using a FACS Aria flow cytometer (BD Biosciences), followed by total RNA isolation (TIANGEN, DP430). Then the RNA was reverse-transcribed into cDNA via RT-PCR (TIANGEN, KR103-04), and the targeted locus were PCR amplified with the corresponding primer pairs (23 PCR cycles) and the PCR products were purified for Sanger sequencing.

For Adar1(p110). Adar1(p150) or Adar2 rescue and over-expression experiments, 293T-WT cells or 293T-Adar1-KO cells were seeded in 12 wells plates ($2.5\times10^{-5}$ cells/well), 24 hours later, 0.5 μg reporter plasmids, 0.5 μg dRNA plasmids and 0.5 μg Adar1/2 plasmids (pLenti backbone as control) were co-transfected using the X-treneGENE HP DNA transfection reagent (06366546001, Roche, Mannheim, German). 48 to 72 hours later, collected cells and performed FACS analysis.

For endogenous mRNA experiments, 293T-WT cells were seeded in 6 wells plates ($6\times10^5$ cells/well), When approximately 70% confluent, 3 jig dRNA plasmids were transfected using the X-tremeGENE HP DNA transfection reagent (06366546001, Roche, Mannheim, German). 72 hours later, collected cells and sorted GFP-positive or BFP-positive cells (according to the corresponding fluorescence maker) via FACS for the following RNA isolation.

Isolation and Culture of Human Primary T Cells

Primary human T cells were isolated from leukapheresis products from healthy human donor. Briefly, Peripheral blood mononuclear cells (PBMCs) were isolated by Ficoll centrifugation (Dakewei, AS1114546), and T cells were isolated by magnetic negative selection using an EasySep Human T Cell Isolation Kit (STEMCELL, 17951) from PBMCs. After isolation. T cells were cultured in X-vivo15 medium, 10% FBS and IL2 (100 U/ml) and stimulated with CD3/CD28 DynaBeads (ThermoFisher, 11131D) for 2 days. Leukapheresis products from healthy donors were acquired from AllCells LLC China. All healthy donors provided informed consent.

Lenti-Virus Package and Reporter Cells Line Construction

The expression plasmid was co-transfected into HEK293T-WT cells, together with two viral packaging plasmids, pR8.74 and pVSVG (Addgene) via the X-tremeGENE HP DNA transfection reagent, 72 hours later, the supernatant virus was collected and stored at −80° C. The HEK293T-WT cells were infected with lenti-virus, 72 hours later, mCherry-positive cells were sorted via FACS and cultured to select a single clone cell lines stably expressing dual fluorescence reporter system with much low EGFP background by limiting dilution method.

For the stable reporter cell lines, the reporter constructs (pLenti-CMV-MCS-PURO backbone) were co-transfected into HEK293T cells, together with two viral packaging plasmids, pR8.74 and pVSVG. 72 hours later, the supernatant virus was collected and stored at −80° C. The HEK293T cells were infected with lentivirus, then mCherry-positive cells were sorted via FACS and cultured to select a single clone cell lines stably expressing dual fluorescence reporter system without detectable EGFP background. The HEK293T ADAR1 and 1P53 cell lines were generated according to a previously reported method[60]. ADAR1-targeting sgRNA and PCR amplified donor DNA containing CMV-driven puromycin resistant gene were co-transfected into HEK293T cells. Then cells were treated with puromycin 7 days after transfection. Single clones were isolated from puromycin resistant cells followed by verification through sequencing and Western blot.

RNA Editing of Endogenous or Exogenous-Expressed Transcripts

For assessing RNA editing on the dual fluorescence reporter, HEK293T cells or HEK293T ADAR1$^{-/-}$ cells were seeded in 6-well plates ($6\times10^5$ cells/well). 24 hours later, cells were co-transfected with 1.5 μg reporter plasmids and 1.5 μg arRNA plasmids. To examine the effect of ADAR1$^{P110}$, ADAR1$^{P150}$ or ADAR2 protein expression, the editing efficiency was assayed by EGFP positive ratio and deep sequencing.

HEK293T ADAR1$^{-/-}$ cells were seeded in 12-well plates ($2.5\times10^5$ cells/well). 24 hours later, cells were co-transfected with 0.5 μg of reporter plasmids, 0.5 μg arRNA plasmids and 0.5 µg ADAR1/2 plasmids (pLenti backbone as control). The editing efficiency was assayed by EGFP positive ratio and deep sequencing.

To assess RNA editing on endogenous mRNA transcripts, HEK293T cells were seeded in 6-well plates ($6 \times 10^5$ cells/well). Twenty-four hours later, cells were transfected with 3 µg of arRNA plasmids. The editing efficiency was assayed by deep sequencing.

To assess RNA editing efficiency in multiple cell lines, 8-9×104 (RD, SF268, HeLa) or $1.5 \times 10^5$ (HEK293T) cells were seeded in 12-well plates. For cells difficult to transfect, such as HT29, A549, HepG2, SW13, NIH3T3, MEF and B16, $2\text{-}2.5 \times 10^5$ cells were seeded in 6-well plate. Twenty-four hours later, reporters and arRNAs plasmid were co-transfected into these cells. The editing efficiency was assayed by EGFP positive ratio.

To evaluate EGFP positive ratio, at 48 to 72 hrs post transfection, cells were sorted and collected by Fluorescence-activated cell sorting (FACS) analysis. The mCherry signal was served as a fluorescent selection marker for the reporter/arRNA-expressing cells, and the percentages of EGFP+/mCherry+ cells were calculated as the readout for editing efficiency.

For NGS quantification of the A to I editing rate, at 48 to 72 hr post transfection, cells were sorted and collected by FACS assay and were then subjected to RNA isolation (TIANGEN, DP420). Then, the total RNAs were reverse-transcribed into cDNA via RT-PCR (TIANGEN, KR103-04), and the targeted locus was PCR amplified with the corresponding primers listed in

| Name of Primer | Sequence (5'--->3') |
|---|---|
| mCherry-SpeI-F | TATAACTAGTATGGTGAGCAAGGGCGAGGAG (SEQ ID NO: 12) |
| mCherry-BsmBI-R1 | TATACGTCTCATCTACAGATTCTTCCGGCGTGTATACCTTC (SEQ ID NO: 13) |
| EGFP-BsmB1-F1 | TATACGTCTCATAGAGATCCCCGGTCGCCACCGTGAGCAAGGGCGAGGAGCTG (SEQ ID NO: 14) |

The PCR products were purified for Sanger sequencing or NGS (Illumina HiSeq X Ten).

Testing in Multiple Cell Lines

Besides HEK293T (positive control) and HEK293T ADAR1$^{-/-}$ (negative control) cells, one mouse cell line (NIH3T3) as well as seven human cell lines (RD, HeLa, SF268, A549. HepG2. HT-29, SW13) originating from different tissues and organs were selected to perform the experiment. For the cell lines with higher transfection efficiency, about $8\text{-}9 \times 10^4$ cells (RD, HeLa, SF268) or $1.5 \times 10^5$ (HEK293T) were plated onto each well of 12-well plate, as for the ones (A549, HepG2, HT-29, SW13, NIH3T3) which are difficult to transfect, $2\text{-}2.5 \times 10^5$ cells were plated in 6-well plate. And all these cells were maintained in Dulbecco's modified Eagle's medium (DMEM, Corning) supplemented with 10% fetal bovine serum (FBS, CellMax) with 5% $CO_2$ in 37° C. 24 hrs later, CG2 reporter and 71nt dRNA (35-C-35) plasmid were co-transfected into different type of cells with X-tremeGENE HP DNA transfection reagent (Roche). 48 hrs after transfection, cells were trypsinized and analyzed through FACS (BD). Because the cells with low transfection efficiency had quite fewer mCherry and BFP positive cells, we increased the total cell number for FACS analysis to $1 \times 10^5$ for those cells plated onto 6-well plate.

Example 1. Optimizing LEAPER by Using a CMV Promoter to Drive arRNA Expression

To test whether an RNA Polymerase II (Pol II) can improve editing efficiency, a plasmid expressing arRNA driven by a Pol II promoter (CMV) was constructed. Using a reporter system based on EGFP expression (Reporter 1, FIG. 4B), the RNA editing efficiency between arRNAs driven by CMV and U6 promoters was compared (arRNA$_{53}$). Untreated cells were used as a mock control (Mock). Cells transfected with a non-targeting RNA were also used as a control (Ctrl RNAs). It was found that CMV-arRNA outperforms U6-arRNA in RNA editing (FIG. 1).

| Name of Primer | Sequence (5'--->3') |
|---|---|
| Ctrl RNA51 | UAAACCGAGGGAUCAUAGGGGACUGAAUCCACCAUUCUUCUCCCAAUCCCU (SEQ ID NO: 15) |
| Ctrl RNA151 | ACUACAGUUGCUCCGAUAUUUAGGCUACGUCAAUAGGCACUAACUUAUUGGCGCUGGUGAACGGACUUCCUCUCGAGUACCAGAAGAUGACUACAAAACUCCUUUCCAUUGCGAGUAUCGGAGUCUGGCUCAGUUUGGCCAGGGAGGCACU (SEQ ID NO: 16) |
| arRNA$_{51}$ | GCCCTTGCTCACTGGCAGAGCCCTCCAGCATCGCGAGCAGGCGCTGCCTCC (SEQ ID NO: 17) |
| arRNA$_{151}$ | ACUACAGUUGCUCCGAUAUUUAGGCUACGUCAAUAGGCACUAACUUAUUGGCGCUGGUGAACGGACUUCCUCUCGAGUACCAGAAGAUGACUACAAAACUCCUUUCCAUUGCGAGUAUCGGAGUCUGGCUCAGUUUGGCCAGGGAGGCACU (SEQ ID NO: 18) |

Example 2. RNA Editing Mediated by sno-arRNA

Figure 2A:
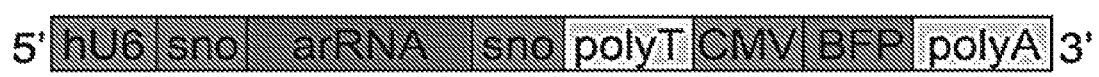
FIGS. 2A-2C depict Sno-arRNA$_{151}$ flanked by snoRNA ends mediated targeted RNA editing on Reporter mRNA.

In order to stabilize arRNAs and enhance its nuclear localization, arRNA was engineered to have snoRNA ends. The 151-nt arRNA targeting fluorescence Reporter-1 was flanked with snoRNA ends (FIG. 2A):

5' end:

(SEQ ID NO: 19)
GAGTGAGATCTTGGACCAATGATGACTTCCATACATGCATTCCTTGGAAA

GCTGAACAAAATGAGTGGGAACTCTGTACTATCATCTTAGTTGAACTGAG

GTCCACCGGGGCTAA;

3' end:

(SEQ ID NO: 20)
AAGATTGTGTGTGGATCGATGATGACTTCCATATATACATTCCTTGGAAA

GCTGAACAAAATGAGTGAAAACTCTATACCGTCATTCTCGTCGAACTGAG

GTCCAGCACATTACTCCAACAG, named sno-arRNA151.

Dual fluorescence reporter-1 comprises sequence of mCherry (SEQ ID NO: 21), sequence comprising 3×GS linker and the targeted A (SEQ ID NO: 22), and sequence of eGFP (SEQ ID NO: 23).

(SEQ ID NO: 21)
ATGGTGAGCAAGGGCGAGGAGGATAACATGGCCATCATCAAGGAGTTCAT

GCGCTTCAAGGTGCACATGGAGGGCTCCGTGAACGGCCACGAGTTCGAGA

TCGAGGGCGAGGGCGAGGGCCGCCCCTACGAGGGCACCCAGACCGCCAA

GCTGAAGGTGACCAAGGGTGGCCCCCTGCCCTTCGCCTGGGACATCCTGT

CCCCTCAGTTCATGTACGGCTCCAAGGCCTACGTGAAGCACCCCGCCGAC

ATCCCCGACTACTTGAAGCTGTCCTTCCCCGAGGGCTTCAAGTGGGAGCG

CGTGATGAACTTCGAGGACGGCGGCGTGGTGACCGTGACCCAGGACTCCT

CCCTGCAGGACGGCGAGTTCATCTACAAGGTGAAGCTGCGCGGCACCAAC

TTCCCCTCCGACGGCCCCGTAATGCAGAAGAAGACCATGGGCTGGGAGGC

CTCCTCCGAGCGGATGTACCCCGAGGACGGCGCCCTGAAGGGCGAGATCA

AGCAGAGGCTGAAGCTGAAGGACGGCGGCCACTACGACGCTGAGGTCAAG

ACCACCTACAAGGCCAAGAAGCCCGTGCAGCTGCCCGGCGCCTACAACGT

CAACATCAAGTTGGACATCACCTCCCACAACGAGGACTACACCATCGTGG

AACAGTACGAACGCGCCGAGGGCCGCCACTCCACCGGCGGCATGGACGAG

CTGTACAAG
(sequence of mCherry)

(SEQ ID NO: 22)
CTGCAG*GGCGGAGGAGGCAGCGGCGGAGGAGGCAGCGGCGGAGGAGGCAGC*

AGAAGGTATACACGCCGGAAGAATCTGTAGAGATCCCCGGTCGCCACC
(sequence comprising 3 × GS linker (shown as
italic and bold characters) and the targeted A
(shown as larger and bold A))

(SEQ ID NO: 23)
GTGAGCAAGGGCGAGGAGCTGTTCACCGGGGTGGTGCCCATCCTGGTCGA

GCTGGACGGCGACGTAAACGGCCACAAGTTCAGCGTGTCCGGCGAGGGCG

AGGGCGATGCCACCTACGGCAAGCTGACCCTGAAGTTCATCTGCACCACC

GGCAAGCTGCCCGTGCCCTGGCCCACCCTCGTGACCACCCTGACCTACG

GCGTGCAGTGCTTCAGCCGCTACCCCGACCACATGAAGCAGCACGACTTC

TTCAAGTCCGCCATGCCCGAAGGCTACGTCCAGGAGCGCACCATCTTCTT

CAAGGACGACGGCAACTACAAGACCCGCGCCGAGGTGAAGTTCGAGGGCG

ACACCCTGGTGAACCGCATCGAGCTGAAGGGCATCGACTTCAAGGAGGAC

GGCAACATCCTGGGGCACAAGCTGGAGTACAACTACAACAGCCACAACGT

CTATATCATGGCCGACAAGCAGAAGAACGGCATCAAGGTGAACTTCAAGA

TCCGCCACAACATCGAGGACGGCAGCGTGCAGCTCGCCGACCACTACCAG

CAGAACACCCCCATCGGCGACGGCCCCGTGCTGCTGCCCGACAACCACTA

CCTGAGCACCCAGTCCGCCCTGAGCAAAGACCCCAACGAGAAGCGCGATC

ACATGGTCCTGCTGGAGTTCGTGACCGCCGCGGGATCACTCTCGGCAT

GGACGAGCTGTACAAGTAA (sequence of eGFP).

Figure 2B:
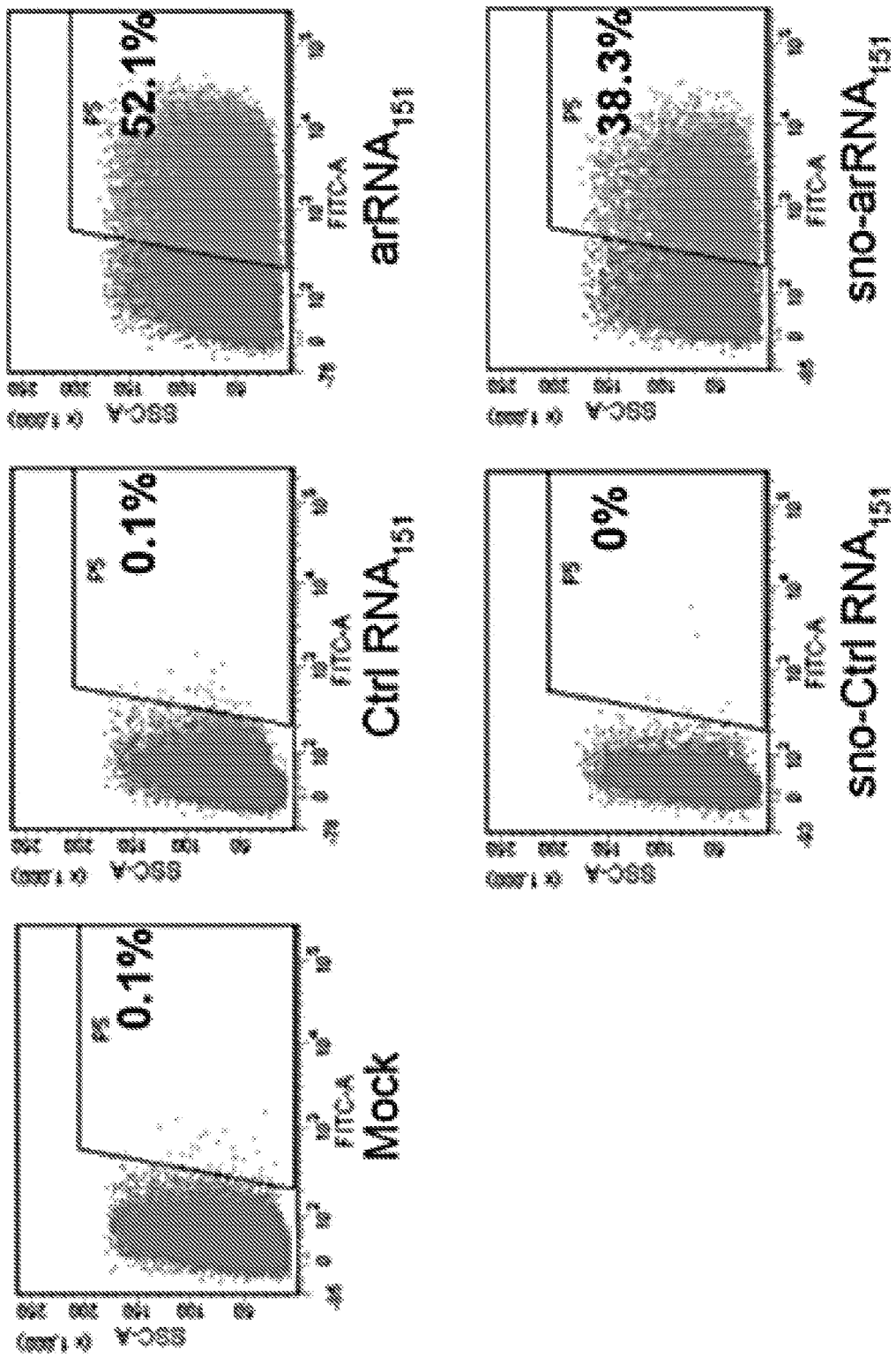
Figure 2C:
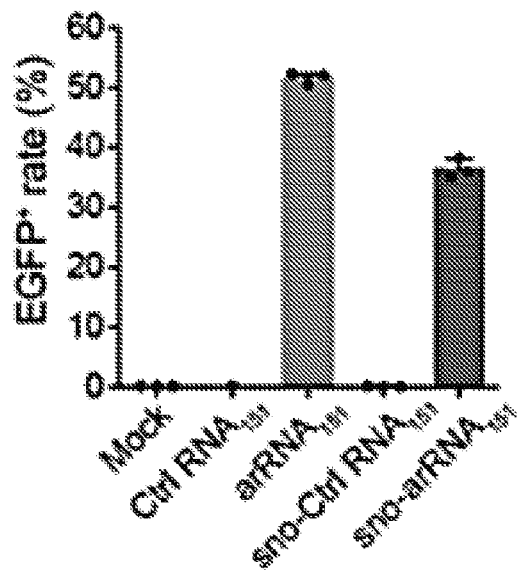

Then the human U6-drived sno-arRNA151, arRNA151, sno-Ctrl RNA151 or Ctrl RNA151 was transfected into HEK293T cells along with Reporter-expressing plasmids. Forty-eight hours post transfection, the EGFP positive rate was quantified via FACS analysis. The FACS results showed sno-arRNA151 flanked by snoRNA ends could mediated targeted RNA editing on Reporter mRNA with almost 38% EGFP positive rate, lower than that of the linear arRNAs (FIGS. 2B-2C).

Figure 3A:
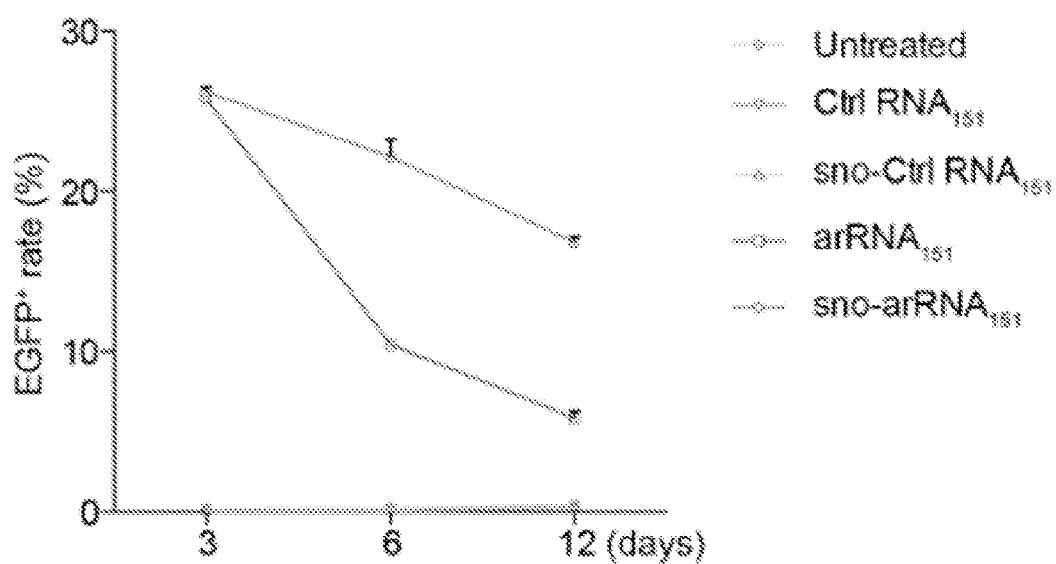
FIGS. 3A-3C depict editing efficacy with CMV-promoter expressed sno-arRNA and hU6 promoter expressed sno-arRNA.

To test if snoRNA ends stabilize the arRNA, the EGPF positive rate was measured at different timepoints. The sno-arRNA$_{151}$, arRNA$_{151}$, sno-Ctrl RNA$_{151}$ or Ctrl RNA$_{151}$ under human U6 promoter were transfected into HEK293T-Reporter cells. The EGFP positive rate was measured at 3 times points: 3 days, 6 days and 12 days post transfection. The results showed that sno-arRNA exhibited higher editing efficiency than arRNA during the extended time period, indicating that snoRNA ends could protect arRNA from degradation and enhance the abundance of sno-arRNA (FIG. 3A).

Figure 3B:
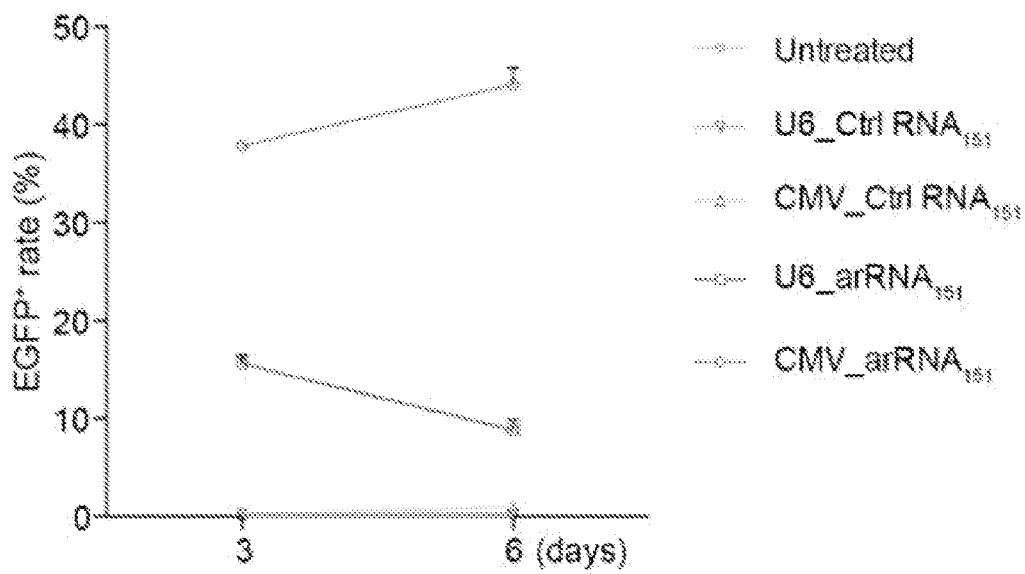
Figure 3C:
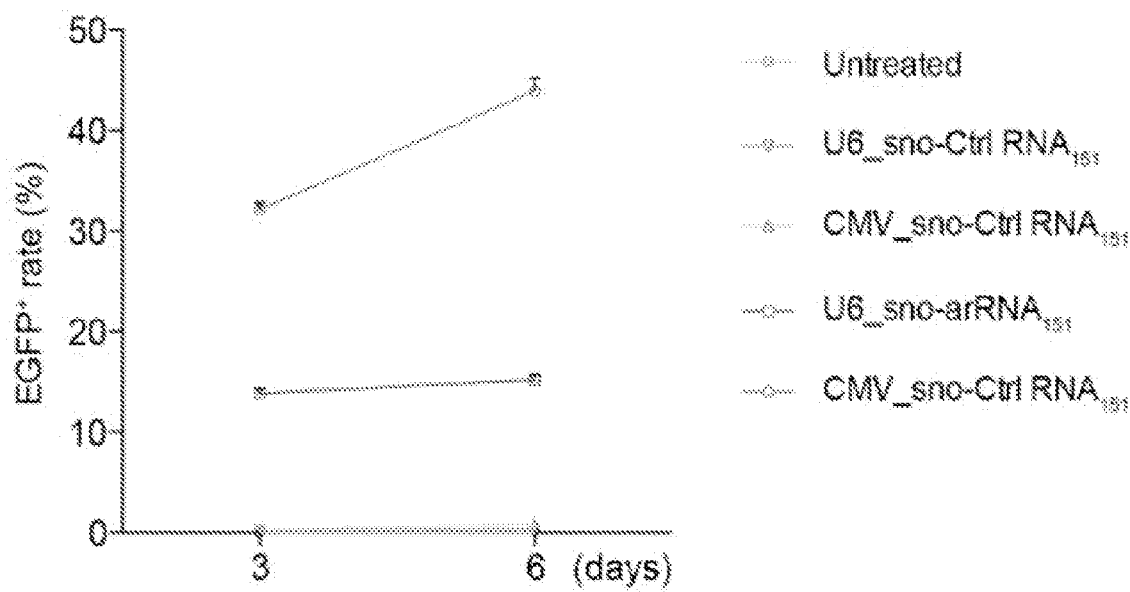

To further enhance the expression level of arRNA, a virus-based strong promoter-CMV was used to express arRNA or sno-arRNA. The results showed that CMV-promoter expressed arRNA (CMV_arRNA) exhibited much higher editing efficiency than U6-promoter expressed arRNA (U6_arRNA). Besides, the EGFP positive rate of U6_arRNA group declined with prolonged time, while the EGFP positive rate of CMV_arRNA still increased at 6 days post transfection. Similarly, CMV-promoter expressed sno-arRNA (CMV_sno-arRNA) achieved much higher editing efficiency than U6-promoter expressed sno-arRNA (U6_sno-arRNA) (FIG. 3B and FIG. 3C).

Based on the above results, it was demonstrated that snoRNA ends could stabilize arRNA, and arRNA or sno-arRNA driven by CMV promoter could increase its expression level. Both of these two strategy could significantly boost the editing efficiency of arRNA.

Example 3. RNA Editing Mediated by Circular arRNA

Figure 4A:
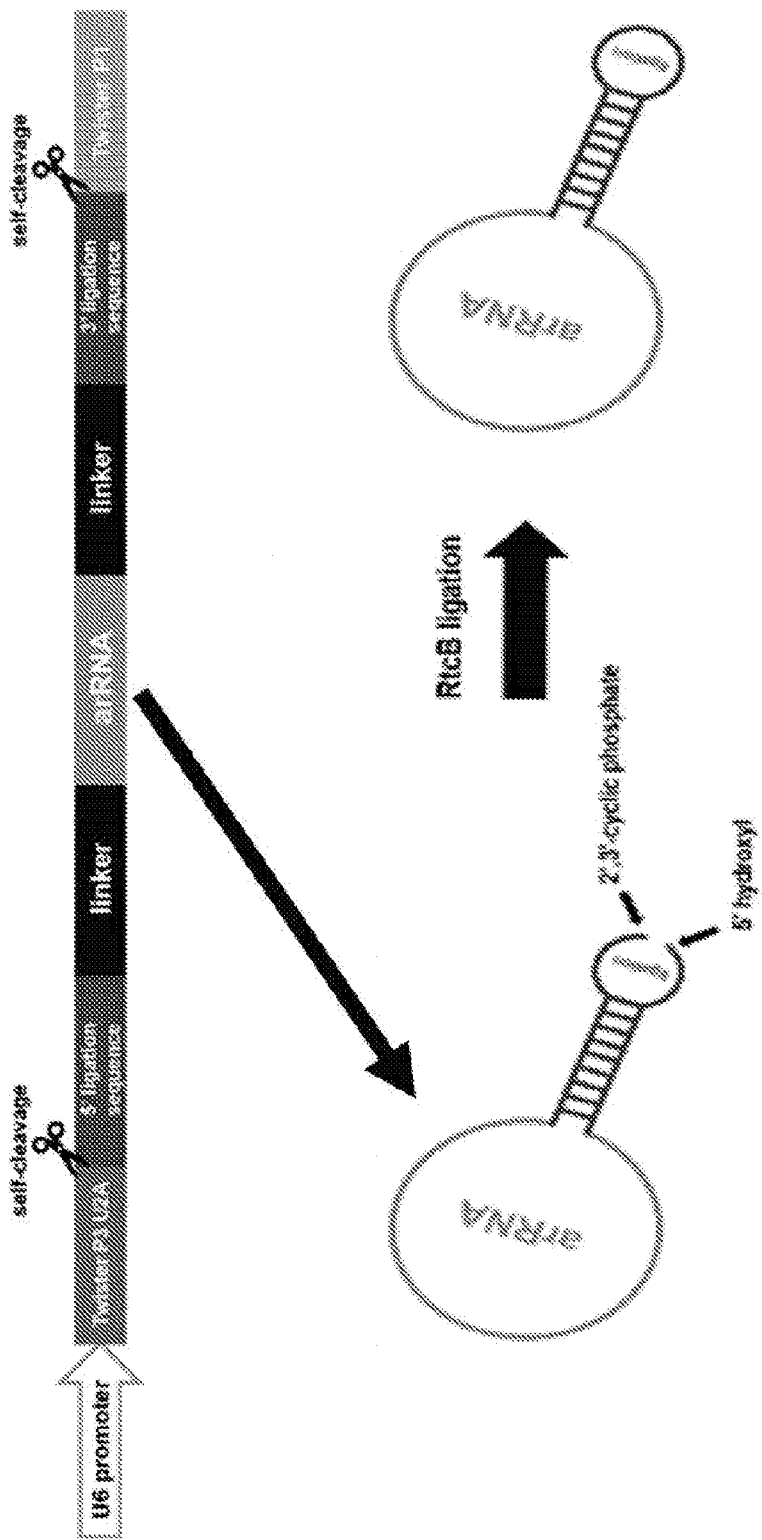
Figure 4B:
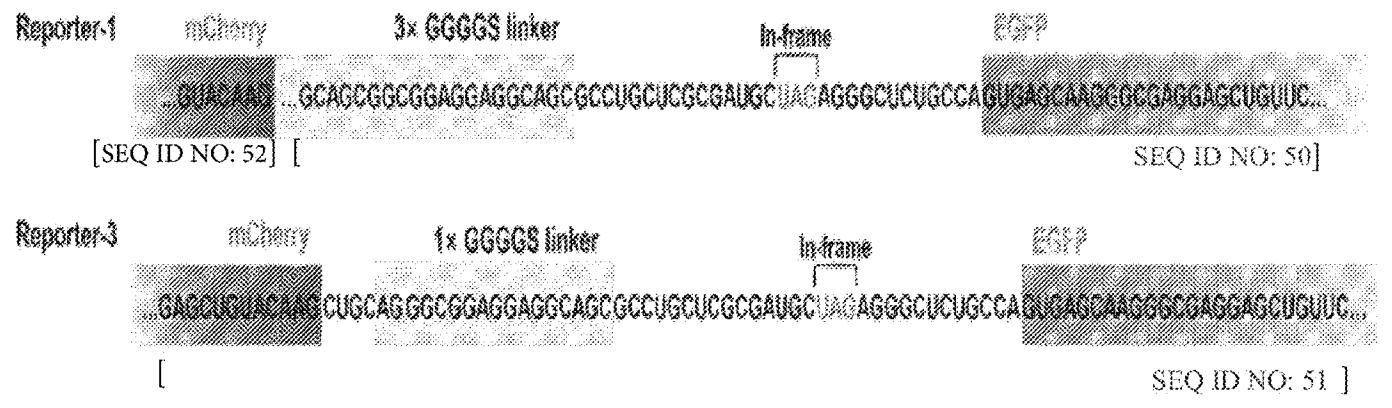
Figure 4C:
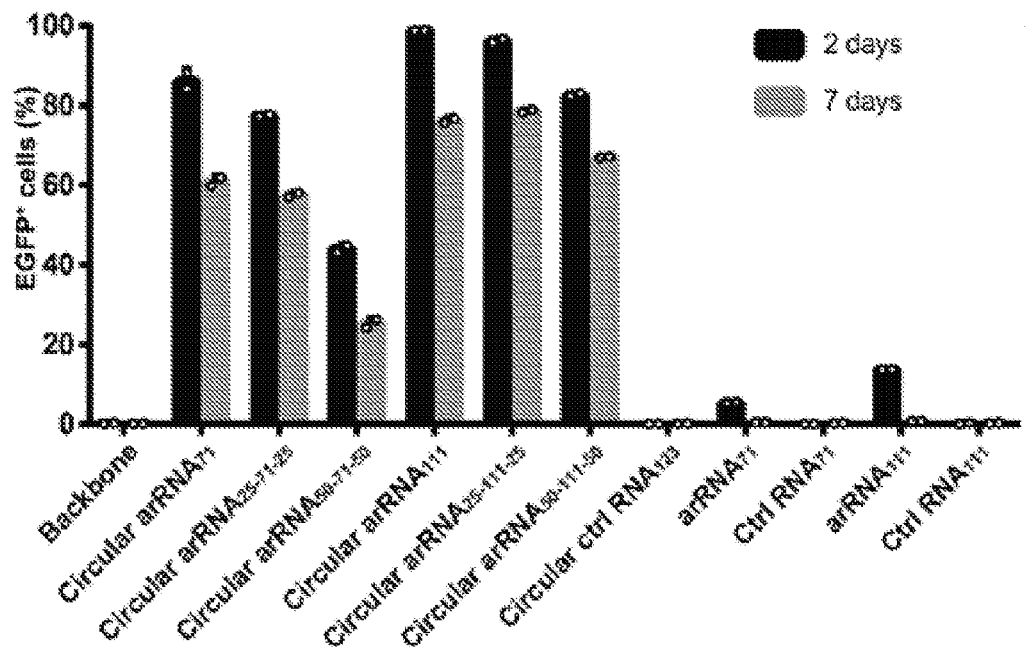
Figure 4C:
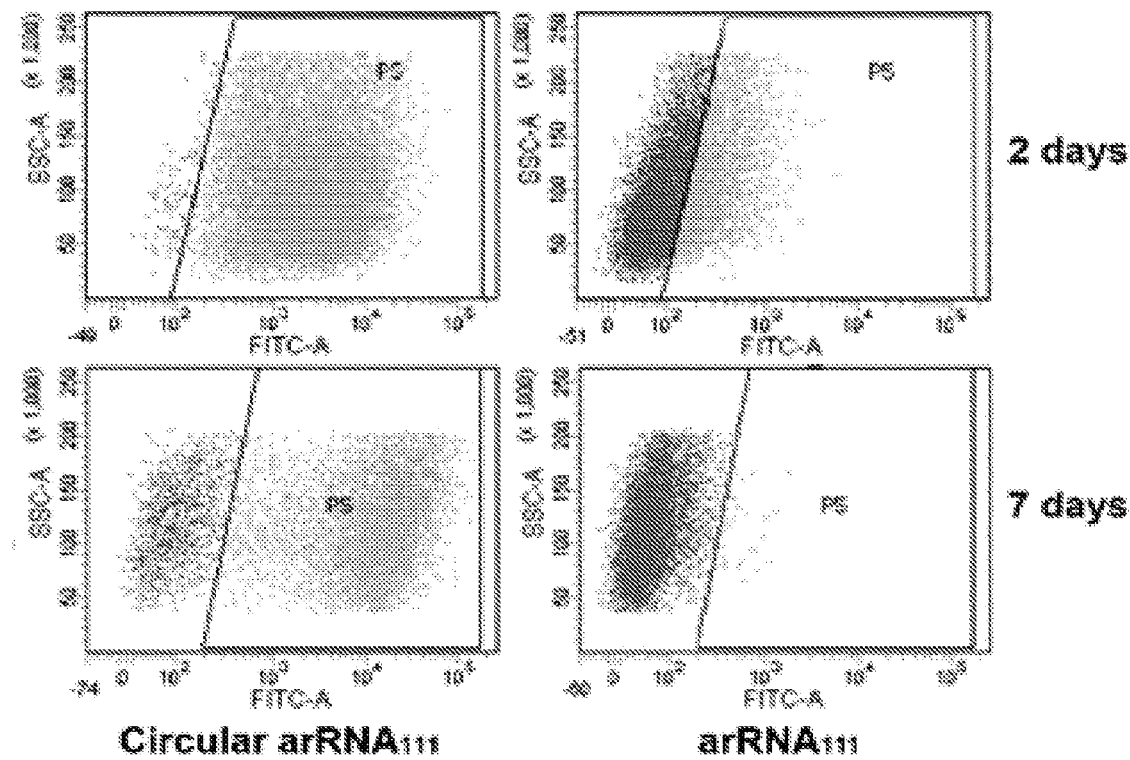

HEK293T cells stably expressing the Reporter-1 containing an in-frame stop codon between mCherry and EGFP (FIG. 4B) were transfected with plasmids expressing circular arRNA$_{71}$ and circular arRNA$_{111}$ both targeting the Reporter-1. The EGFP fluorescence indicates the efficiency of target editing on RNA. To test most efficient arRNA architecture, circular arRNAs were flanked with 25-nt or 50-nt linker connecting to both ends ligation sequence (FIG. 4A). For comparison, linear (non-circular) arRNA$_{71}$ and arRNA$_{111}$ were also transfected at the same time. It turned out that circular arRNAs strongly improved both the ratios of EGFP$^+$ cells and EGFP intensity (FIG. 4C) compared with linear arRNAs, while circular arRNA with 25-nt or 50-nt linker weakened the improvement of efficiency (FIG. 4).

Figure 4D:
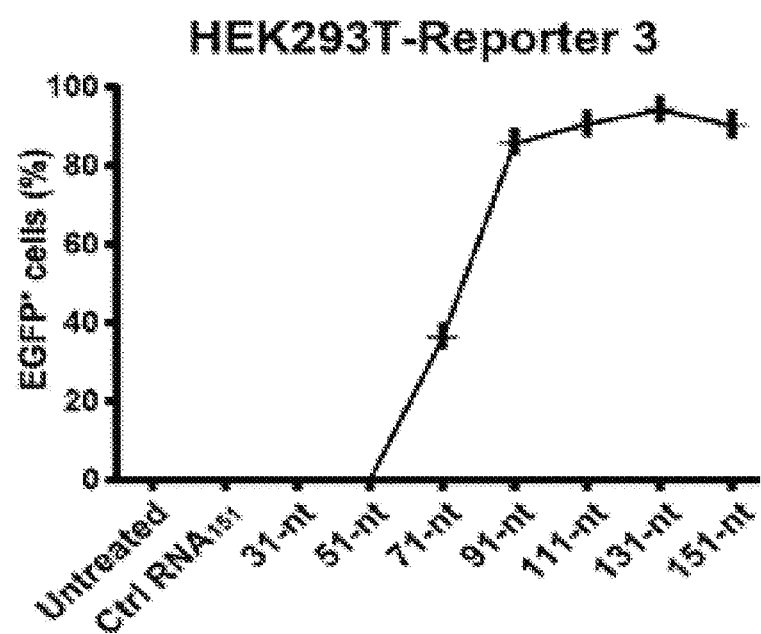

In HEK293T stably expressing the Reporter-3 (FIG. 4B), the effect of length on editing efficiency was further tested. Based on the reporter EGFP ratios, the length of circular arRNA correlated with the editing efficiency positively, peaking at 111- to 151-nt (FIG. 4D) and 71-nt was the minimal length for circular arRNA activity (FIG. 4D).

Dual fluorescence reporter-3 comprises sequence of mCherry (SEQ ID NO:21), sequence comprising 1×GS linker (shown as italic and bold characters) and the targeted A (SEQ (SEQ ID NO: 24)
CTGCAG*GGCGGAGGAGGCAGC*GCCTGCTCGCGATGCTAGAGGGCTCTG CCA
(sequence comprising 1 × GS linker (shown as
italic and bold characters) and the targeted A
(shown as larger and bold A))

Figure 4E:
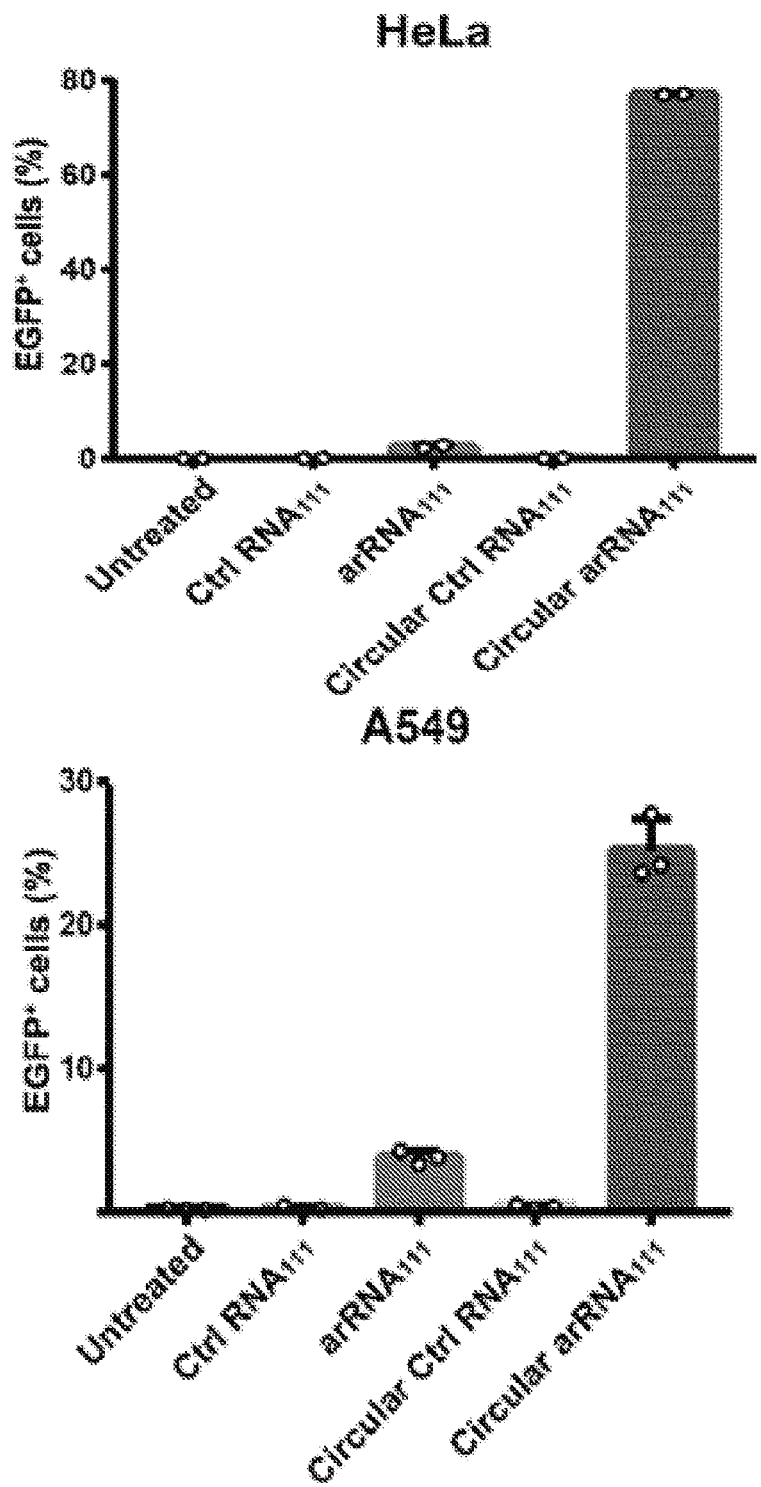

The circular arRNAs were used in HeLa and A549 cells in which LEAPER efficiencies are relatively low among multiple cell lines we have tested because of low expression level of ADAR1 or high expression of ADAR3. It turned out that circular arRNAs significantly boosted the editing efficiency in both cell lines based on EGFP reporter assay's (FIG. 4E).

| Name | Sequence (5'--->3') |
|---|---|
| 5' ligation sequence | AACCAUGCCGACUGAUGGCAG (SEQ ID NO: 25) |
| 3' ligation sequence | CUGCCAUCAGUCGGCGUGGACUGUAG (SEQ ID NO: 26) |
| Circular arRNA$_{71}$ | ACAGCUCCUCGCCCUUGCUCACUGGCAGAGCCCUCCAG CAUCGCGAGCAGGCGCUGCCUCCUCCGCCGCUG (SEQ ID NO: 27) |
| Circular arRNA$_{25\text{-}71\text{-}25}$ | CACACACAAACACACACAACACAACACAGCUCCUCGCC CUUGCUCACUGGCAGAGCCCUCCAGCAUCGCGAGCAGG CGCUGCCUCCUCCGCCGCUGCAACACACAAAACCACCA CACCAAC (SEQ ID NO: 28) |
| Circular arRNA$_{50\text{-}71\text{-}50}$ | ACCACACACACAACCACCACACACACACACAAACAC ACACAACACAACACAGCUCCUCGCCCUUGCUCACUGGC AGAGCCCUCCAGCAUCGCGAGCAGGCGCUGCCUCCUCC GCCGCUGCAACACACAAAACCACCACACCAACCCCAAC AACCACACACCCACACAAC (SEQ ID NO: 29) |
| Circular arRNA$_{111}$ | GAUGGGCACCACCCCGGUGAACAGCUCCUCGCCCUUGC UCACUGGCAGAGCCCUCCAGCAUCGCGAGCAGGCGCUG CCUCCUCCGCCGCUGCCUCCUCCGCCGCUGCCUCC (SEQ ID NO: 30) |
| Circular arRNA$_{25\text{-}111\text{-}25}$ | CACACACAAACACACACAACACAACGAUGGGCACCACC CCGGUGAACAGCUCCUCGCCCUUGCUCACUGGCAGAGC CCUCCAGCAUCGCGAGCAGGCGCUGCCUCCUCCGCCGC UGCCUCCUCCGCCGCUGCCUCCCAACACACAAAACCAC CACACCAAC (SEQ ID NO: 31) |
| Circular arRNA$_{50\text{-}111\text{-}50}$ | ACCACACACACAACCACCACACACACACACAAACAC ACACAACACAACGAUGGGCACCACCCCGGUGAACAGCU CCUCGCCCUUGCUCACUGGCAGAGCCCUCCAGCAUCGC GAGCAGGCGCUGCCUCCUCCGCCGCUGCCUCCUCCGCC GCUGCCUCCCAACACACAAAACCACCACACCAACCCCA ACAACCACACACCCACACAAC (SEQ ID NO: 32) |
| Circular ctrl RNA$_{123}$ | UUGCCAUGUGUAUGUGGGGAGACGGUCGGGUCCAGAUA UUCGUAUCUGUCGAGUAGAGUGUGGGCUCCCCACAUAC UCUGAUGAUCCAGAGACGAUAUUACGUCUCAGGAUCAU UCAUGGCAA (SEQ ID NO: 33) |
| arRNA$_{71}$ | ACAGCUCCUCGCCCUUGCUCACUGGCAGAGCCCUCCAG CAUCGCGAGCAGGCGCUGCCUCCUCCGCCGCUG (SEQ ID NO: 34) |
| Ctrl arRNA$_{71}$ | UUUCAGCUAUACCUGCCCGGUAUAAAGGGACGUUCACA CCGCGAUGUUCUCUGCUGGGGAAUUGCGCGAUA (SEQ ID NO: 35) |
| arRNA$_{111}$ | GAUGGGCACCACCCCGGUGAACAGCUCCUCGCCCUUGC UCACUGGCAGAGCCCUCCAGCAUCGCGAGCAGGCGCUG CCUCCUCCGCCGCUGCCUCCUCCGCCGCUGCCUCC (SEQ ID NO: 36) |
| Ctrl arRNA$_{111}$ | UACCGCUACAGCCACGCUGAUUUCAGCUAUACCUGCCC GGUAUAAAGGGACGUUCACACCGCGAUGUUCUCUGCUG GGGAAUUGCGCGAUAUUCAGGAUUAAAAGAAGUGC (SEQ ID NO: 37) |
| Ctrl arRNA$_{151}$ (circular) | ACUACAGUUGCUCCGAUAUUUAGGCUACGUCAAUAGGC ACUAACUUAUUUGGCGCUGGUGAACGGACUUCCUCUCGA GUACCAGAAGAUGACUACAAAACUCCUUUCCAUUGCGA GUAUCGGAGUCUGGCUCAGUUUGGCCAGGGAGGCACU (SEQ ID NO: 38) |
| 31-nt | ACUGGCAGAGCCCUCCAGCAUCGCGAGCAGG (SEQ ID NO: 39) |
| 51-nt | GCCCUUGCUCACUGGCAGAGCCCUCCAGCAUCGCGAGC AGGCGCUGCCUCC (SEQ ID NO: 40) |
| 71-nt | ACAGCUCCUCGCCCUUGCUCACUGGCAGAGCCCUCCAG CAUCGCGAGCAGGCGCUGCCUCCUCCGCCCUGC (SEQ ID NO: 41) |
| 91-nt | ACCCCGGUGAACAGCUCCUCGCCCUUGCUCACUGGCAG AGCCCUCCAGCAUCGCGAGCAGGCGCUGCCUCCUCCGC CCUGCAGCUUGUACA (SEQ ID NO: 42) |
| 111-nt | GAUGGGCACCACCCCGGUGAACAGCUCCUCGCCCUUGC UCACUGGCAGAGCCCUCCAGCAUCGCGAGCAGGCGCUG CCUCCUCCGCCCUGCAGCUUGUACAGCUCGUCCAU (SEQ ID NO: 43) |
| 131-nt | GCUCGACCAGGAUGGGCACCACCCCGGUGAACAGCUCC UCGCCCUUGCUCACUGGCAGAGCCCUCCAGCAUCGCGA GCAGGCGCUGCCUCCUCCGCCCUGCAGCUUGUACAGCU CGUCCAUGCCGCCGGUG (SEQ ID NO: 44) |
| 151-nt | UCGCCGUCCAGCUCGACCAGGAUGGGCACCACCCCGGU GAACAGCUCCUCGCCCUUGCUCACUGGCAGAGCCCUCC AGCAUCGCGAGCAGGCGCUGCCUCCUCCGCCCUGCAGC UUGUACAGCUCGUCCAUGCCGCCGGUGGAGUGGCGGC (SEQ ID NO: 45) |
| arRNA$_{111}$ | GAUGGGCACCACCCCGGUGAACAGCUCCUCGCCCUUGC UCACUGGCAGAGCCCUCCAGCAUCGCGAGCAGGCGCUG CCUCCUCCGCCGCUGCCUCCUCCGCCGCUGCCUCC (SEQ ID NO: 46) |
| Ctrl arRNA$_{111}$ | UACCGCUACAGCCACGCUGAUUUCAGCUAUACCUGCCC GGUAUAAAGGGACGUUCACACCGCGAUGUUCUCUGCUG GGGAAUUGCGCGAUAUUCAGGAUUAAAAGAAGUGC (SEQ ID NO: 47) |
| Circular arRNA$_{111}$ | GAUGGGCACCACCCCGGUGAACAGCUCCUCGCCCUUGC UCACUGGCAGAGCCCUCCAGCAUCGCGAGCAGGCGCUG CCUCCUCCGCCGCUGCCUCCUCCGCCGCUGCCUCC (SEQ ID NO: 48) |
| Circular Ctrl arRNA$_{111}$ | UACCGCUACAGCCACGCUGAUUUCAGCUAUACCUGCCC GGUAUAAAGGGACGUUCACACCGCGAUGUUCUCUGCUG GGGAAUUGCGCGAUAUUCAGGAUUAAAAGAAGUGC (SEQ ID NO: 49) |

Figure 5:
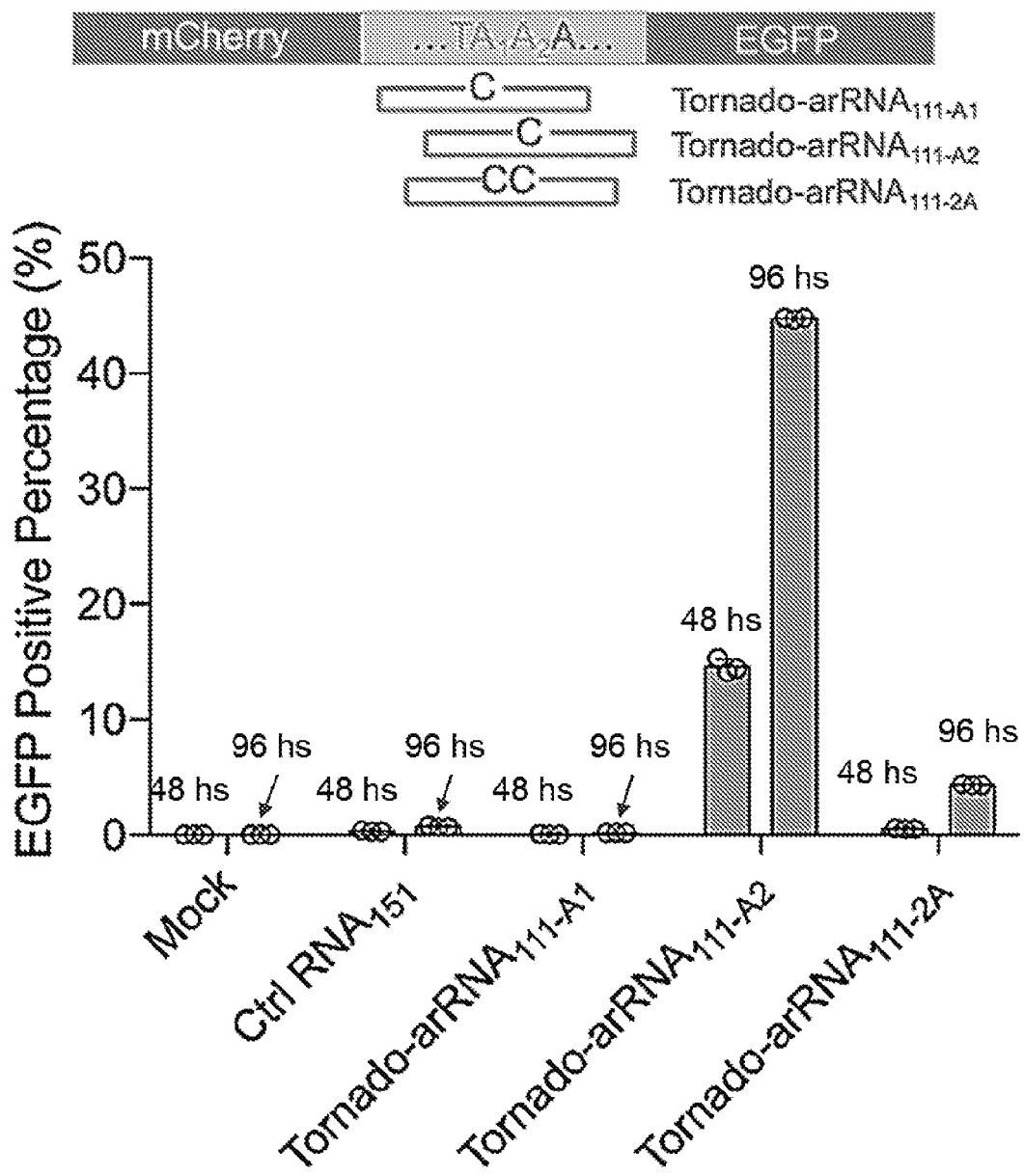
FIG. 5 depicts FACS analysis after co-transfection of various circular arRNAs for 48 hrs and 96 hrs, and EGFP positive percentages were normalized by transfection efficiency, which was determined by mCherry positive. Data are mean values±s.d. (n=3).

Example 4. Correcting the Premature Stop Codon Using the LEAPER System with Circular arRNAs Many diseases are caused by premature stop codon (PTC). To examine the potential of LEAPER-circular arRNA in treating PTC-related disease, an in frame UAA stop codon reporter was constructed. Three versions of circular arRNAs (i.e., Tornado-arRN$_{A111\text{-}A1}$, Tornado-arRNA$_{111\text{-}A2}$ and Tornado-arRN$_{A111\text{-}2A}$) were designed to target the UAA site of this reporter and compared the EGFP positive percentage of three different arRNAs. It turned out that that Tornado-arRNA$_{111\text{-}A2}$, which targets the second adenosine of the TAA codon, is more efficient (FIG. 5).

Figure 6A:
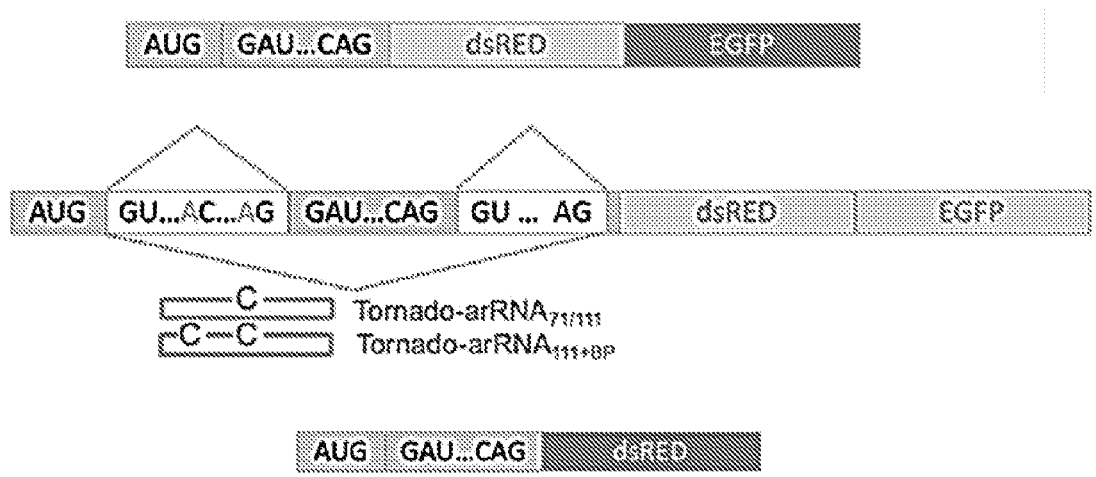
FIGS. 6A-6B depict FACS analysis after co-transfection of various circular arRNAs in HEK293T cells for 48 hrs and 96 hrs. EGFP positive percentages were normalized by transfection efficiency, which was determined by mCherry positive. Data are mean values±s.d. (n=3).
Figure 6B:
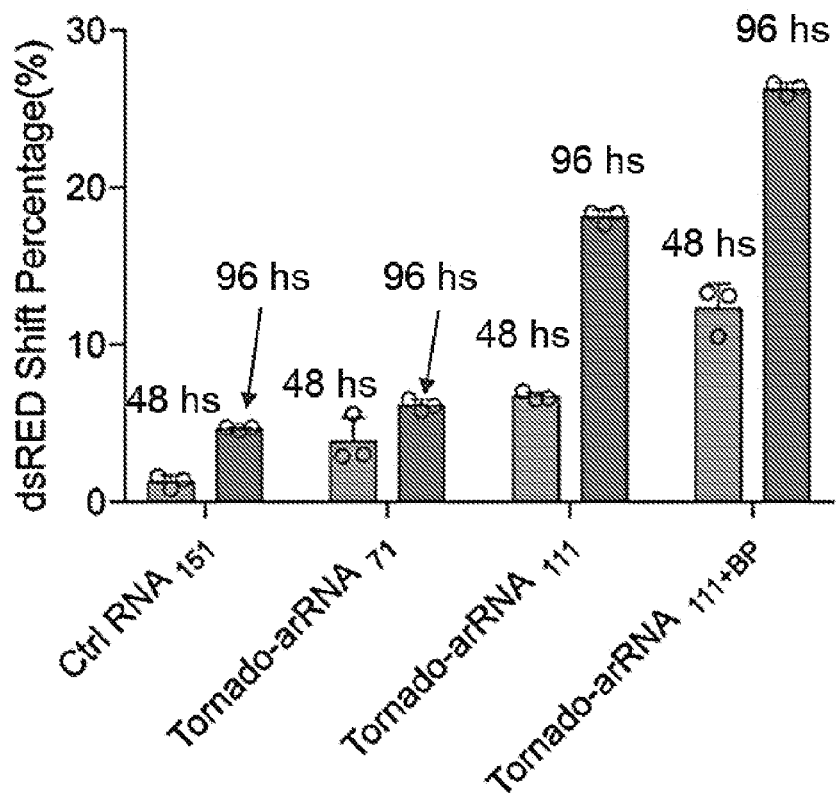

Example 5. Modulation of mRNA Splicing Using the LEAPER System with Circular arRNAs Manipulating mRNA splicing to generate novel splicing products is a strategy to cure diseases, such as Duchene muscular dystrophy. RG6 splicing reporter was used to test if LEAPER-circular arRNAs could change splicing acceptor site. Three versions of circular arRNAs were designed to target RG6 splicing acceptor site, including Tornado-arRNA$_{71}$ (71-nt). Tornado-arRNA$_{71}$(111-nt), and Tornado-arRNA$_{71+BP}$ (111-nt targeting both acceptor site and a branch point). In HEK293T cell, the RG6 reporter expressed more dsRNA protein over EGFP protein if the splicing if the splicing pattern was changed by LEAPER-Tornado (FIG. 6A). We found that LEAPER-circular arRNAs can efficiently target the cellular splicing machinery (FIG. 6B).

Example 6. Lentiviral Delivery of the LEAPER System with Circular arRNAs

Figure 7:
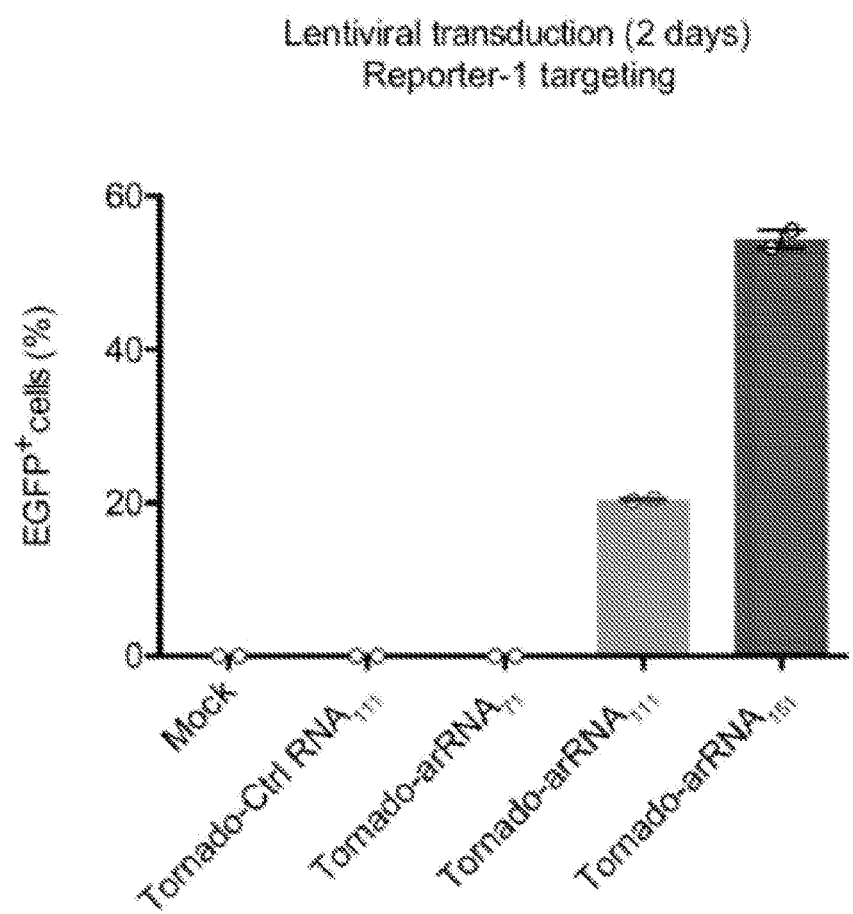
FIG. 7 depicts quantification of the EGFP positive (EGFP+) cells. Cells stably expressing Reporter-1 were infected with various Tornado-arRNA lentivirus, including the Tornado Ctrl RNA111 virus and the targeting Tornado-arRNA virus with different length, followed by FACS 2 days after infection. Data are mean values±s.e.m. (n=2).

Continuous dosing of therapeutic RNA is important for its efficacy. It was tested whether lentiviral delivery of LEAPER with circular arRNAs could achieve RNA editing. It was found that LEAPER with circular arRNAs could work through lentivirus delivery, by which various Tornado-arRNA could integrate into genome and stably expressed. The length of Tornado-arRNA correlated positively with the editing efficiency (FIG. 7).

REFERENCES

1 Porteus, M. H. & Carroll, D. Gene targeting using zinc finger nucleases. *Nat Biotechnol* 23, 967-973 (2005).
2 Boch, J. et al. Breaking the code of DNA binding specificity of TAL-type III effectors. *Science* 326, 1509-1512 (2009).
3 Moscou, M. J. & Bogdanove, A. J. A simple cipher governs DNA recognition by TAL effectors. *Science* 326, 1501 (2009).
4 Miller, J. C. et al. A TALE nuclease architecture for efficient genome editing. *Nat Biotechnol* 29, 143-148 (2011).
5 Jinek, M. et al A programmable dual-RNA-guided DNA endonuclease in adaptive bacterial immunity. *Science* 337, 816-821 (2012).
6 Cong, L. et al. Multiplex genome engineering using CRISPR-Cas systems. *Science* 339, 819-823 (2013).
7 Mali, P. et al. RNA-guided human genome engineering via Cas9. *Science* 339, 823-826 (2013).
8 Komor, A. C., Kim, Y. B., Packer, M. S., Zuris, J. A. & Liu, D. R. Programmable editing of a target base in genomic DNA without double-stranded DNA cleavage. *Nature* 533, 420-424 (2016).
9 Ma, Y. et al. Targeted AID-mediated mutagenesis (TAM) enables efficient genomic diversification in mammalian cells. *Nat Methods* 13, 1029-1035 (2016).
10 Gaudelli, N. M. e/al. Programmable base editing of A*T to G*C in genomic DNA without DNA cleavage. *Nature* 551, 464-471 (2017).
11 Tan, M. H. et al. Dynamic landscape and regulation of RNA editing in mammals. *Nature* 550, 249-254 (2017).
12 Nishikura, K. Functions and regulation of RNA editing by ADAR deaminases. *Annu Rev Biochem* 79, 321-349 (2010).
13 Bass, B. L. & Weintraub. H. An unwinding activity that covalently modifies its double-stranded RNA substrate. *Cell* 55, 1089-1098 (1988).
14 Wong, S. K., Sato, S. & Lazinski, D. W. Substrate recognition by ADAR1 and ADAR2. *RNA* 7, 846-858 (2001).
15 Montiel-Gonzalez. M. F., Vallecillo-Viejo, I., Yudowski, G. A. & Rosenthal, J. J. Correction of mutations within the cystic fibrosis transmembrane conductance regulator by site-directed RNA editing. *Proc Natl Acad Sci USA* 110, 18285-18290 (2013).
16 Sinnamon, J. R. et al. Site-directed RNA repair of endogenous Mecp2 RNA in neurons. *Proc Natl Acad Sci USA* 114, E9395-E9402 (2017).
17 Montiel-Gonzalez, M. F., Vallecillo-Viejo, I. C. & Rosenthal, J. J. An efficient system for selectively altering genetic information within mRNAs. *Nucleic Acids Res* 44, e157 (2016).
18 Hanswillemenke, A., Kuzdere, T., Vogel, P., Jekely, G. & Stafforst, T. Site-Directed RNA Editing in Vivo Can Be Triggered by the Light-Driven Assembly of an Artificial Riboprotein. *J Am Chem Soc* 137, 15875-15881 (2015).
19 Schneider. M. F., Wettengel, J., Hoffmann, P. C. & Stafforst, T. Optimal guideRNAs for re-directing deaminase activity of hADAR1 and hADAR2 in trans. *Nucleic Acids Res* 42, e87 (2014).
Vogel, P., Hanswillemenke, A. & Stafforst, T. Switching Protein Localization by Site-Directed RNA Editing under Control of Light. *ACS synthetic biology* 6, 1642-1649 (2017).
21 Vogel, P. Schneider. M. F., Wettengel, J. & Stafforst, T. Improving site-directed RNA editing in vitro and in cell culture by chemical modification of the guideRNA. *Angewandte Chemie* 53, 6267-6271 (2014).
22 Vogel. P. et al. Efficient and precise editing of endogenous transcripts with SNAP-tagged ADARs *Nat Methods* 15, 535-538 (2018).
23 Cox, D. B. T. et al. RNA editing with CRISPR-Cas13. *Science* 358, 1019-1027 (2017).
24 Fukuda, M. et al. Construction of a guide-RNA for site-directed RNA mutagenesis utilising intracellular A-to-I RNA editing. *Scientific reports* 7, 41478 (2017).
25 Wettengel, J., Reautschnig, P., Geisler, S., Kahle, P. J. & Stafforst, T. Harnessing human ADAR2 for RNA repair—Recoding a PINK1 mutation rescues mitophagy. *Nucleic Acids Res* 45, 2797-2808 (2017).
26 Heep, M., Mach, P., Reautschnig, P., Wettengel, J. & Stafforst, T. Applying Human ADAR1p110 and ADAR1p150 for Site-Directed RNA Editing-G/C Substitution Stabilizes GuideRNAs against Editing. *Genes (Basel)* 8 (2017).
27 Katrekar, D. et al. In vivo RNA editing of point mutations via RNA-guided adenosine deaminases. *Nat Methods* 16, 239-242 (2019).
28 Yin, H., Kauffman, K. J. & Anderson, D. G. Delivery technologies for genome editing. *Nat Rev Drug Discov* 16, 387-399 (2017).
29 Platt, R. J. et al. CRISPR-Cas9 knockin mice for genome editing and cancer modeling. *Cell* 159, 440-455 (2014).
Chew, W. L. et al. A multifunctional AAV-CRISPR-Cas9 and its host response. *Nat Methods* 13, 868-874 (2016).
31 Teoh, P. J. et al. Aberrant hyperediting of the myeloma transcriptome by ADAR1 confers oncogenicity aid is a marker of poor prognosis. *Blood* 132, 1304-1317 (2018).
32 Vallecillo-Viejo, I. C., Liscovitch-Brauer, N., Montiel-Gonzalez, M. F., Eisenberg. E. & Rosenthal, J. J. C. Abundant off-target edits from site-directed RNA editing can be reduced by nuclear localization of the editing enzyme. *RNA biology* 15, 104-114 (2018).

33 Mays. L. E. & Wilson, J. M. The complex and evolving story of T cell activation to AAV vector-encoded transgene products. *Mol Ther* 19, 16-27 (2011).
34 Wagner. D. L. et al. High prevalence of *Streptococcus pyogenes* Cas9-reactive T cells within the adult human population. *Nat Med* 25, 242-248 (2019).
35 Simhadri, V. L. et al. Prevalence of Pre-existing Antibodies to CRISPR-Associated Nuclease Cas9 in the USA Population. *Mol Ther Methods Clin Dev* 10, 105-112 (2018).
36 Charlesworth, C. T. et at. Identification of preexisting adaptive immunity to Cas9 proteins in humans. *Nat Med* 25, 249-254 (2019).
37 Haapaniemi. E., Botla, S., Persson, J., Schmierer, B. & Taipale, J. CRISPR-Cas9 genome editing induces a p53-mediated DNA damage response. *Nat Med* 24, 927-930 (2018).
38 Ihry, R. J. et al. p53 inhibits CRISPR-Cas9 engineering in human pluripotent stem cells. Nat Med 24, 939-946 (2018).

We claim:

1. A method for editing a target RNA comprising a target adenosine in a host cell, comprising introducing a construct comprising a nucleic acid encoding the dRNA into the host cell, wherein:
   (1) the dRNA comprises a targeting RNA sequence that is at least partially complementary to the target RNA,
   (2) the dRNA is capable of recruiting an adenosine deaminase acting on RNA (ADAR), and
   (3) the dRNA forms a circular RNA within the host cell, wherein the circular RNA recruits an ADAR to deaminate a target adenosine in the target RNA;
   wherein the dRNA further comprises: (i) a 3' ligation sequence and a 5' ligation sequence; or (ii) a 3' twister ribozyme sequence linked to the 3' end of the nucleic acid encoding the dRNA and a 5' twister ribozyme sequence linked to the 5' end of the nucleic acid encoding the dRNA.

2. The method of claim 1, wherein the dRNA further comprises a 3' ligation sequence and a 5' ligation sequence.

3. The method of claim 1, wherein the dRNA is circularized by RNA ligase RtcB in the host cell.

4. The method of claim 1, wherein the construct further comprises a 3' twister ribozyme sequence linked to the 3' end of the nucleic acid encoding the dRNA and a 5' twister ribozyme sequence linked to the 5' end of the nucleic acid encoding the dRNA.

5. The method of claim 4, wherein:
   (i) the 3' twister sequence is twister P3 U2A and the 5' twister sequence is twister P1; or
   (ii) the 5' twister sequence is twister P3 U2A and the 3' twister sequence is twister P1.

6. The method of claim 1, wherein the construct further comprises a promoter operably linked to the nucleic acid encoding the dRNA, wherein the promoter is a polymerase II promoter ("Pol II promoter") or a polymerase III promoter ("Pol III promoter").

7. The method of claim 6, wherein the Pol II promoter is a CMV promoter.

8. The method of claim 6, wherein the Pol III promoter is a U6 promoter.

9. The method of claim 1, wherein the construct is an adeno-associated virus (AAV) vector.

10. The method of claim 1, wherein the ADAR is endogenously expressed by the host cell.

11. The method of claim 1, wherein:
    (i) the targeting RNA sequence is more than 50 nucleotides in length;
    (ii) the targeting RNA sequence comprises a cytidine, adenosine, or uridine directly opposite the target adenosine in the target RNA;
    (iii) the targeting RNA sequence further comprises one or more guanosines each opposite a non-target adenosine in the target RNA;
    (iv) the targeting RNA sequence comprises two or more consecutive mismatch nucleotides opposite a non-target adenosine in the target RNA;
    (v) the 5' nearest neighbor of the target adenosine in the target RNA is a nucleotide selected from U, C, A, and G with the preference of U>C≈A>G, and the 3' nearest neighbor of the target adenosine in the target RNA is a nucleotide selected from G, C, A, and U with the preference of G>C>A≈U;
    (vi) the target adenosine is in a three-base motif selected from the group consisting of UAG, UAC, UAA, UAU, CAG, CAC, CAA, CAU, AAG, AAC, AAA, AAU, GAG, GAC, GAA, and GAU in the target RNA; and/or
    (vii) the target RNA is an RNA selected from the group consisting of a pre-messenger RNA, a messenger RNA, a ribosomal RNA, a transfer RNA, a long non-coding RNA, and a small RNA.

12. The method of claim 1, comprising introducing a plurality of or constructs comprising nucleic acids encoding the dRNAs each targeting a different target RNA.

13. The method of claim 1, wherein the construct comprising nucleic acid encoding the dRNA does not induce immune response.

14. The method of claim 1, wherein the ADAR is introduced to the host cell.

15. The method of claim 1, wherein deamination of the target adenosine in the target RNA by the recruited ADAR results in i) a missense mutation, an early stop codon, aberrant splicing, or alternative splicing in the target RNA, or ii) reversal of a missense mutation, an early stop codon, aberrant splicing, or alternative splicing in the target RNA.

16. The method of claim 1, wherein the host cell is a mammalian cell.

17. A method for treating a disease or condition associated with a target RNA in an individual, comprising editing the target RNA in a cell of the individual according to the method of claim 1.

18. A method for editing a target RNA comprising a target adenosine in a host cell, comprising introducing a deaminase-recruiting RNA (dRNA) into the host cell, wherein:
    (1) the dRNA comprises a targeting RNA sequence that is at least partially complementary to the target RNA,
    (2) the dRNA is capable of recruiting an adenosine deaminase acting on RNA (ADAR), and (3) the dRNA is a circular RNA, wherein the circular RNA recruits an ADAR to deaminate a target adenosine in the target RNA.

19. The method of claim 18, wherein the ADAR is endogenously expressed by the host cell.

20. The method of claim 18, wherein:
(i) the targeting RNA sequence is more than 50 nucleotides in length;
(ii) the targeting RNA sequence comprises a cytidine, adenosine, or uridine directly opposite the target adenosine in the target RNA;
(iii) the targeting RNA sequence further comprises one or more guanosines each opposite a non-target adenosine in the target RNA;
(iv) the targeting RNA sequence comprises two or more consecutive mismatch nucleotides opposite a non-target adenosine in the target RNA;
(v) the 5' nearest neighbor of the target adenosine in the target RNA is a nucleotide selected from U, C, A, and G with the preference of U>C≈A>G, and the 3' nearest neighbor of the target adenosine in the target RNA is a nucleotide selected from G, C, A, and U with the preference of G>C>N≈U;
(vi) the target adenosine is in a three-base motif selected from the group consisting of UAG, UAC, UAA, UAU, CAG, CAC, CAA, CAU, AAG, AAC, AAA, AAU, GAG, GAC, GAA, and GAU in the target RNA; and/or
(vii) the target RNA is an RNA selected from the group consisting of a pre-messenger RNA, a messenger RNA, a ribosomal RNA, a transfer RNA, a long non-coding RNA, and a small RNA.

21. The method of claim 18, comprising introducing a plurality of dRNAs each targeting a different target RNA.

22. The method of claim 18, wherein deamination of the target adenosine in the target RNA by the recruited ADAR results in i) a missense mutation, an early stop codon, aberrant splicing, or alternative splicing in the target RNA, or ii) reversal of a missense mutation, an early stop codon, aberrant splicing, or alternative splicing in the target RNA.

23. The method of claim 18, wherein the host cell is a mammalian cell.

24. The method of claim 18, wherein the dRNA does not induce immune response.

25. A method for treating a disease or condition associated with a target RNA in an individual, comprising editing the target RNA in a cell of the individual according to the method of claim 18.

* * * * *